(12) United States Patent  
Nomura et al.

(10) Patent No.: US 8,178,216 B2
(45) Date of Patent: May 15, 2012

(54) QUINOXALINE DERIVATIVE, AND LIGHT-EMITTING ELEMENT, LIGHT-EMITTING DEVICE, AND ELECTRONIC DEVICE INCLUDING QUINOXALINE DERIVATIVE

(75) Inventors: Hiroko Nomura, Kanagawa (JP); Sachiko Kawakami, Kanagawa (JP); Nobuharu Ohsawa, Kanagawa (JP); Ryoji Nomura, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 560 days.

(21) Appl. No.: 12/070,650

(22) Filed: Feb. 20, 2008

(65) Prior Publication Data
US 2009/0072718 A1    Mar. 19, 2009

(30) Foreign Application Priority Data

Feb. 28, 2007  (JP) ................. 2007-050244

(51) Int. Cl.
*H01L 51/54* (2006.01)
*C07D 241/36* (2006.01)
(52) U.S. Cl. ........ 428/690; 428/917; 313/504; 313/506; 544/353
(58) Field of Classification Search ................. None
See application file for complete search history.

(56) References Cited

U.S. PATENT DOCUMENTS
4,760,006 A  7/1988  Pawlowski
(Continued)

FOREIGN PATENT DOCUMENTS
EP    0 166 230 A1    1/1986
(Continued)

OTHER PUBLICATIONS

Delvigs, P., "Effects of Multifunctional Crosslinking Agents on the Thermomechanical Properties of Polyimide Films," Polymer Engineering and Science, vol. 16, No. 5, May 1976, pp. 323-326.

(Continued)

*Primary Examiner* — Dawn Garrett
(74) *Attorney, Agent, or Firm* — Husch Blackwell LLP

(57) ABSTRACT

An object of the present invention is to provide a quinoxaline derivative represented by a general formula (1). $Ar^1$ represents one of a substituted or unsubstituted biphenyl group, and a substituted or unsubstituted terphenyl group; $Ar^2$ represents one of a substituted or unsubstituted phenyl group, a substituted or unsubstituted biphenyl group, and a substituted or unsubstituted terphenyl group; $\alpha^1$ represents an arylene group having 6 to 25 carbon atoms; and $R^{11}$ to $R^{15}$ are the same or different from one another, and each of them represents any one of a hydrogen atom, an alkyl group having 1 to 4 carbon atoms, and a substituted or unsubstituted aryl group having 6 to 25 carbon atoms.

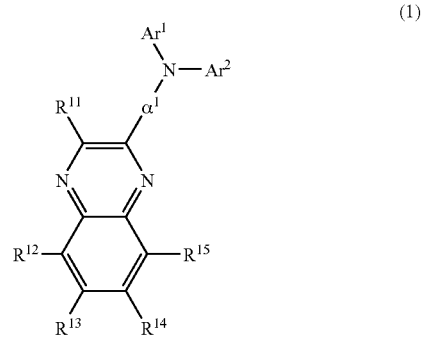

22 Claims, 29 Drawing Sheets

U.S. PATENT DOCUMENTS

| | | | |
|---|---|---|---|
| 5,366,811 A | 11/1994 | Higashi et al. | |
| 5,466,392 A | 11/1995 | Hironaka et al. | |
| 6,097,147 A | 8/2000 | Baldo et al. | |
| 6,303,238 B1 | 10/2001 | Thompson et al. | |
| 6,541,129 B1 | 4/2003 | Kawamura et al. | |
| 6,723,445 B2 | 4/2004 | Li et al. | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 7,034,026 B2 | 4/2006 | Barnett et al. | |
| 7,074,534 B2 | 7/2006 | Herron et al. | |
| 7,238,806 B2 | 7/2007 | Inoue et al. | |
| 7,245,073 B2 | 7/2007 | Shitagaki et al. | |
| 7,271,858 B2 | 9/2007 | Yamazaki et al. | |
| 7,291,406 B2 | 11/2007 | Thompson et al. | |
| 7,399,537 B2 | 7/2008 | Kawamura et al. | |
| 7,601,435 B2* | 10/2009 | Shitagaki et al. | 428/690 |
| 7,615,925 B2* | 11/2009 | Suzuki et al. | 313/506 |
| 7,901,792 B2* | 3/2011 | Egawa et al. | 428/690 |
| 8,008,489 B2* | 8/2011 | Egawa et al. | 544/353 |
| 2003/0143430 A1 | 7/2003 | Kawamura et al. | |
| 2005/0065342 A1 | 3/2005 | Shitagaki et al. | |
| 2005/0186446 A1 | 8/2005 | Shitagaki et al. | |
| 2005/0191527 A1 | 9/2005 | Fujii et al. | |
| 2005/0221123 A1* | 10/2005 | Inoue et al. | 428/690 |
| 2005/0242715 A1 | 11/2005 | Inoue et al. | |
| 2006/0082294 A1 | 4/2006 | Kawamura et al. | |
| 2006/0263637 A1 | 11/2006 | Ohsawa et al. | |
| 2007/0059553 A1 | 3/2007 | Egawa et al. | |
| 2007/0213527 A1 | 9/2007 | Inoue et al. | |
| 2007/0222374 A1 | 9/2007 | Egawa et al. | |
| 2007/0241667 A1 | 10/2007 | Ohsawa et al. | |
| 2007/0244320 A1* | 10/2007 | Inoue et al. | 544/225 |
| 2008/0079354 A1* | 4/2008 | Egawa et al. | 313/503 |
| 2008/0241591 A1 | 10/2008 | Kawamura et al. | |
| 2008/0306239 A1* | 12/2008 | Horiba et al. | 528/332 |
| 2009/0153041 A1* | 6/2009 | Kawakami et al. | 313/504 |
| 2010/0069636 A1* | 3/2010 | Shitagaki et al. | 544/343 |
| 2010/0141130 A1* | 6/2010 | Egawa et al. | 313/504 |
| 2011/0186825 A1 | 8/2011 | Egawa et al. | |
| 2011/0248254 A1 | 10/2011 | Egawa et al. | |

FOREIGN PATENT DOCUMENTS

| | | |
|---|---|---|
| EP | 0 502 202 A1 | 9/1992 |
| EP | 1 029 909 A1 | 8/2000 |
| EP | 1 252 803 A | 6/2001 |
| EP | 1 616 864 A1 | 1/2006 |
| EP | 1 690 866 A1 | 8/2006 |
| JP | 60-258169 | 12/1985 |
| JP | 64-57261 | 3/1989 |
| JP | 7-48385 | 2/1995 |
| JP | 7-53954 | 2/1995 |
| JP | 7-150137 | 6/1995 |
| JP | 8-73443 | 3/1996 |
| JP | 10-25473 | 1/1998 |
| JP | 2000-309566 | 11/2000 |
| JP | 2003-40873 | 2/2003 |
| JP | 2003-515897 | 5/2003 |
| JP | 2006-16384 | 1/2006 |
| WO | WO 92/05131 A1 | 4/1992 |
| WO | WO 01/41512 A1 | 6/2001 |
| WO | WO 2004/094389 A1 | 11/2004 |
| WO | WO 2005/054261 A1 | 6/2005 |
| WO | WO 2005/115061 A1 | 12/2005 |
| WO | WO 2006/049334 A1 | 5/2006 |

OTHER PUBLICATIONS

Parker, S.P. et al, editors, *McGraw-Hill Dictionary of Chemical Terms*, 3rd edition, McGraw-Hill, publisher, 1984, p. 200.

Tang, C.W. et al, "Organic Electroluminescent Diodes," Applied Physics Letters, vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L-269-L-271.

Jakubke, H-D et al, editors, *Concise Encyclopedia Chemistry*, Walter de Gruyter, publisher, 1993, p. 490

Lewis, R.J., Sr., editor, *Hawley's Condensed Chemical Dictionary*, 12th edition, Van Nostrand Reinhold, publisher, 1993, p. 594.

Brock, T. et al, "Synthesis and Characterisation of Porous Particulate Polyimides," J. Mater. Chem., vol. 4, No. 2, 1994, pp. 229-236.

Thomas, K.R.J. et al, "Quinoxalines Incorporating Triarylamines: Potential Electroluminescent Materials with Tunable Emission Characteristics," Chem. Mater., vol. 14, No. 6, 2002, pp. 2796-2802.

Burrows, H.D. et al, "Fluorescence Study of Dehydroabietic Acid-Based Bipolar Arylamine-Quinoxalines," Journal of Fluorescence, vol. 16, No. 2, Mar. 2006, pp. 227-231.

Huang, T-H et al, "Quinoxalines Incorporating Triarylamines: Dipolar Electroluminescent Materials with Tunable Emission Characteristics," Journal of the Chinese Chemical Society, vol. 53, No. 1, 2006, pp. 233-242.

International Search Report re application No. PCT/JP2004/005022, dated Jun. 15, 2004 (in Japanese).

Written Opinion re application No. PCT/JP2004/005022, dated Jun. 15, 2004 (with English abstract).

International Search Report re application No. PCT/JP2006/317806, dated Nov. 21, 2006.

Written Opinion re application No. PCT/JP2006/317806, dated Nov. 21, 2006.

* cited by examiner

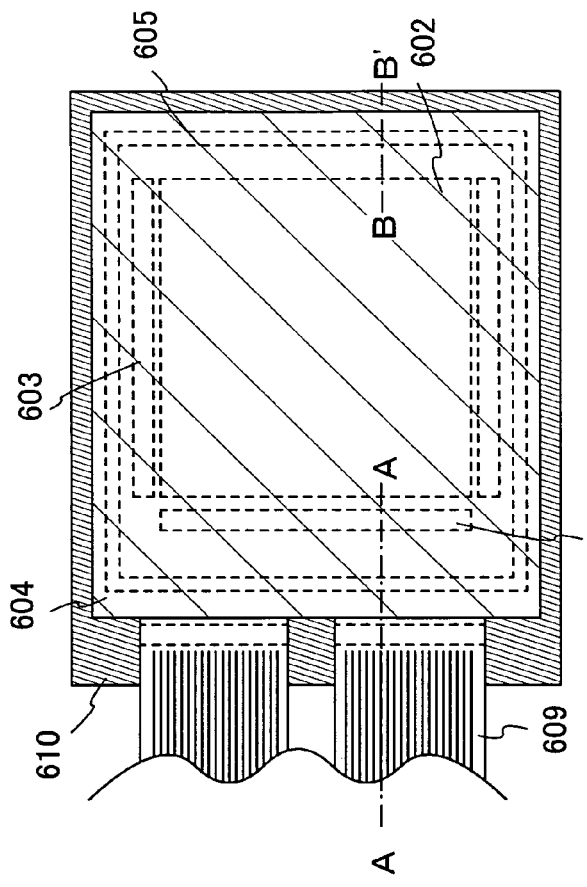
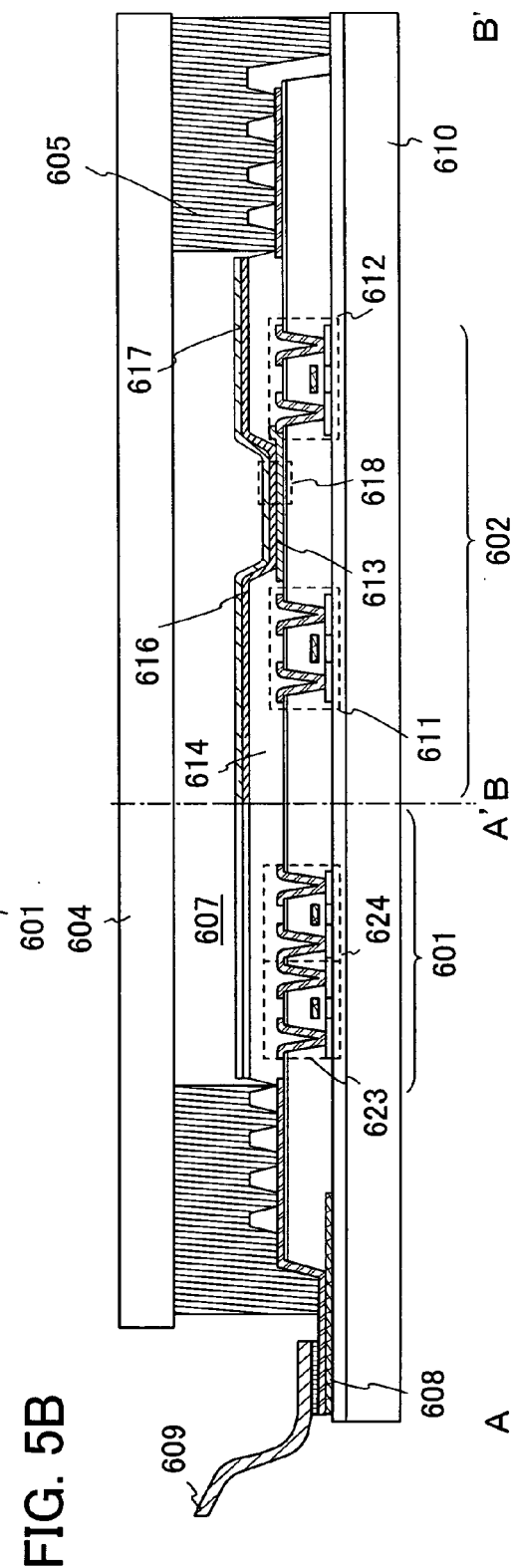
FIG. 5A
FIG. 5B

QUINOXALINE DERIVATIVE, AND LIGHT-EMITTING ELEMENT, LIGHT-EMITTING DEVICE, AND ELECTRONIC DEVICE INCLUDING QUINOXALINE DERIVATIVE

BACKGROUND OF THE INVENTION

1. Field of the Invention

The present invention relates to quinoxaline derivatives, and light-emitting elements, light-emitting devices, and electronic devices each including any of the quinoxaline derivatives.

2. Description of the Related Art

By using compounds, compared with inorganic compounds, a wider variety of structures can be taken and materials having various functions depending on the molecular design can be synthesized. Because of these advantages, photo electronics and electronics each using functional organic materials have been attracting attention in recent years.

As examples of electronic devices using functional organic materials, there are solar cells, light-emitting elements, organic transistors, and the like. These are devices using electric properties and optical properties of such organic compounds. In particular, light-emitting elements have been developing remarkably.

A light emission mechanism is said to be as follows: by applying a voltage to a pair of electrodes with a light-emitting layer interposed therebetween, electrons injected from a cathode and holes injected from an anode (hereinafter, electrons or holes are also referred to as carriers) are recombined with each other in an emission center of the light-emitting layer to form molecular excitons, and the molecular excitons release energy in returning to a ground state; accordingly light is emitted. A singlet excited state and a triplet excited state are known as excited states, and light emission is considered to be possible through either a singlet excited state or a triplet excited state.

Such light-emitting elements have a lot of material-dependant problems for improvement of element characteristics. In order to solve the problems, improvement of element structures, development of materials, and the like have been carried out.

The following is known as the most basic structure of light-emitting elements: a hole-transporting layer made of an organic compound having hole-transporting properties, and an electron-transporting light-emitting layer made of an organic compound having electron-transporting properties are stacked to form a thin film of approximately 100 nm thickness in total, and this thin film is interposed between electrodes (Non-Patent Document 1: C. W. Tang et al., Applied Physics Letters, vol. 51, No. 12, pp. 913-915 (1987)).

By applying a voltage to the light-emitting element described in Non-Patent Document 1, light emission can be obtained from the organic compound having electron-transporting properties.

Further, in the light-emitting element described in Non-Patent Document 1, functions are separated so that the hole-transporting layer transports holes, and the electron-transporting layer transports electrons and emits light. However, various interactions (e.g., exciplex formation) frequently occur at an interface of stacked layers. As a result, changes in the emission spectrum or the decrease in emission efficiency may occur.

In order to suppress the changes in the emission spectrum or the decrease in emission efficiency, which are caused by the interactions at the interface, a light-emitting element having further functional separation has been developed. For example, a light-emitting element has been proposed, in which a light-emitting layer is interposed between a hole-transporting layer and an electron-transporting layer (Non-Patent Document 2: Chihaya Adachi et al., Japanese Journal of Applied Physics, vol. 27, No. 2, L269-L271 (1988)).

In such a light-emitting element described in Non-Patent Document 2, in order to more effectively suppress the interaction occurring at the interface, it is preferable that the light-emitting layer be made of a bipolar organic compound having both electron-transporting properties and hole-transporting properties.

However, most organic compounds are monopolar materials having either hole-transporting properties or electron-transporting properties.

Therefore, bipolar organic compounds having both electron-transporting properties and hole-transporting properties should be developed.

Although a bipolar quinoxaline derivative is described in Patent Document 1 (PCT International Publication No. 2004/094389), its characteristics such as thermal stability are not satisfactory. Thus, a wider variety of bipolar organic compounds should be developed.

SUMMARY OF THE INVENTION

In view of the aforementioned problems, an object of the present invention is to provide a new bipolar organic compound.

Another object of the present invention is to provide a light-emitting element with an excellent carrier balance by using a bipolar organic compound of the present invention. Furthermore, another object is to provide a light-emitting element and light-emitting device with a low driving voltage and low power consumption by using the bipolar organic compound of the present invention.

Still another object of the present invention is to provide an electronic device with low power consumption by using the bipolar organic compound of the present invention.

An aspect of the present invention is a quinoxaline derivative represented by the following general formula (1).

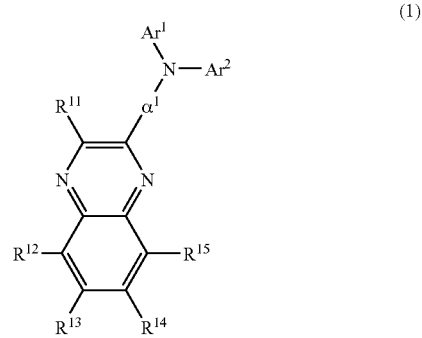

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^1$ represents an arylene group having 6 to 25 carbon atoms; and $R^{11}$ to $R^{15}$ may be the same or different from one another, and each of them represents any one of a hydrogen atom, an alkyl group having 1 to 4 carbon atoms, and a substituted or unsubstituted aryl group having 6 to 25 carbon atoms.

The above quinoxaline derivative is bipolar because it has a hole-transporting amine skeleton and an electron-transporting quinoxaline skeleton in the same molecule. Since the quinoxaline derivative is bipolar, the above quinoxaline derivative is preferable, in a light-emitting element, as a material in which a light-emitting substance is dispersed. Furthermore, the above quinoxaline derivative can be used for a carrier transporting layer because the quinoxaline derivative can transport carriers. The above quinoxaline derivative has high singlet excitation energy because $Ar^1$ and $Ar^2$ are not condensed rings. Thus, it is preferred that, in a light-emitting element, the quinoxaline derivative be used as a material in which a light-emitting substance is dispersed, or for a layer in contact with a layer containing a light-emitting substance. That is, the quinoxaline derivative of the present invention can contact with a light-emitting substance. In particular, the quinoxaline derivative can contact with a substance that exhibits fluorescence (hereinafter, referred to as a fluorescent substance) because of the high singlet excitation energy. Since the quinoxaline derivative of the present invention has high singlet excitation energy, the quinoxaline derivative can prevent quenching of emission from a fluorescent substance even when this quinoxaline derivative contacts with a fluorescent substance emitting fluorescence at a relatively short wavelength because of the high singlet excitation energy.

In the above quinoxaline derivative, it is preferable that each of $\alpha^1$ and $R^{11}$ to $R^{15}$ not be a condensed ring in view of triplet excitation energy. In other words, it is preferable that the quinoxaline derivative represented by the general formula (1) be a quinoxaline derivative in which each of $\alpha^1$ and $R^{11}$ to $R^{15}$ is not a condensed ring.

Therefore, another aspect of the present invention is a quinoxaline derivative represented by the following general formula (2).

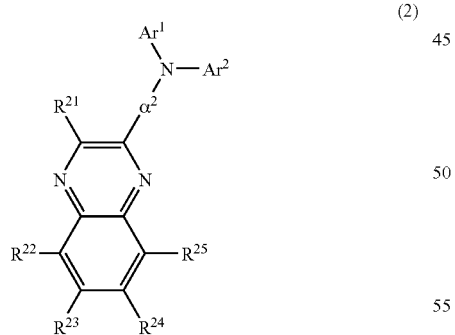

(2)

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^2$ represents an arylene group having 6 to 25 carbon atoms, which is not a condensed ring; and $R^{21}$ to $R^{25}$ may be the same or different from one another, and each of them represents any one of a hydrogen atom, an alkyl group having 1 to 4 carbon atoms, and a substituted or unsubstituted aryl group having 6 to 25 carbon atoms, which is not a condensed ring.

In the general formula (2), a quinoxaline derivative having high triplet excitation energy can be obtained when $\alpha^2$ and $R^{21}$ to $R^{25}$ are not condensed rings. Accordingly, it is preferred that, in a light-emitting element, the quinoxaline derivative be used as a material in which a substance that exhibits phosphorescence (hereinafter, referred to as a phosphorescent substance) is dispersed, or for a layer in contact with a layer containing a phosphorescent substance. That is, the quinoxaline derivative of the present invention can contact with a phosphorescent substance. The quinoxaline derivative can prevent quenching of emission from a phosphorescent substance even when this quinoxaline derivative contacts with a phosphorescent substance emitting phosphorescence at a relatively short wavelength because of the high triplet excitation energy.

Specific examples of an aryl group that is not a condensed ring include a substituted or unsubstituted phenyl group, a substituted or unsubstituted biphenyl group, and a substituted or unsubstituted fluorene group. Specific examples of an arylene group that is not a condensed ring include a phenylene group, a biphenyl-diyl group, and a fluorene-diyl group.

Therefore, another aspect of the present invention is a quinoxaline derivative represented by the following general formula (3).

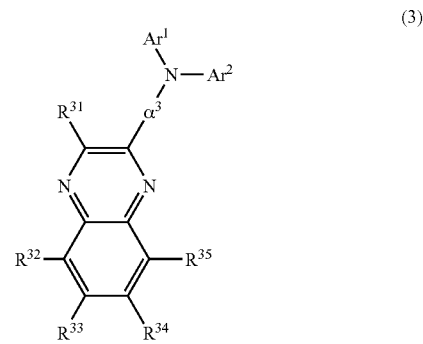

(3)

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^3$ represents any one of a phenylene group, a biphenyl-diyl group, and a fluorene-diyl group; and $R^{31}$ to $R^{35}$ may be the same or different from one another, and each of them represents any one of a hydrogen atom, an alkyl group having 1 to 4 carbon atoms, a substituted or unsubstituted phenyl group, a substituted or unsubstituted biphenyl group, and a substituted or unsubstituted fluorene group.

In a general formula (3), it is preferable that $\alpha^3$ be one of a phenylene group and a biphenyl-diyl group in terms of synthesis. Further, it is preferable that each of $R^{31}$ to $R^{35}$ be any one of a hydrogen atom, an alkyl group having 1 to 4 carbon atoms, a substituted or unsubstituted phenyl group, and a substituted or unsubstituted biphenyl group in term of synthesis.

Therefore, another aspect of the present invention is a quinoxaline derivative represented by the following general formula (4).

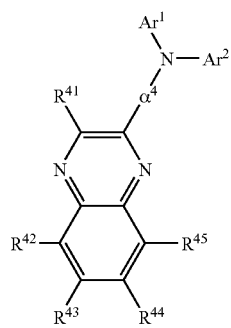

(4)

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^4$ represents one of a phenylene group and a biphenyl-diyl group; and $R^{41}$ to $R^{45}$ may be the same or different from one another, and each of them represents any one of a hydrogen atom, an alkyl group having 1 to 4 carbon atoms, a substituted or unsubstituted phenyl group, and a substituted or unsubstituted biphenyl group.

Another aspect of the present invention is a quinoxaline derivative represented by the following general formula (5).

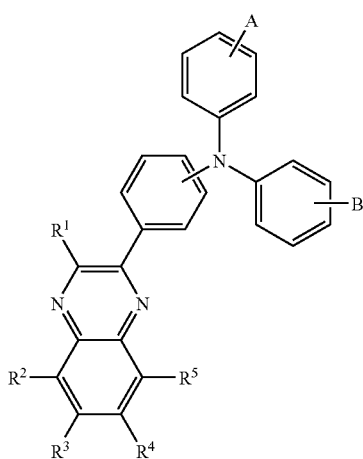

(5)

In the formula, A and B may be the same or different from one another, and each represents one of hydrogen and a phenyl group; and $R^1$ to $R^5$ may be the same or different from one another, and each represents any one of a hydrogen atom, an alkyl group having 1 to 4 carbon atoms, a substituted or unsubstituted phenyl group, and a substituted or unsubstituted biphenyl group.

Another aspect of the present invention is a quinoxaline derivative represented by the following general formula (6).

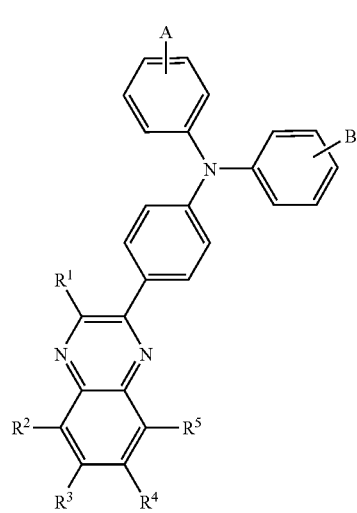

(6)

In the formula, A and B may be the same or different from one another, and each represents one of hydrogen and a phenyl group; and $R^1$ to $R^5$ may be the same or different from one another, and each represents any one of a hydrogen atom, an alkyl group having 1 to 4 carbon atoms, a substituted or unsubstituted phenyl group, and a substituted or unsubstituted biphenyl group.

In the above general formula (6), it is preferable that each of $R^2$ to $R^5$ be a hydrogen atom in view of synthesis.

Therefore, another aspect of the present invention is a quinoxaline derivative represented by the following general formula (7).

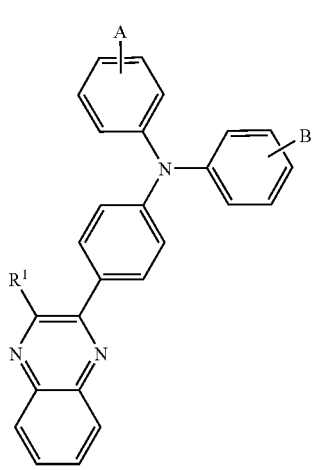

(7)

In the formula, A and B may be the same or different from one another, and each represents one of hydrogen and a phenyl group; and $R^1$ represents any one of a substituted or unsubstituted phenyl group and a substituted or unsubstituted biphenyl group.

Another aspect of the present invention is a quinoxaline derivative represented by a structural formula (102).

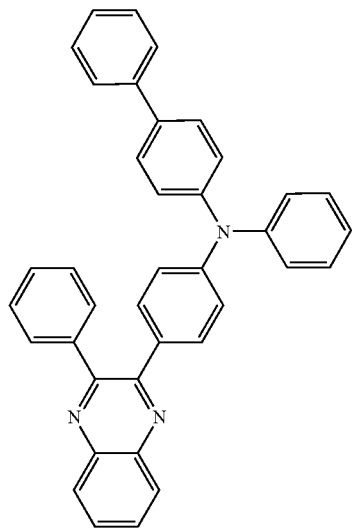

(102)

Another aspect of the present invention is a quinoxaline derivative represented by a structural formula (105).

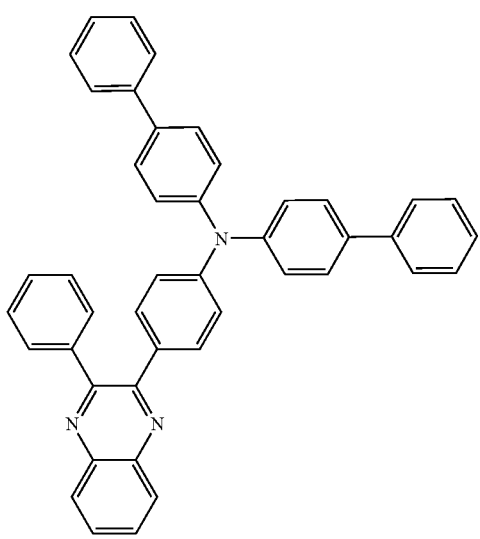

(105)

Another aspect of the present invention is a light-emitting element including any of the above-described quinoxaline derivatives, specifically, a light-emitting element containing any of the above-described quinoxaline derivatives between a pair of electrodes.

Another aspect of the present invention is a light-emitting element including a light-emitting layer between a pair of electrodes, and the light-emitting layer contains any of the above-described quinoxaline derivatives.

Another aspect of the present invention is a light-emitting element including a light-emitting layer between a pair of electrodes, and the light-emitting layer contains any of the above-described quinoxaline derivatives and a fluorescent substance.

Another aspect of the present invention is a light-emitting element including a light-emitting layer between a pair of electrodes, and the light-emitting layer contains any of the above-described quinoxaline derivatives and a phosphorescent substance. Another aspect of the present invention is a light-emitting device including a light-emitting element that includes an EL layer between a pair of electrodes and any of the above-described quinoxaline derivatives in the EL layer, and a control unit to control light emission from the light-emitting element. A category of the light-emitting device in this specification includes image display devices and light sources (e.g., lighting devices). Further, the category of the light-emitting device also includes modules in each of which a connector such as a flexible printed circuit (FPC), a tape automated bonding (TAB) tape, or a tape carrier package (TCP) is attached to a panel; modules in each of which a printed wiring board is provided at an end of a TAB tape or a TCP; and modules in each of which an integrated circuit (IC) is directly mounted on the light-emitting element by a chip on glass (COG) method.

Further, the present invention also covers an electronic device using the light-emitting element of the present invention for its display portion. Therefore, another aspect of the present invention is the electronic device including a display portion, and the display portion includes the above-described light-emitting element and the control unit to control light emission from the light-emitting element.

The quinoxaline derivatives of the present invention are bipolar and have both excellent electron-transporting properties and hole-transporting properties. Furthermore, the quinoxaline derivatives of the present invention are stable to electrochemical oxidation and reduction.

The quinoxaline derivatives of the present invention are bipolar; therefore, by using any of the quinoxaline derivatives of the present invention, a light-emitting element and light-emitting device with a low driving voltage and low power consumption can be obtained.

Furthermore, an electronic device with low power consumption can be obtained by using any of the quinoxaline derivatives of the present invention.

BRIEF DESCRIPTION OF THE DRAWINGS

In the accompanying drawings:

FIGS. 5A and 5B are views each illustrating a light-emitting device of the present invention;

DETAILED DESCRIPTION OF THE INVENTION

Figure 1A:
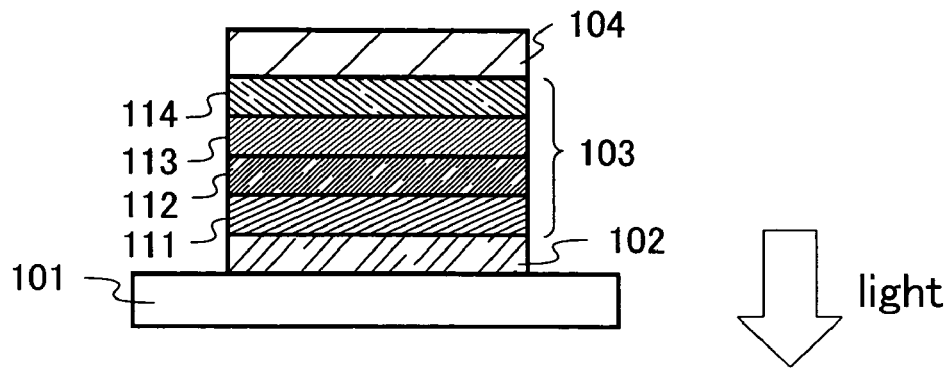
FIGS. 1A to 1C are views each illustrating a light-emitting element of the present invention.

Embodiment modes of the present invention are described in detail with reference to the accompanying drawings. It is to be noted that the present invention is not limited to the following description, and it is easily understood by those skilled in the art that modes and details thereof can be modified in various ways without departing from the spirit and the scope of the present invention. Therefore, the present invention should not be interpreted as being limited to the following description of the embodiment modes.

(Embodiment Mode 1)

The quinoxaline derivative of the present invention is represented by the following general formula (1).

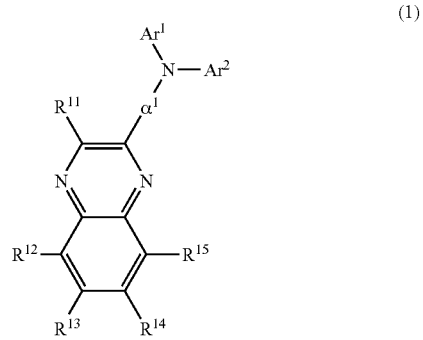

(1)

In the formula, Ar$^1$ and Ar$^2$ may be the same or different from one another and may be combined with one another, and each represents any one of a substituted or unsubstituted phenyl group, a substituted or unsubstituted biphenyl group, and a substituted or unsubstituted terphenyl group; α$^1$ represents an arylene group having 6 to 25 carbon atoms; and R$^{11}$ to R$^{15}$ may be the same or different from one another, and each of them represents any one of a hydrogen atom, an alkyl group having 1 to 4 carbon atoms, and a substituted or unsubstituted aryl group having 6 to 25 carbon atoms.

As the substituted or unsubstituted phenyl group, the substituted or unsubstituted biphenyl group, or the substituted or unsubstituted terphenyl group, substituents shown in the structural formulae (11-1) to (11-13) can be used specifically. Alternatively, each of the substituents shown in the structural formulae (11-1) to (11-13) may further be substituted with an alkyl group having 1 to 4 carbon atoms, Examples of the alkyl group having 1 to 4 carbon atoms include a methyl group, an ethyl group, an isopropyl group, an n-propyl group, an isobutyl group, a sec-butyl group, an n-butyl group, and a tert-butyl group.

(11-1)

-continued
(11-2)
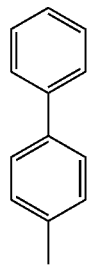
(11-3)
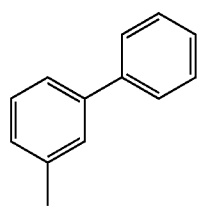
(11-4)
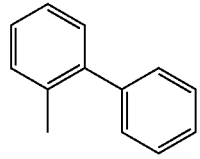
(11-5)
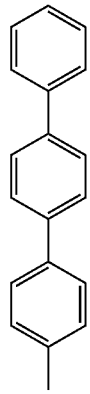
(11-6)
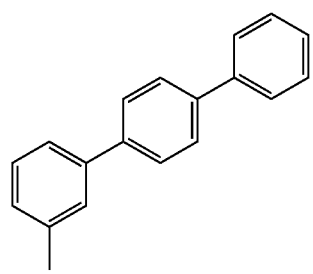
(11-7)
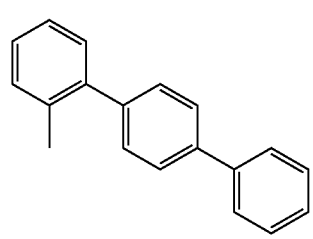
-continued
(11-8)
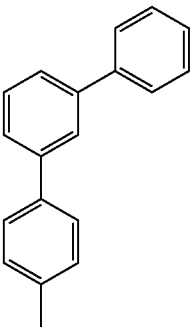
(11-9)
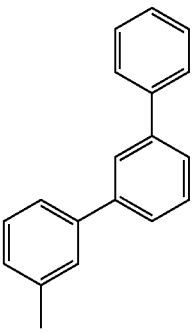
(11-10)
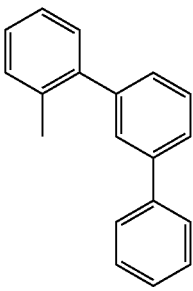
(11-11)
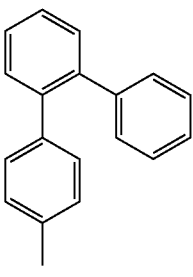
(11-12)
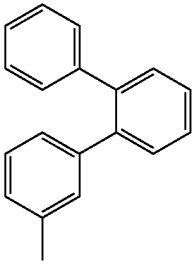

(11-13)
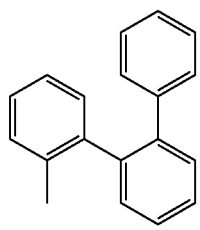
As the arylene group having 6 to 25 carbon atoms, substituents shown in structural formulae (12-1) to (12-9) can be used specifically.
(12-1)
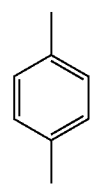
(12-2)
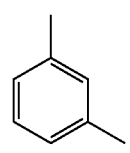
(12-3)
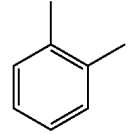
(12-4)
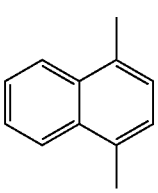
(12-5)
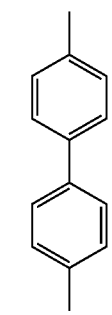
(12-6)
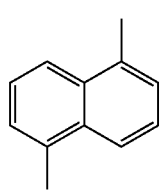
(12-7)
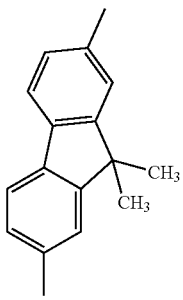
(12-8)
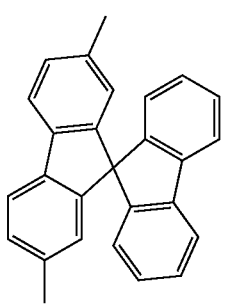
(12-9)
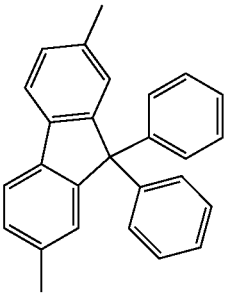
Therefore, as the amine skeleton in the general formula (1), that is, an amine group shown in a general formula (21), structures shown in structural formulae (21-1) to (21-73) can be used specifically.
(21)
(21-1)
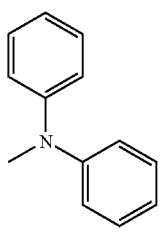

(21-2)
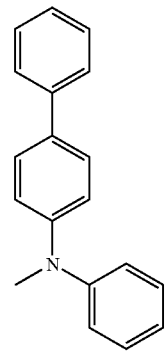
(21-3)
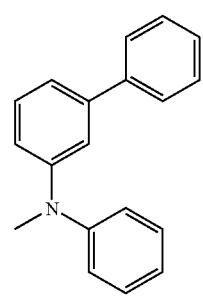
(21-4)
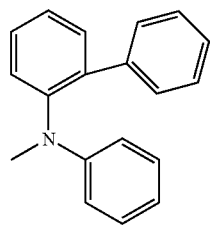
(21-5)
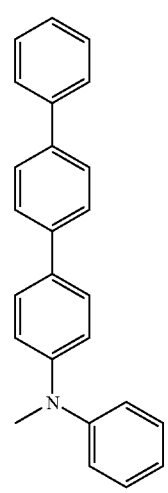
(21-6)
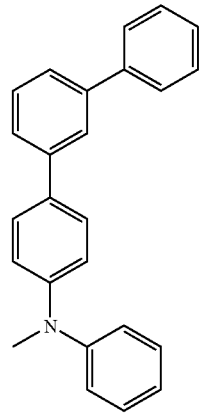
(21-7)
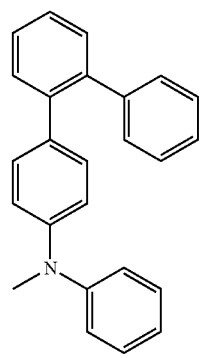
(21-8)
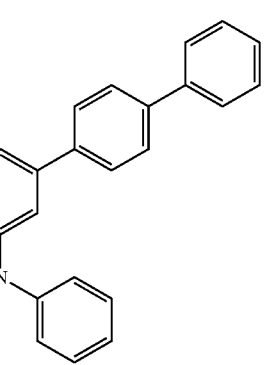
(21-9)
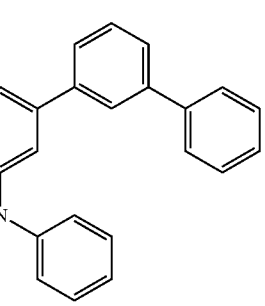

(21-10) 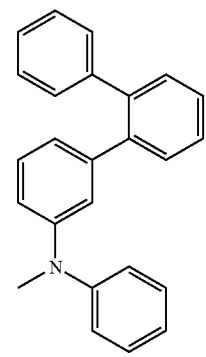
(21-11) 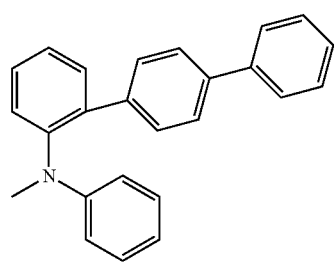
(21-12) 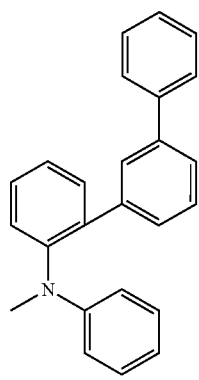
(21-13) 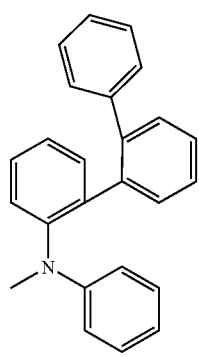
(21-14) 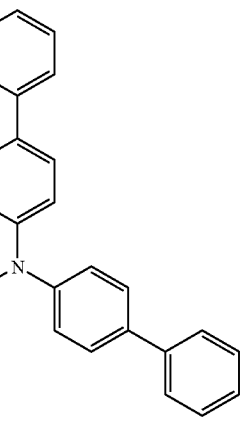
(21-15) 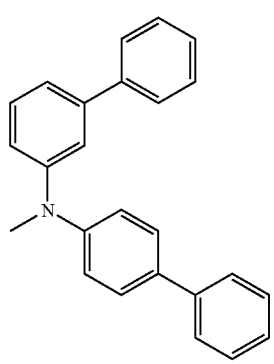
(21-16) 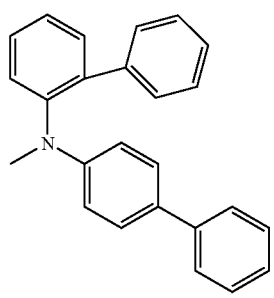
(21-17) 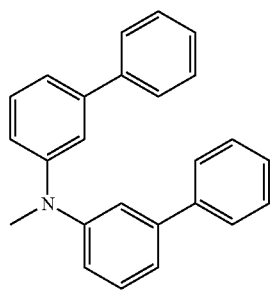

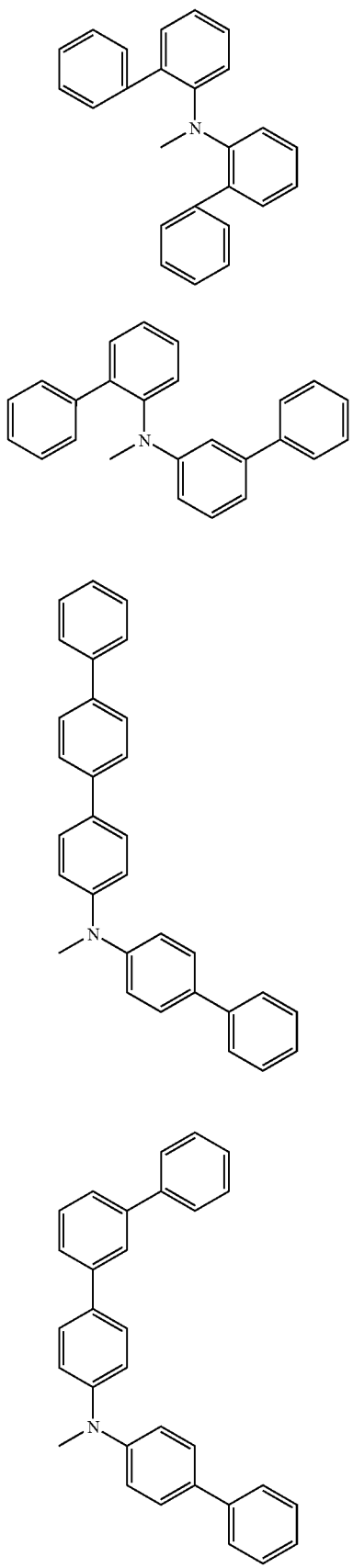
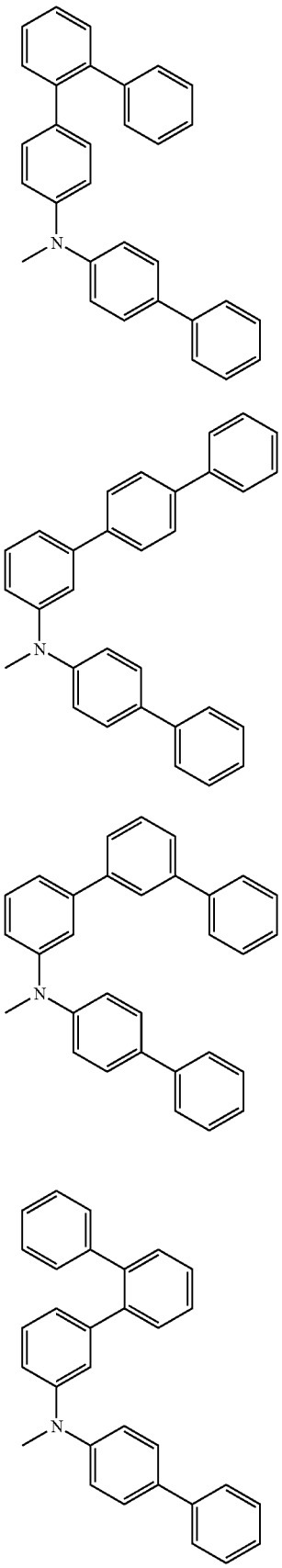

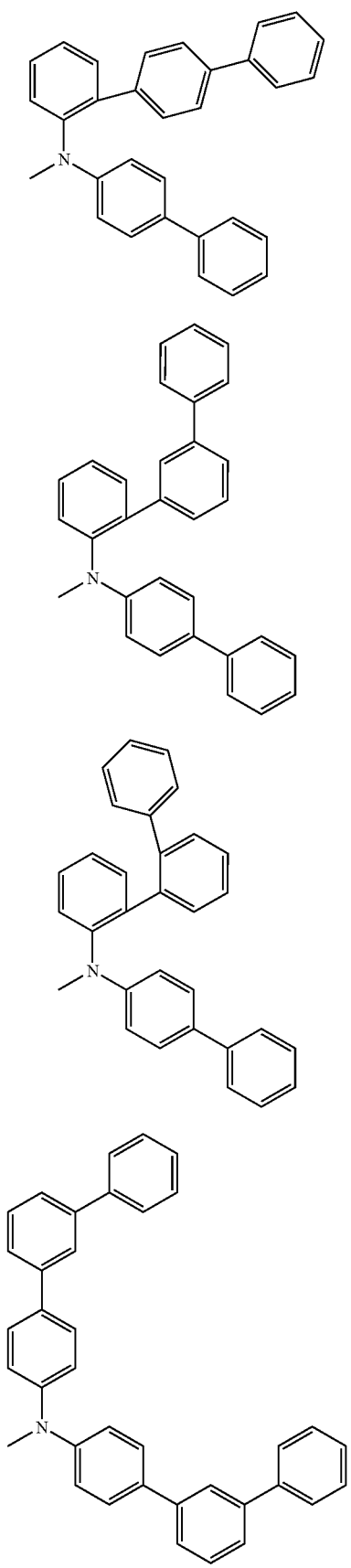

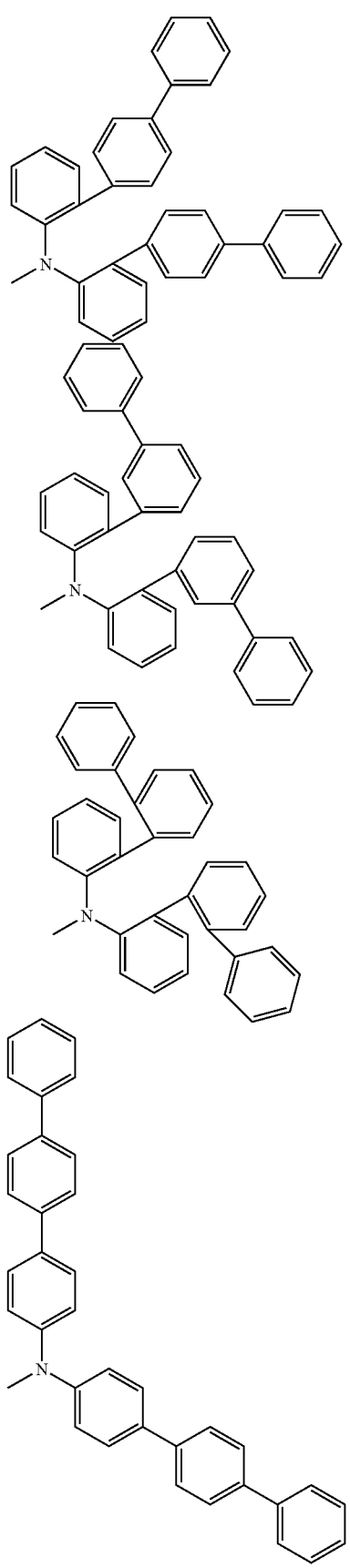
(21-34)
(21-35)
(21-36)
(21-37)
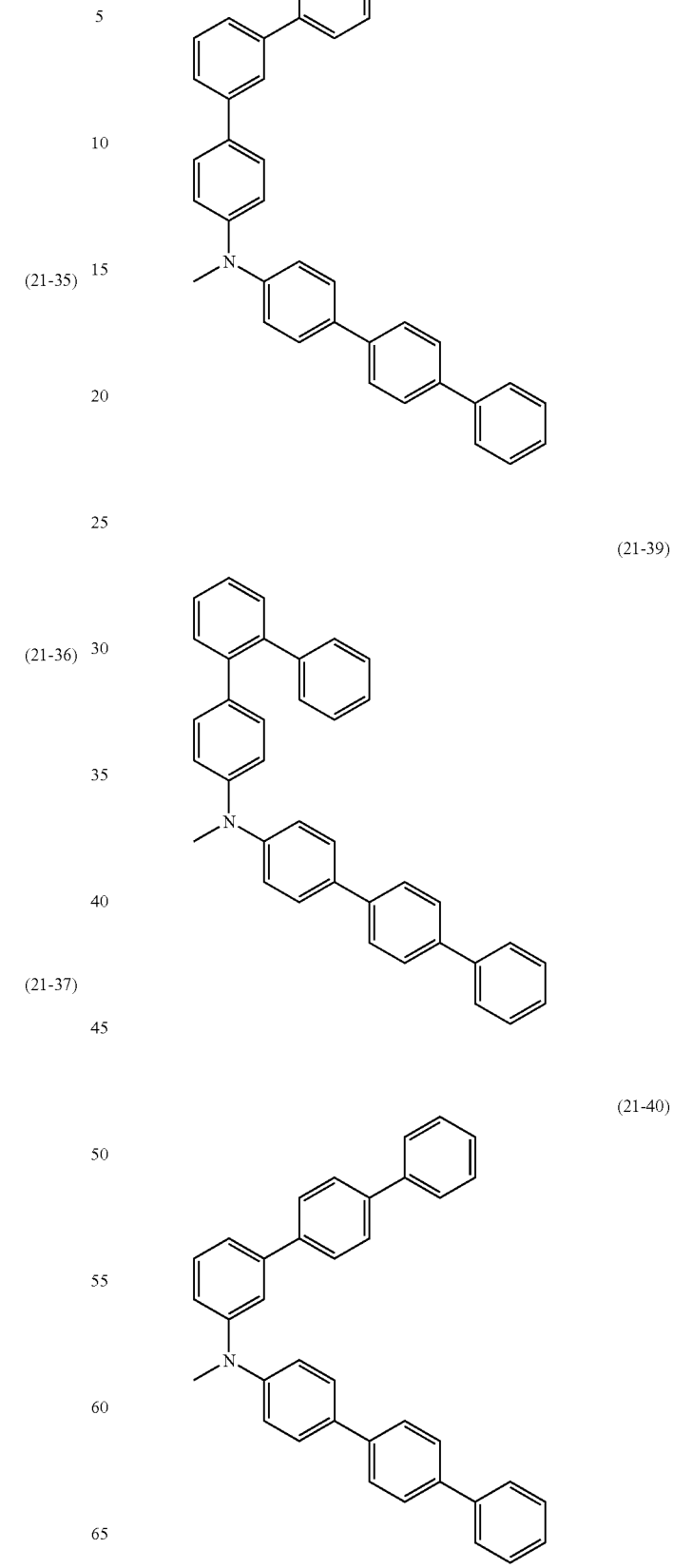
(21-38)
(21-39)
(21-40)

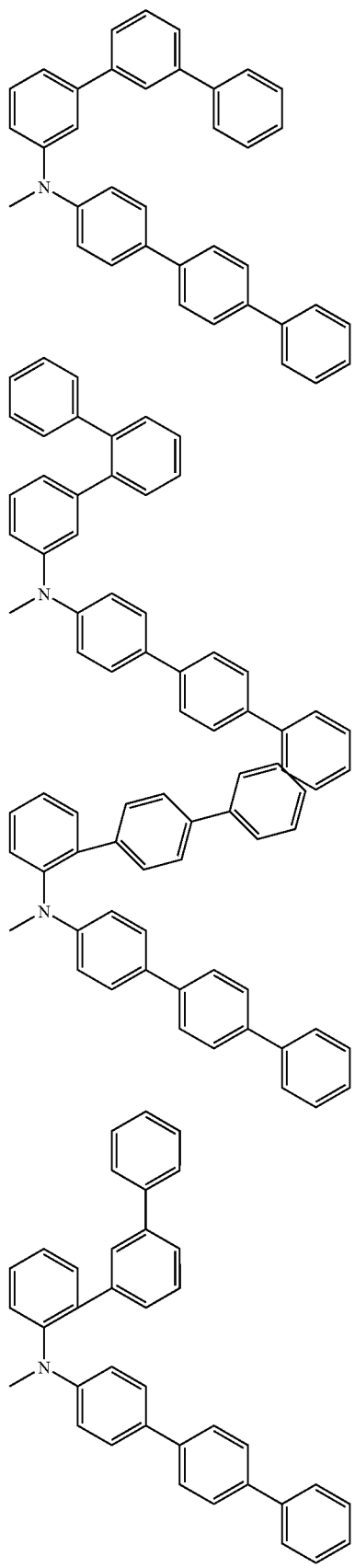
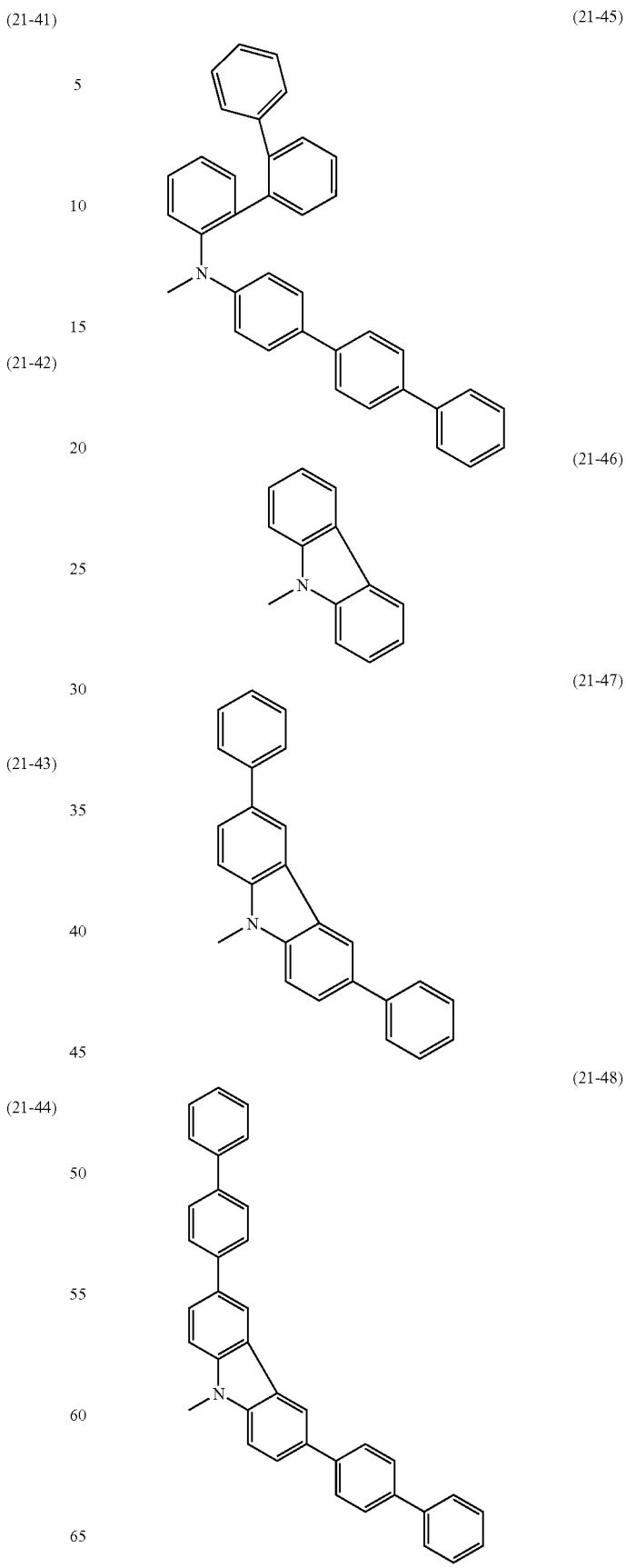

(21-49)
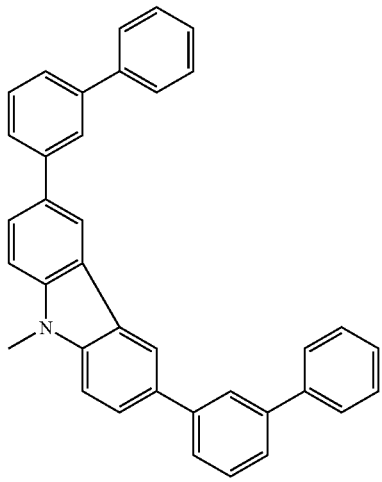
(21-50)
(21-51)
(21-52)
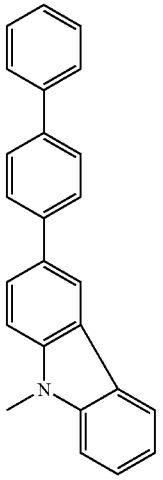
(21-53)
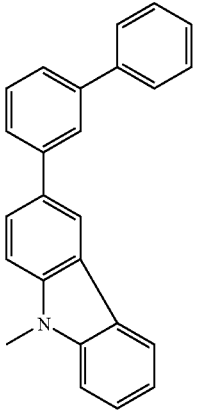
(21-54)
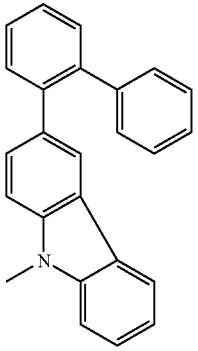
(21-55)
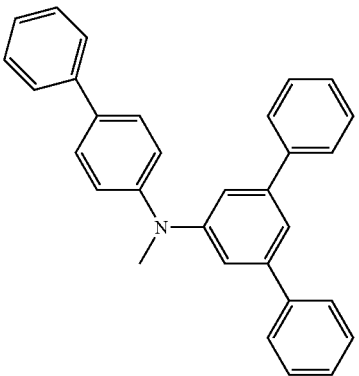

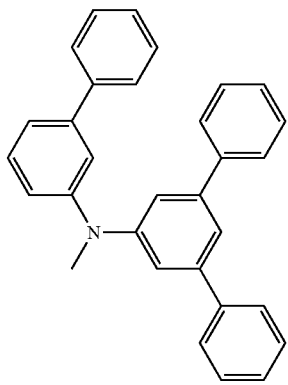
(21-56)
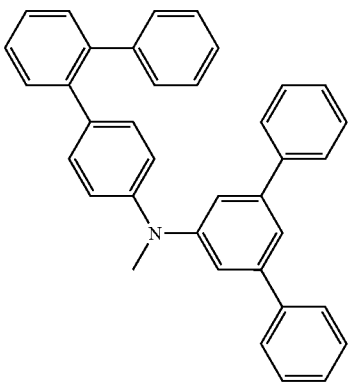
(21-60)
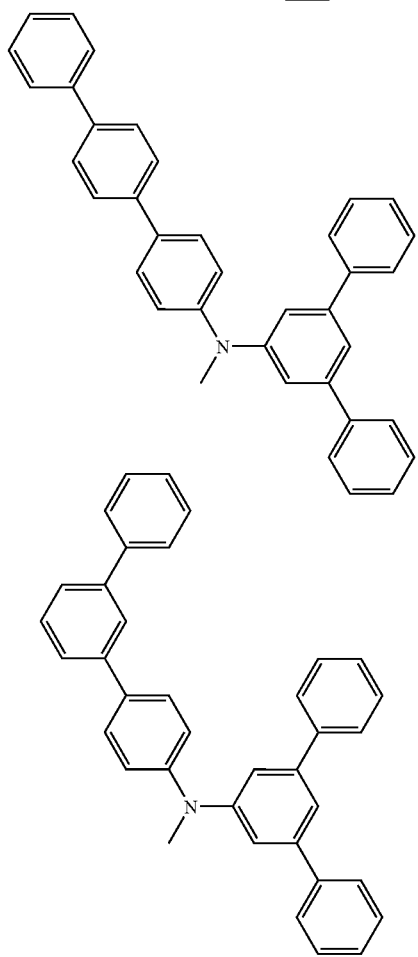
(21-57)
(21-58)
(21-59)
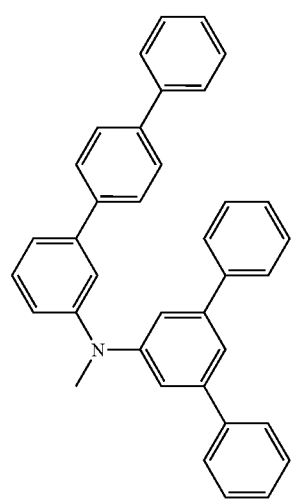
(21-61)
(21-62)

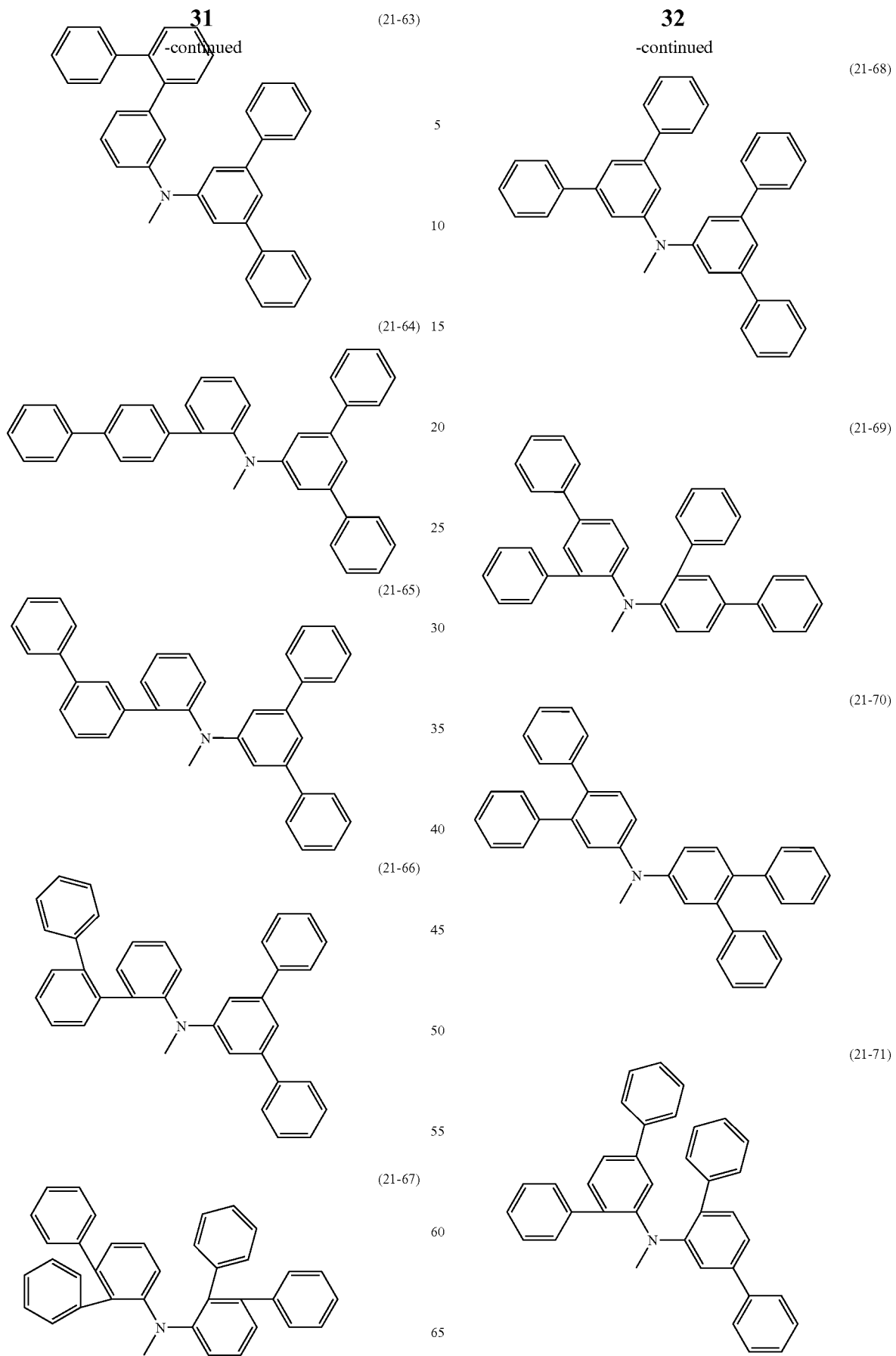

(21-72)
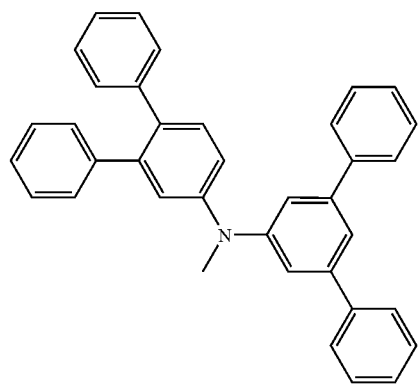
(21-73)
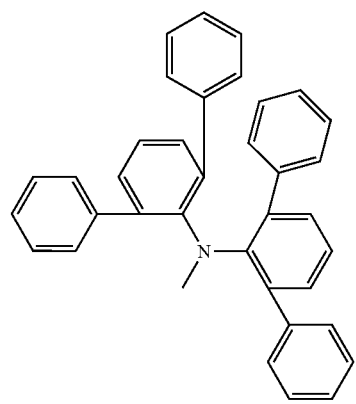
Specific examples of the quinoxaline derivatives of the present invention include quinoxaline derivatives shown in structural formulae (101) to (259); it is to be noted that the present invention is not limited to them.
(101)
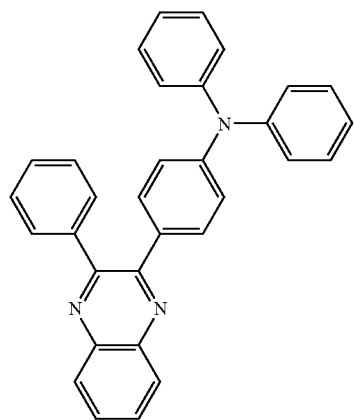
(102)
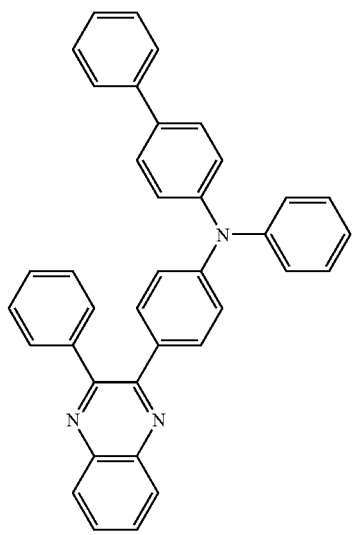
(103)
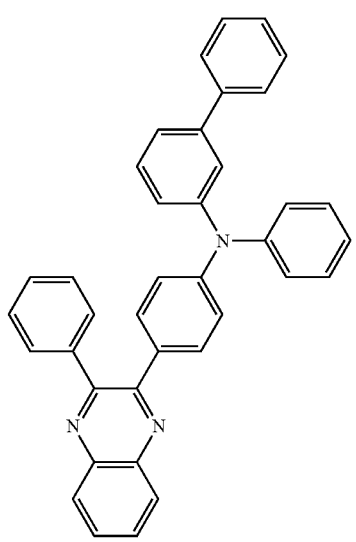
(104)
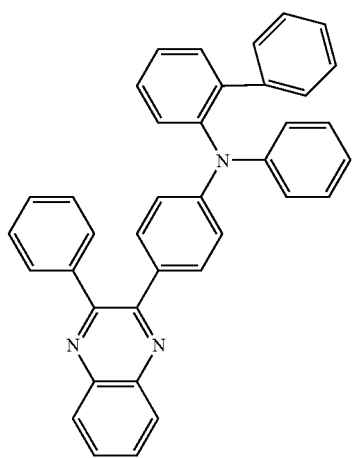

(105)
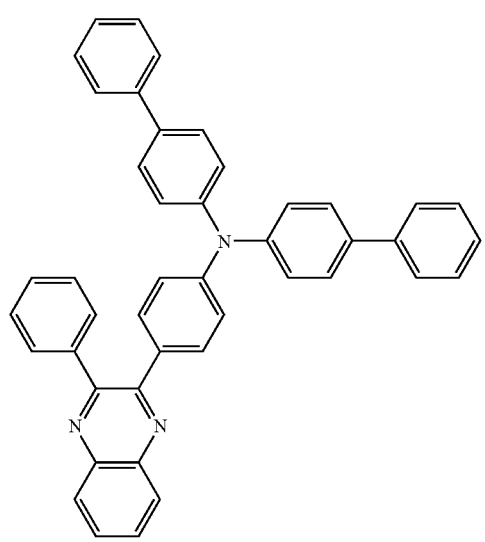
(106)
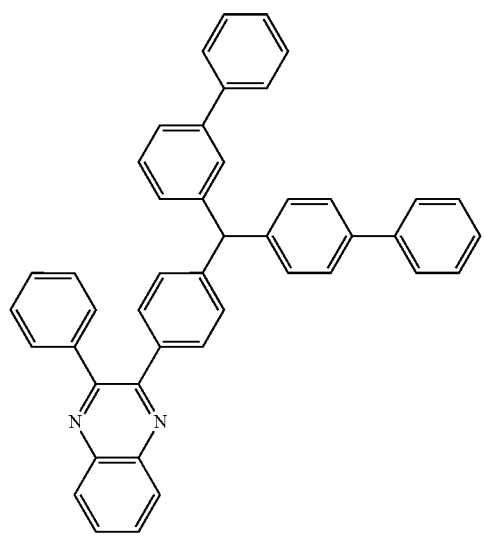
(107)
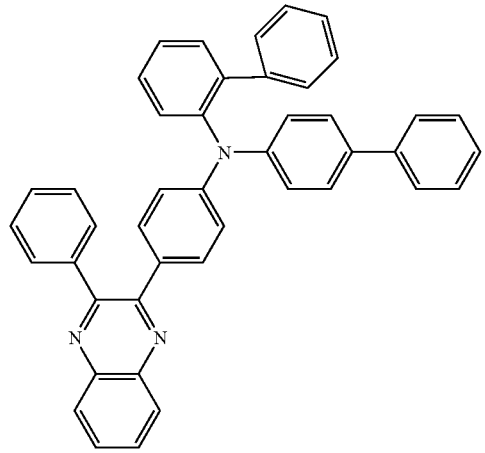
(108)
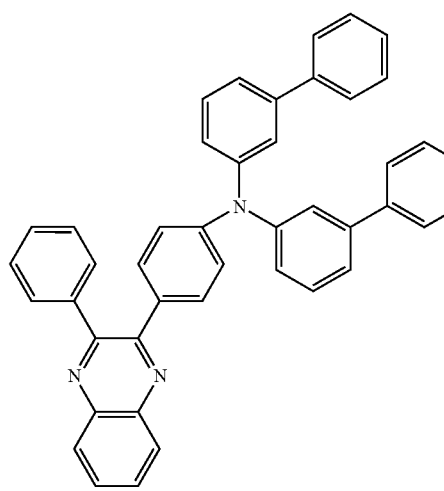
(109)
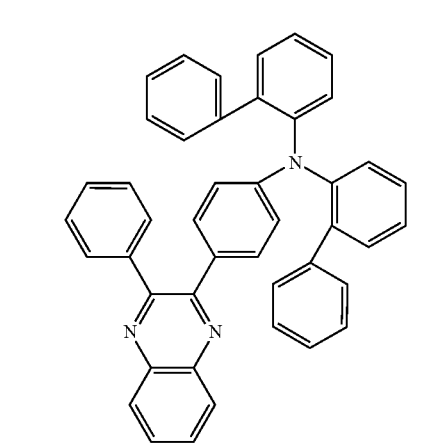
(110)
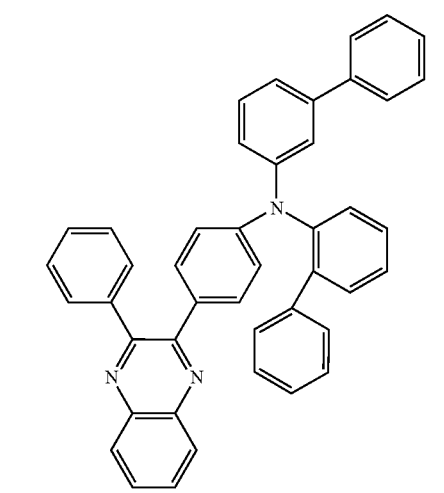

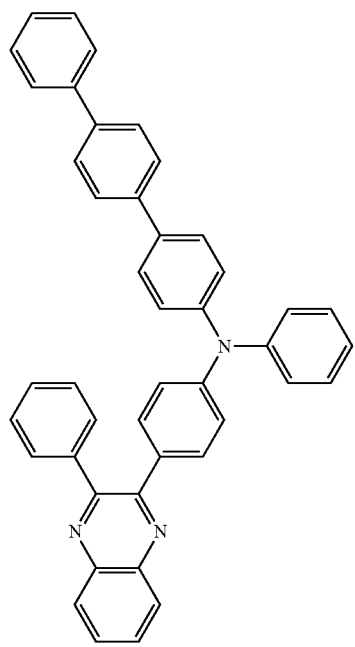
(111)
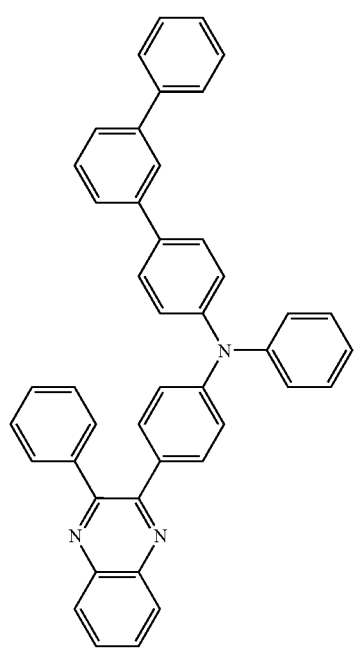
(112)
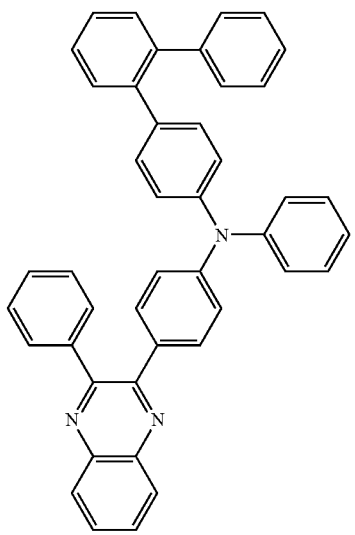
(113)
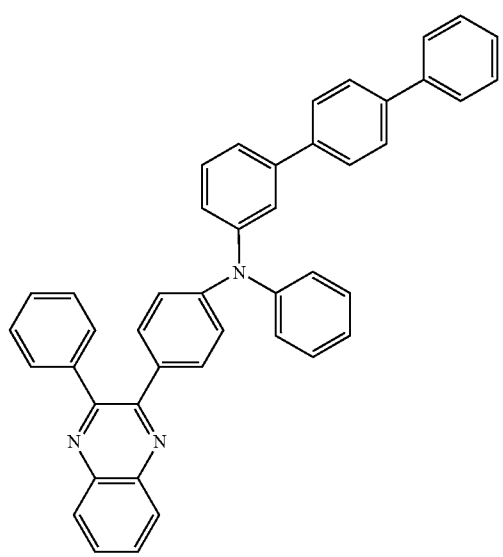
(114)
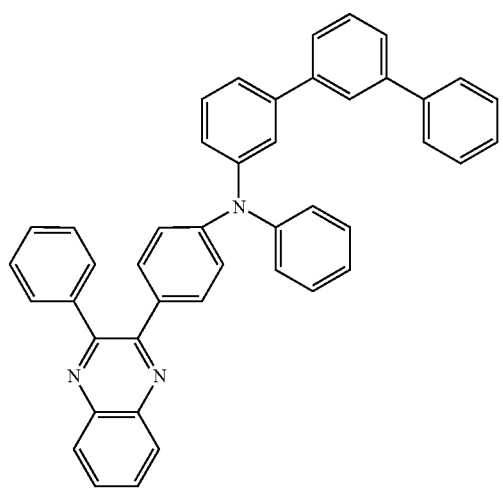
(115)

(116)
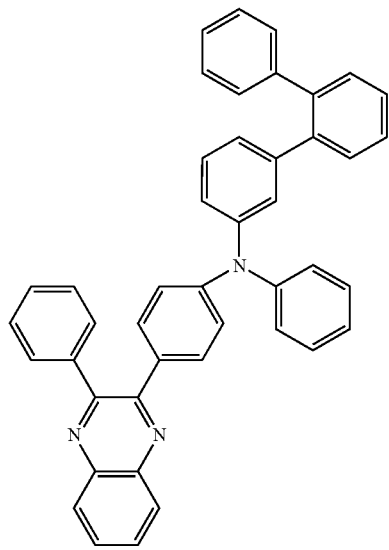
(117)
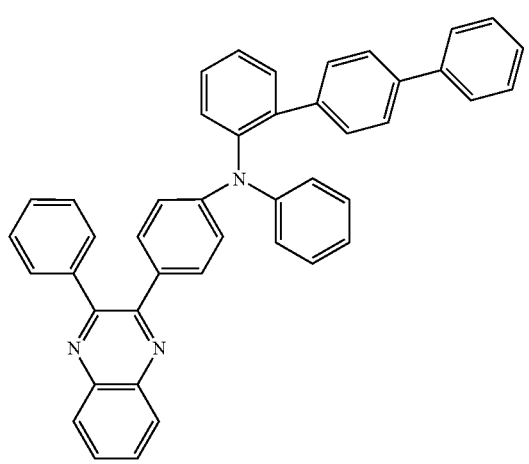
(118)
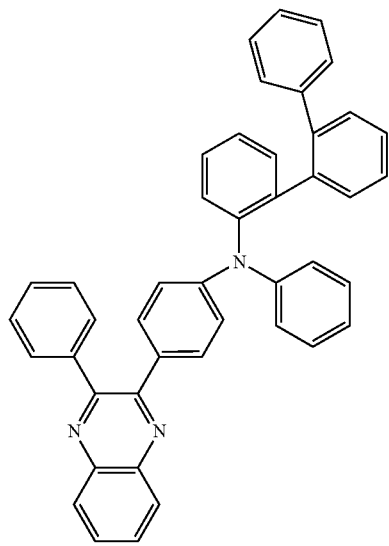
(119)
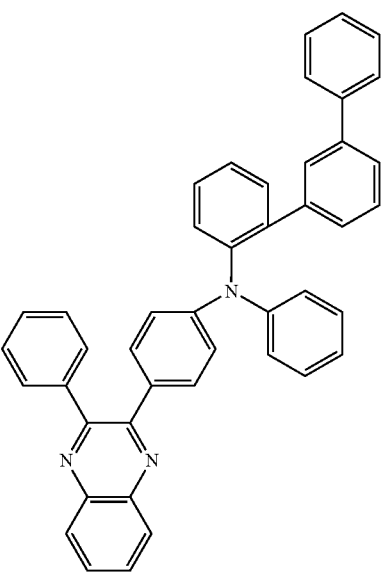
(120)
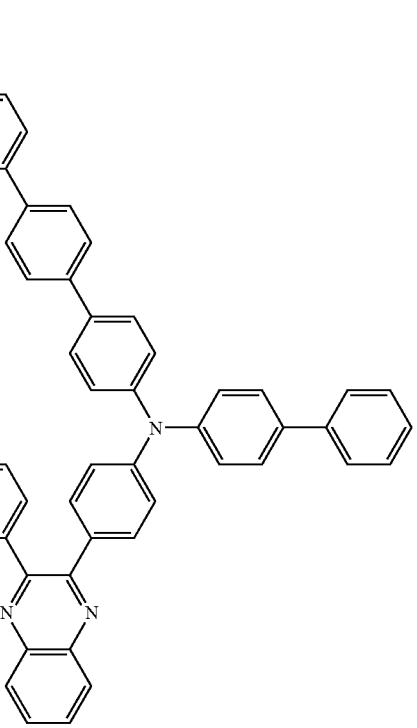

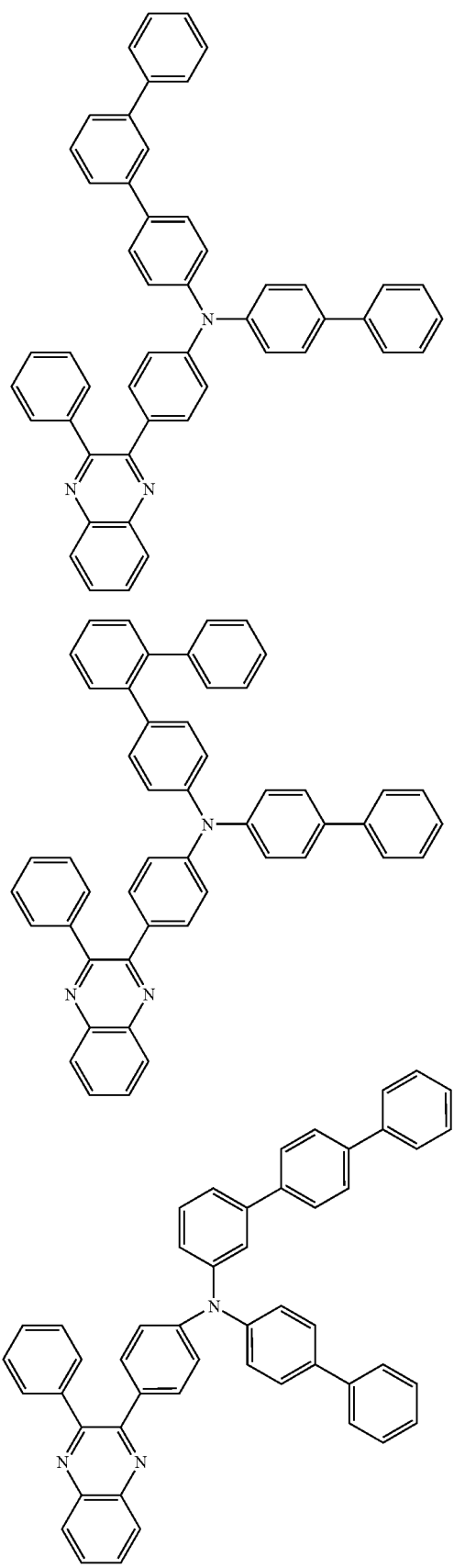
(121)
(122)
(123)
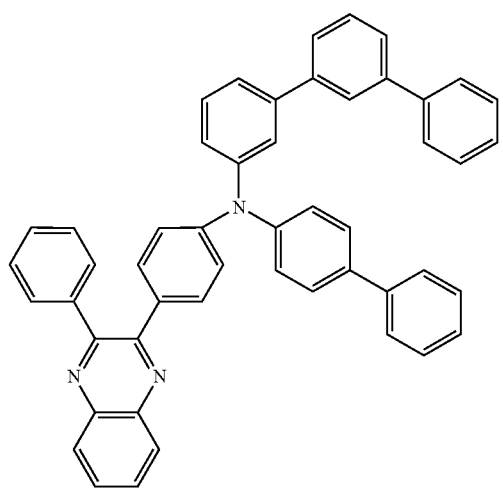
(124)
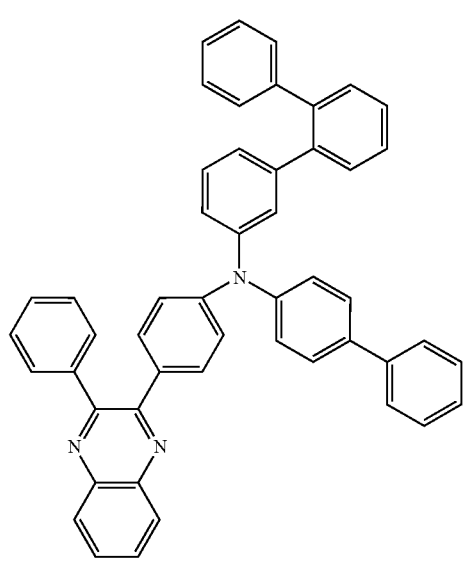
(125)
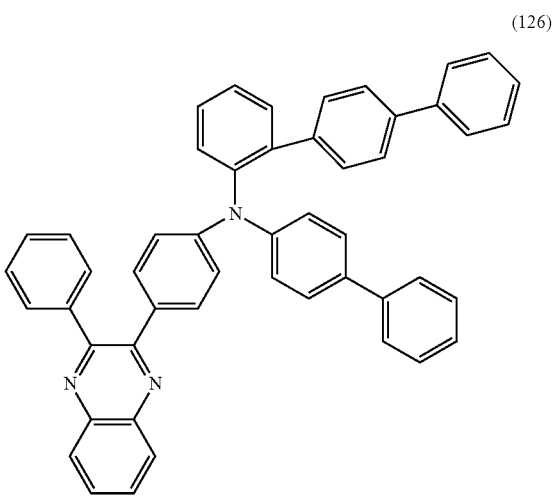
(126)

(127)
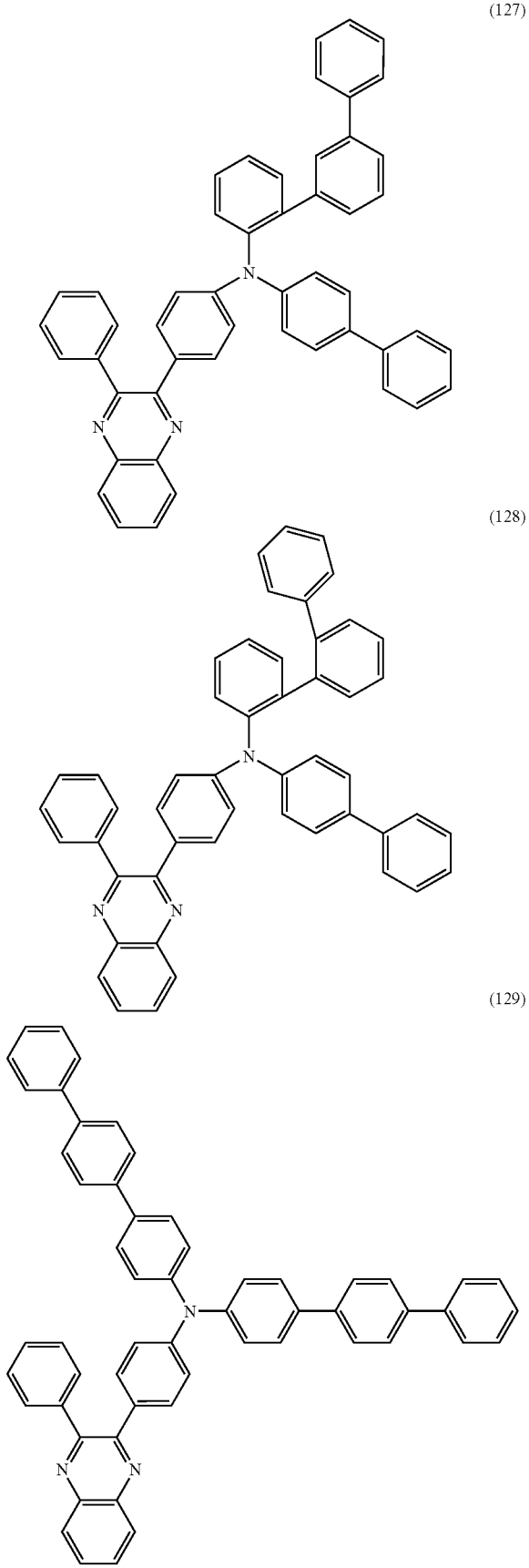
(128)
(129)
(130)
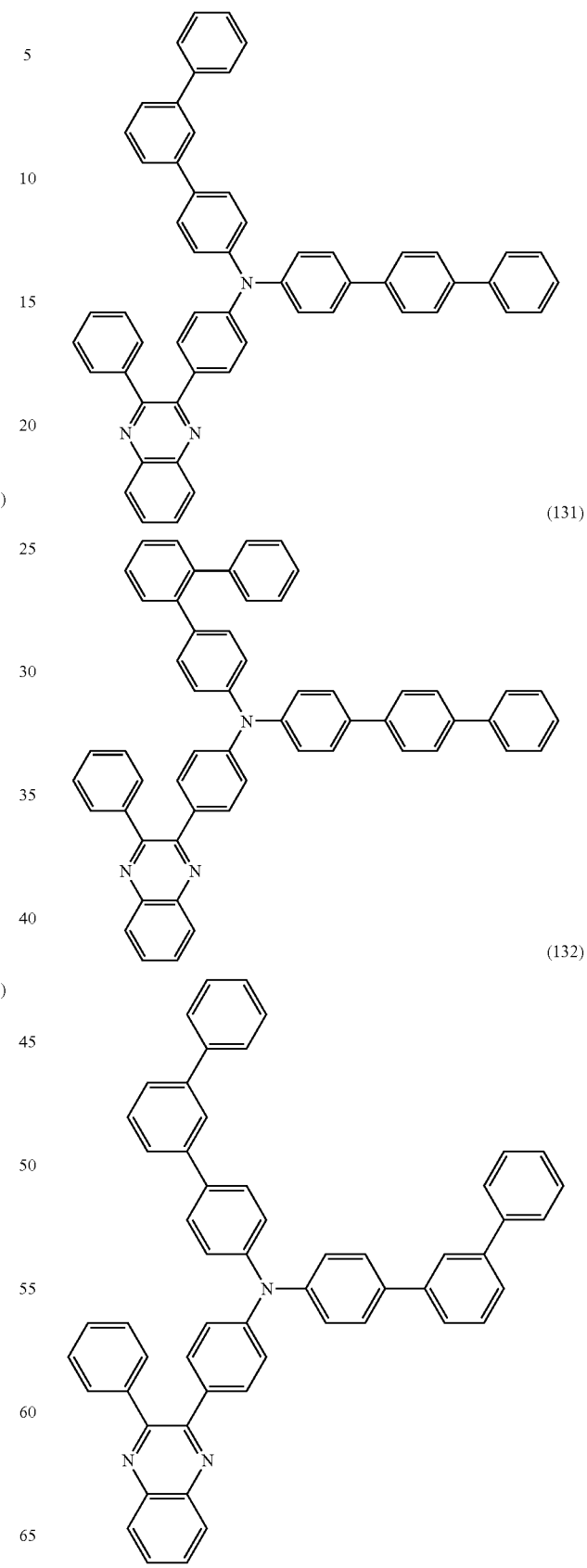
(131)
(132)

(133)
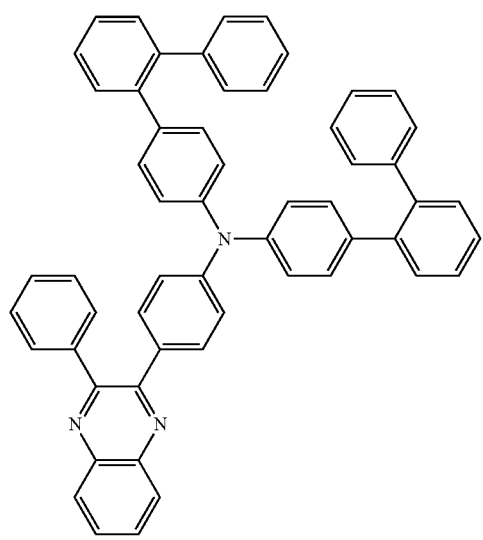
(134)
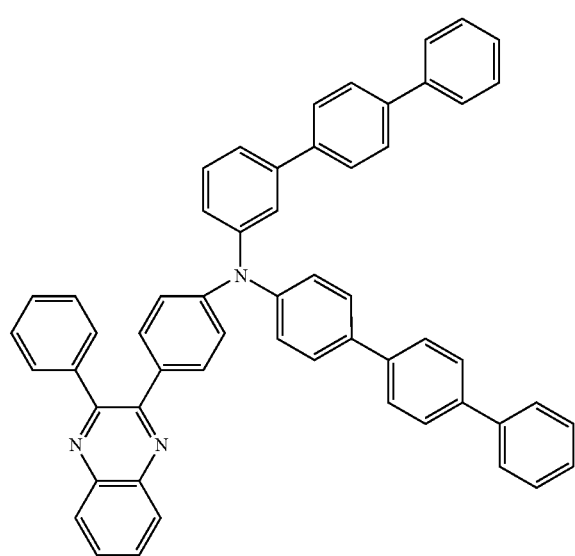
(135)
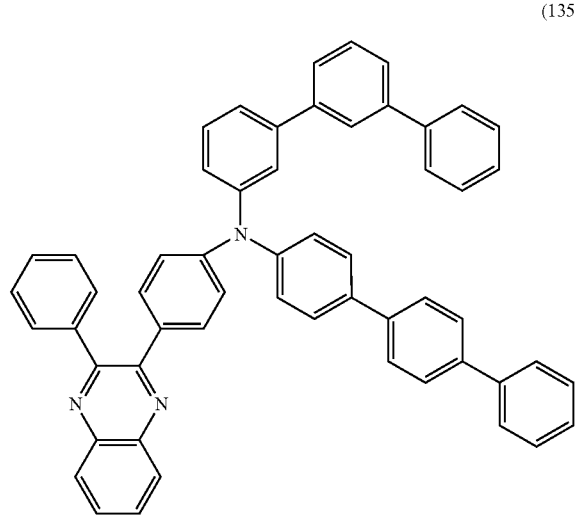
(136)
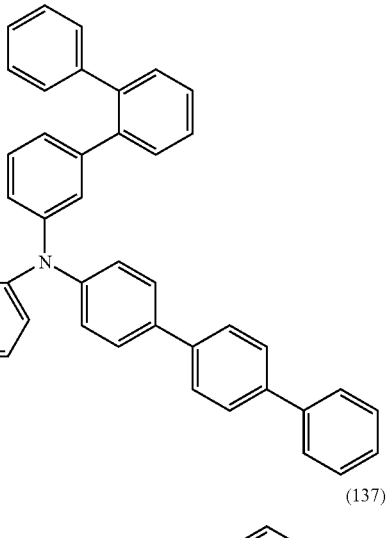
(137)
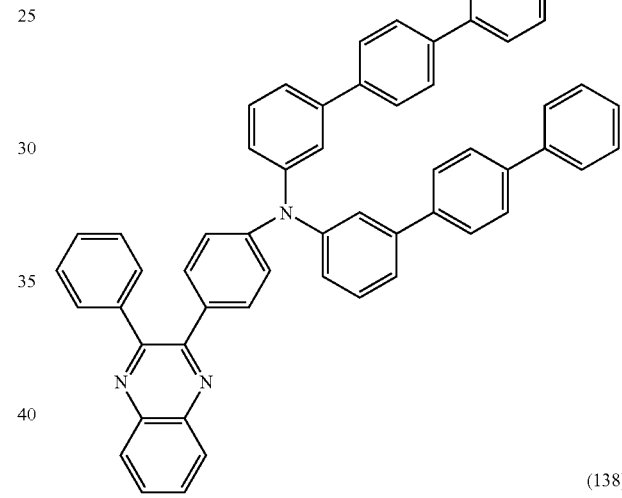
(138)
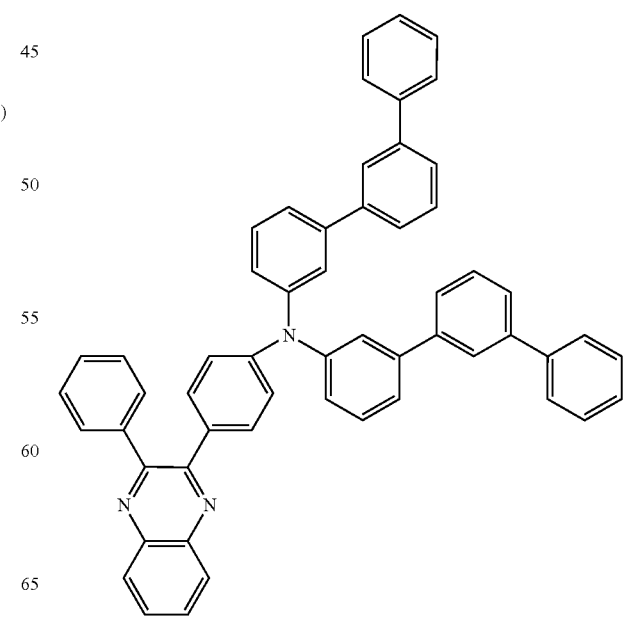

-continued
(139)
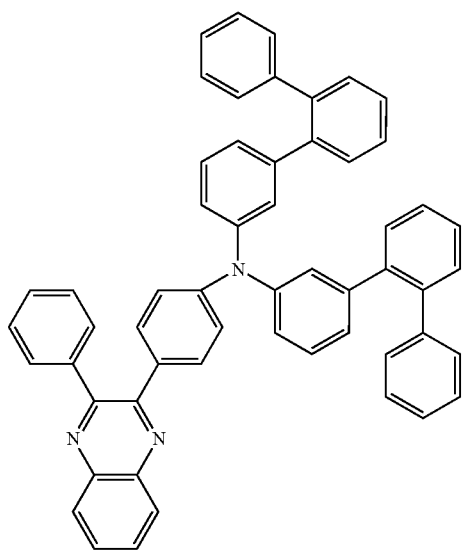
(140)
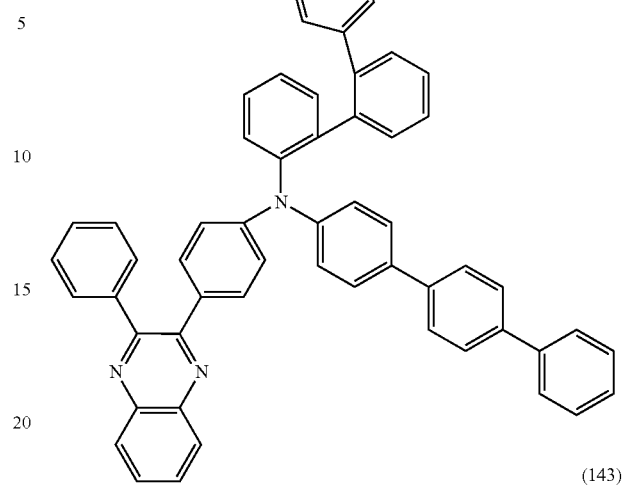
(141)
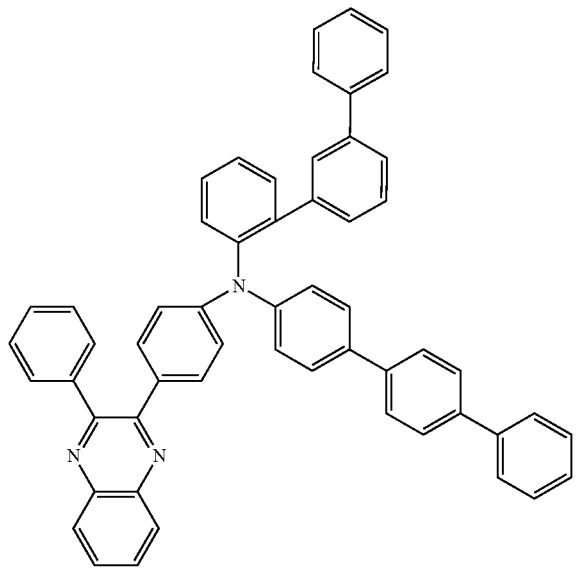
-continued
(142)
(143)
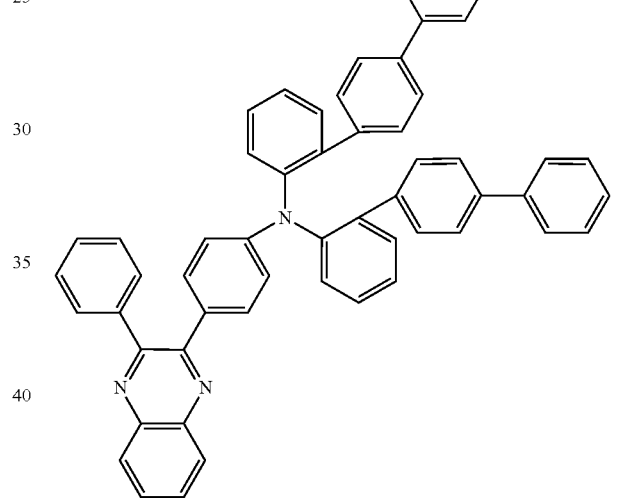
(144)

(145)
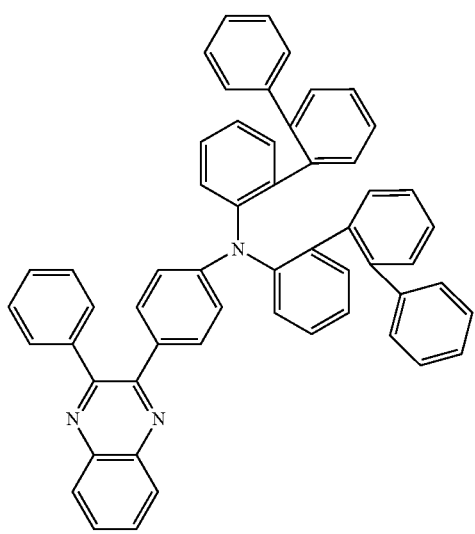
(148)
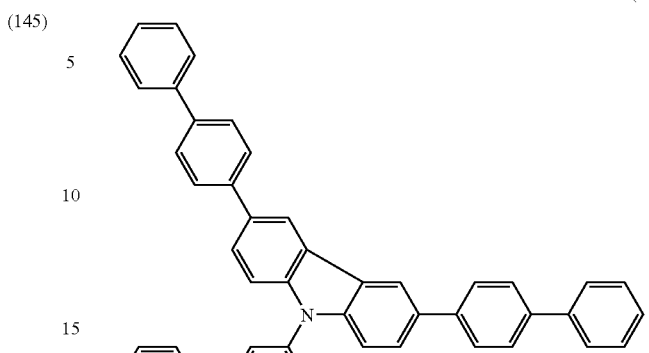
(146)
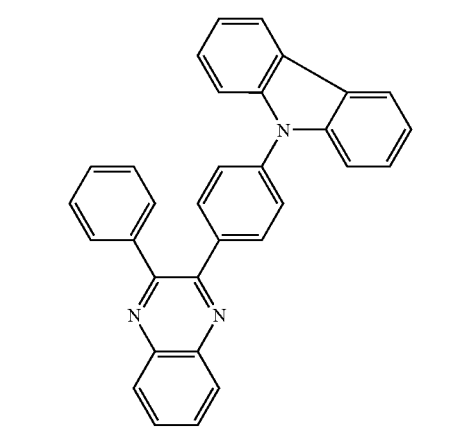
(149)
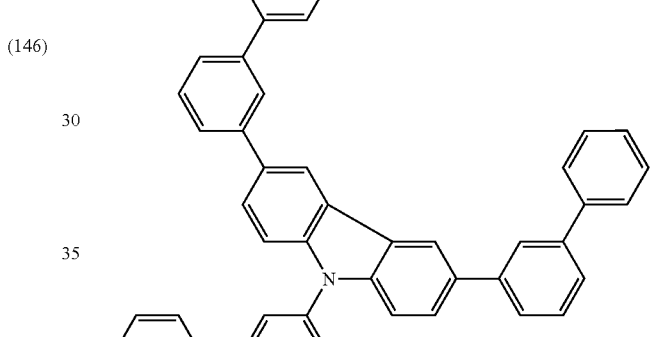
(147)
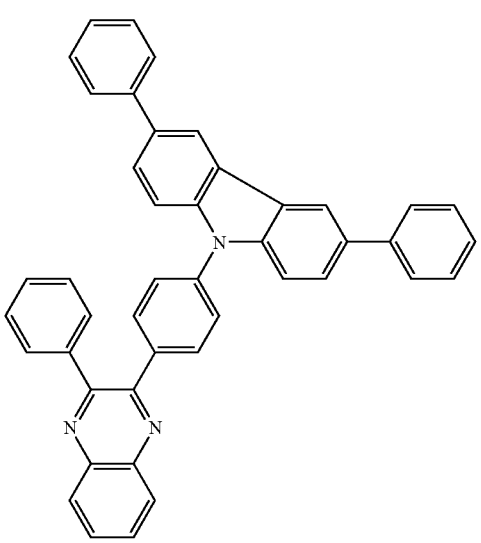
(150)
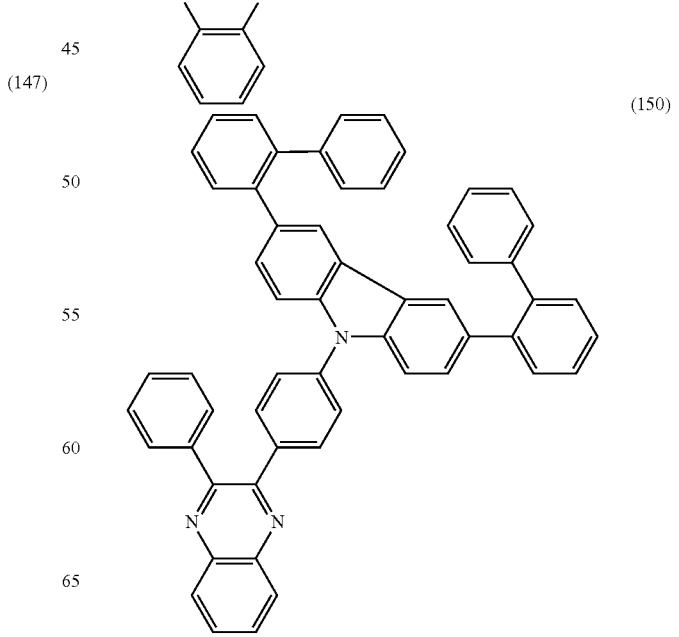

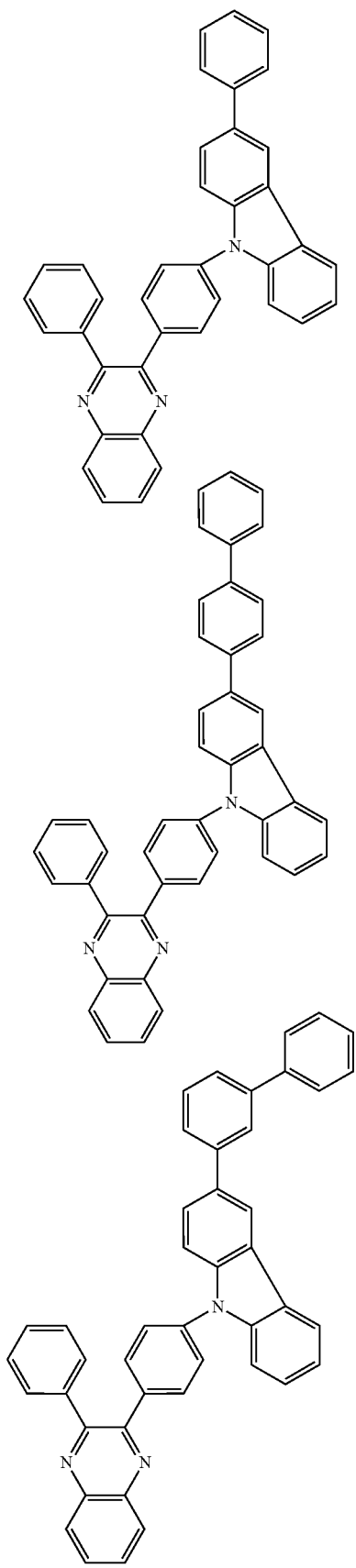
(151)
(152)
(153)
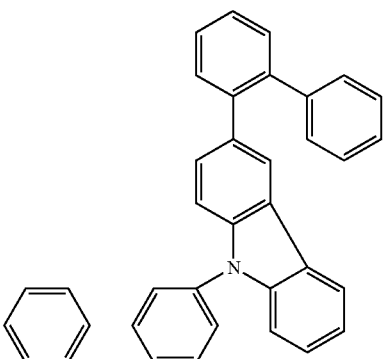
(154)
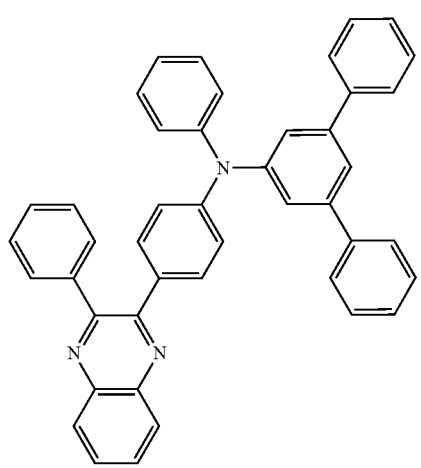
(155)
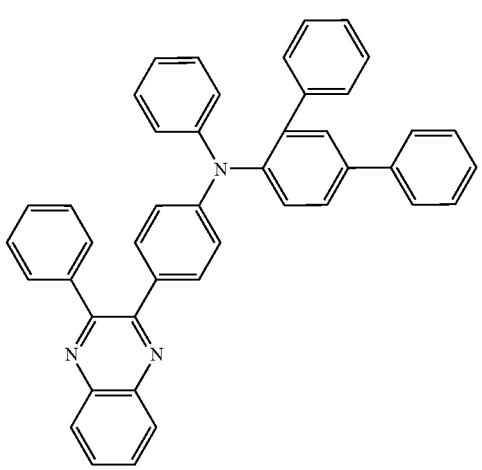
(156)

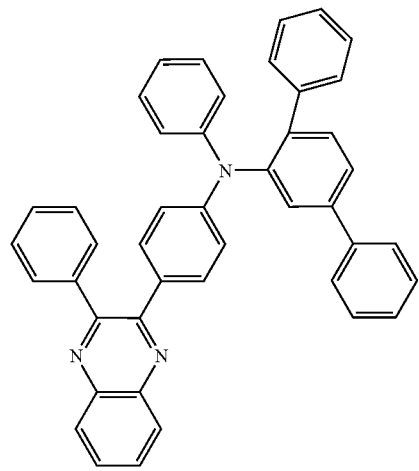
(157)
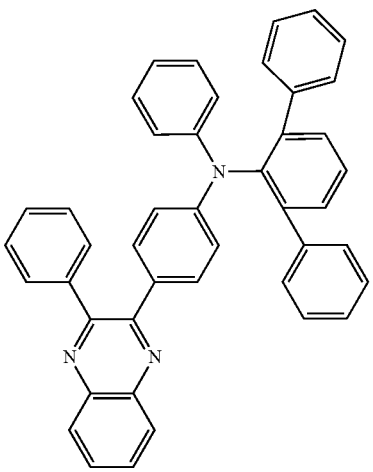
(160)
(158)
(161)
(159)
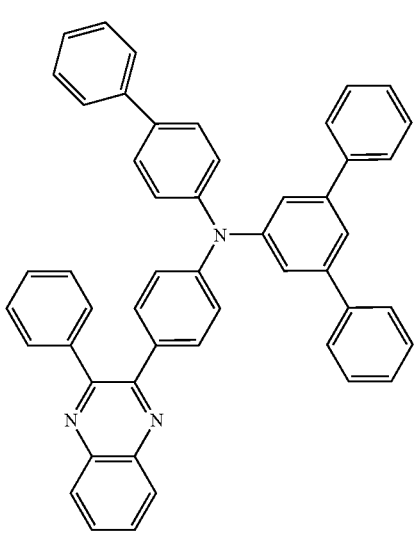
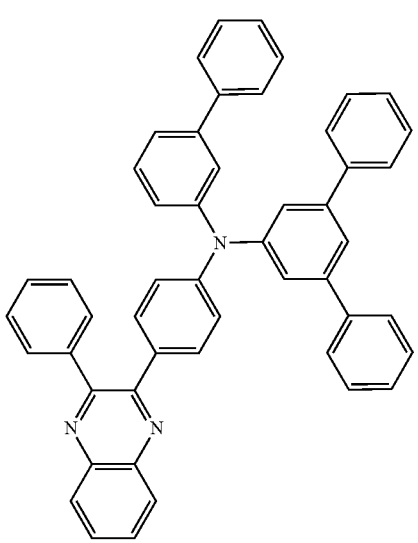
(162)

(163)
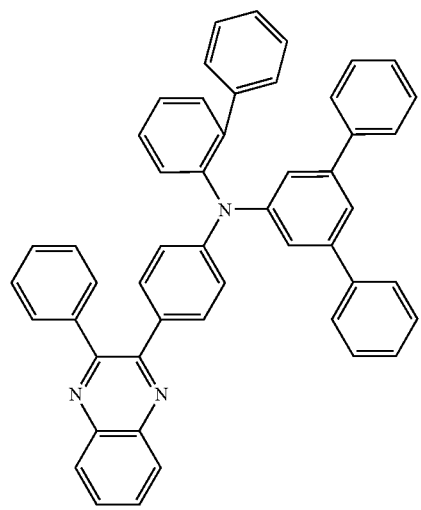
(164)
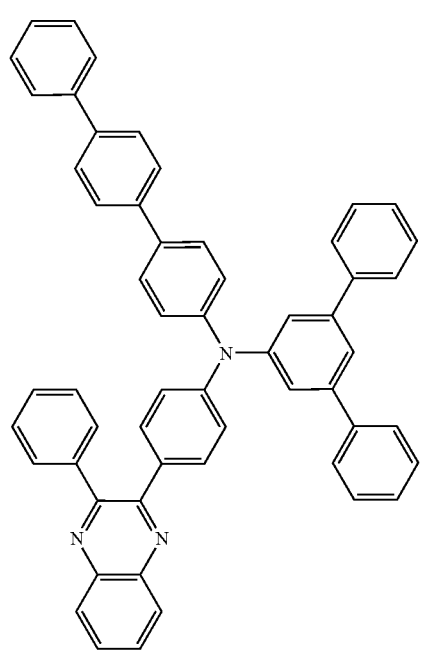
(165)
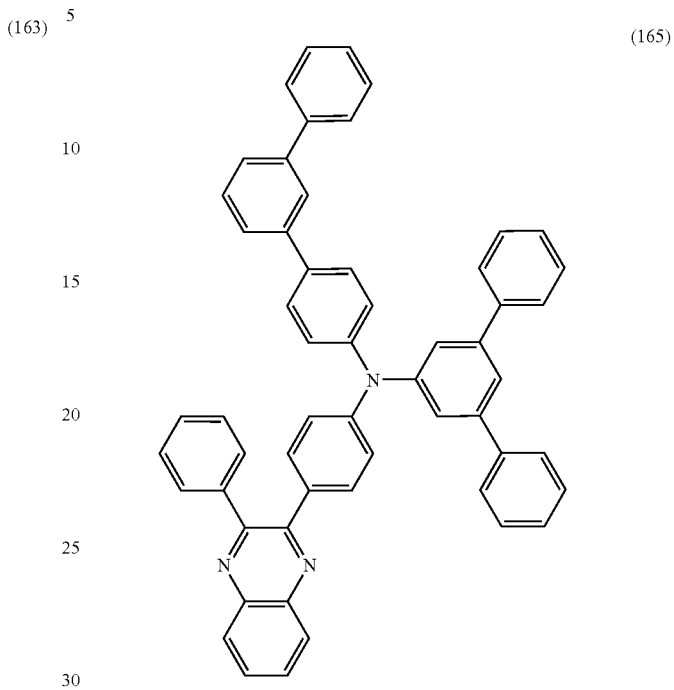
(166)
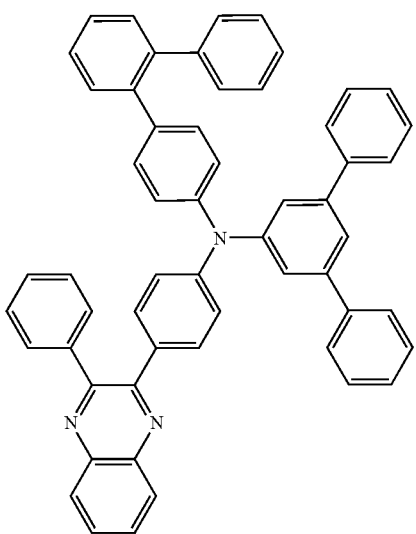

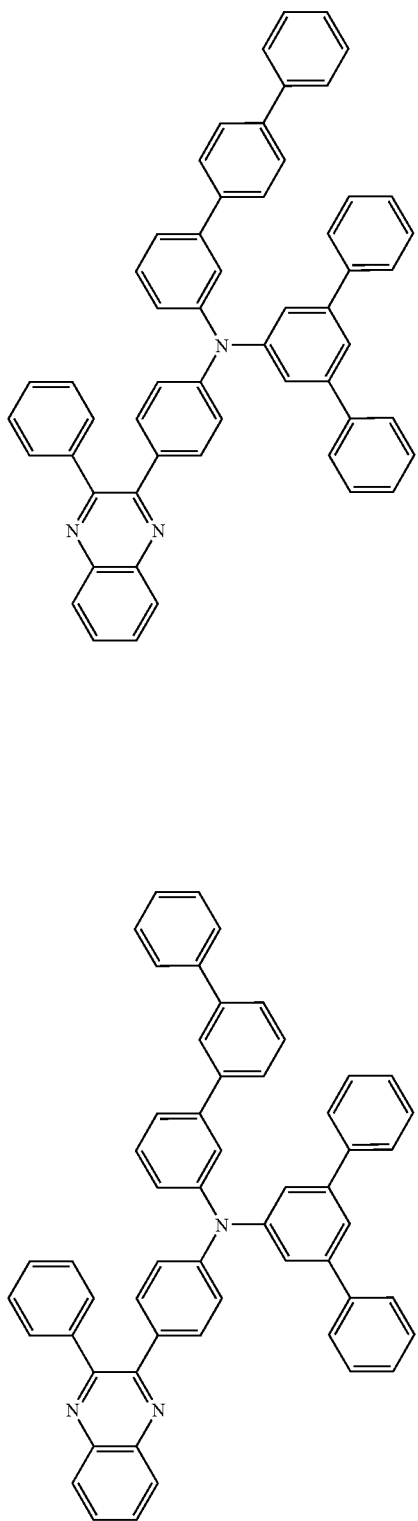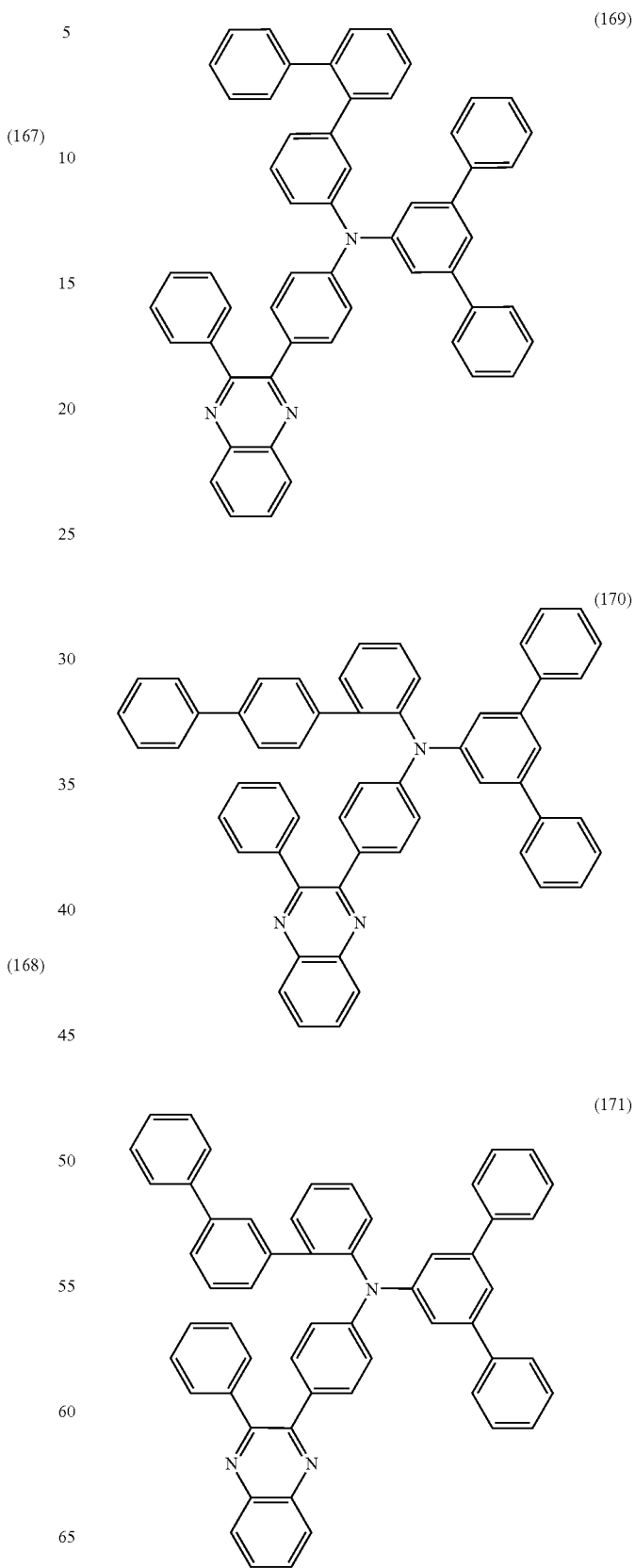

(172) 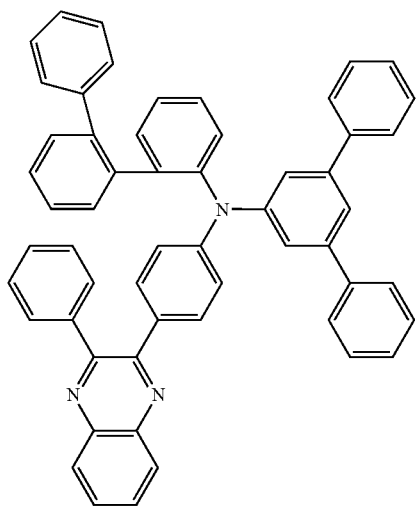
(173) 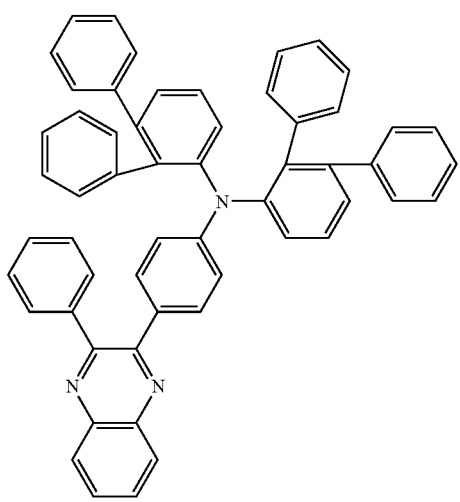
(174) 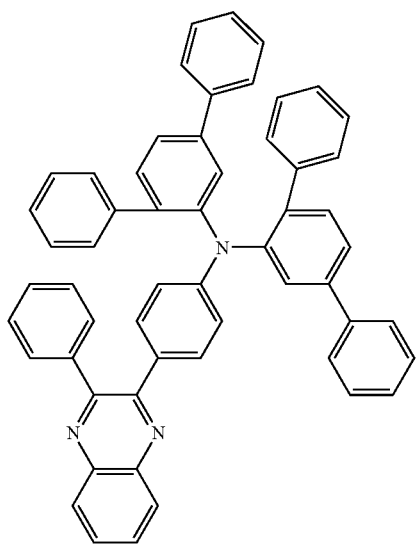
(175) 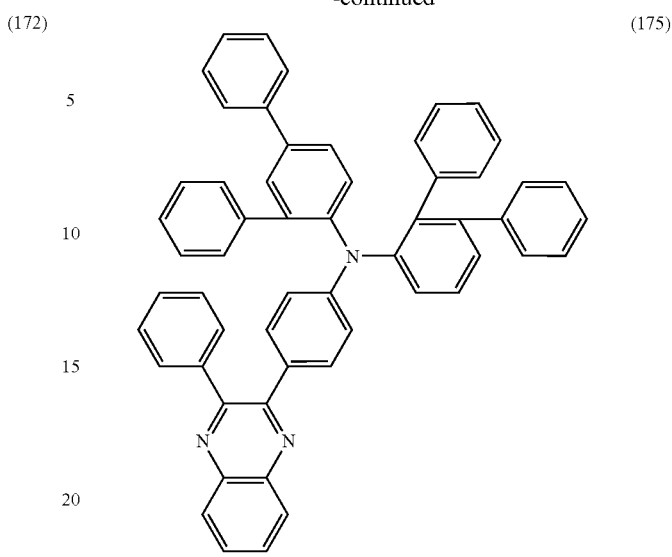
(176) 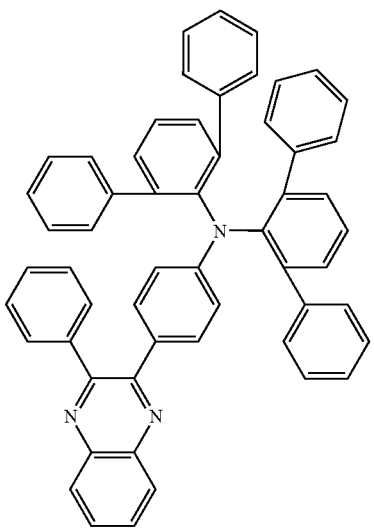
(177) 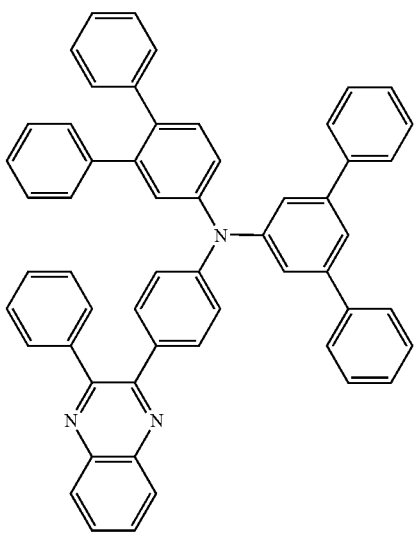

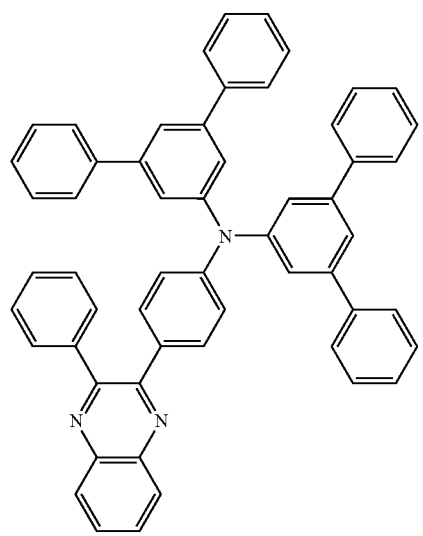 (178)
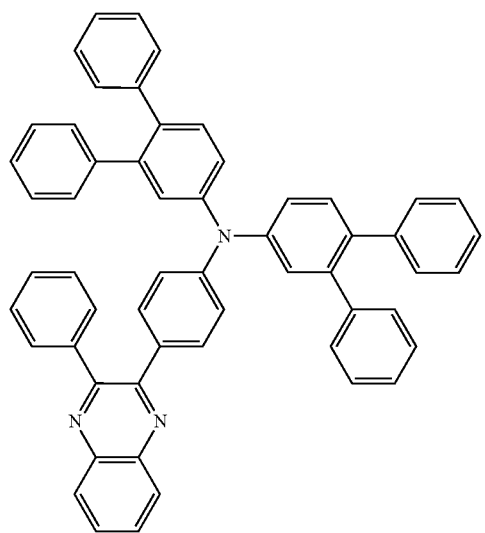 (179)
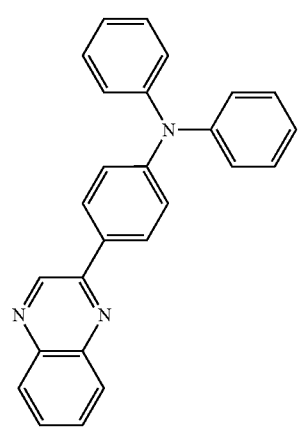 (180)
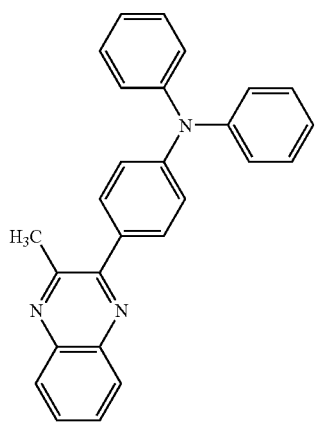 (181)
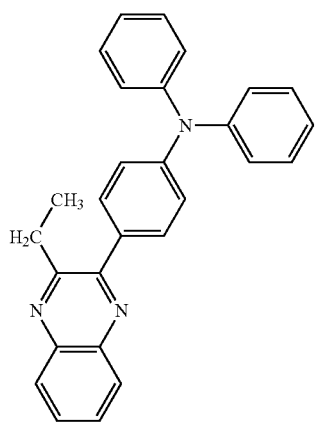 (182)
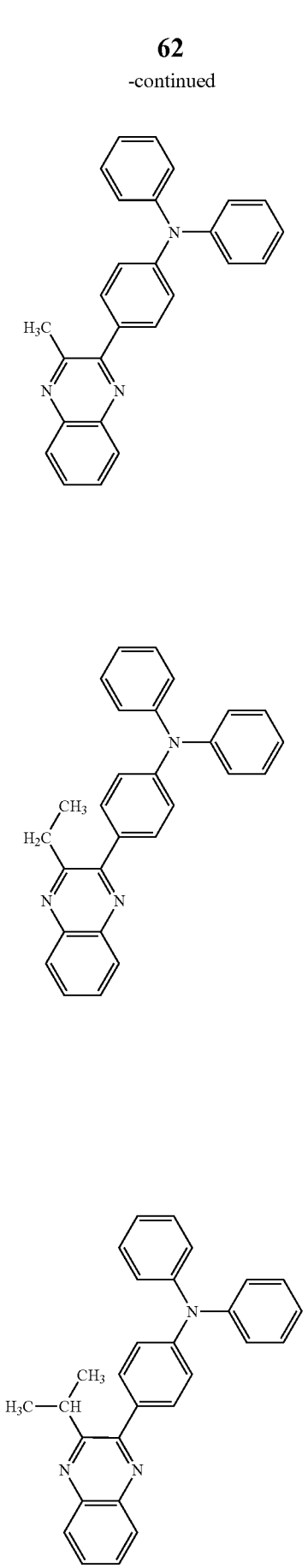 (183)

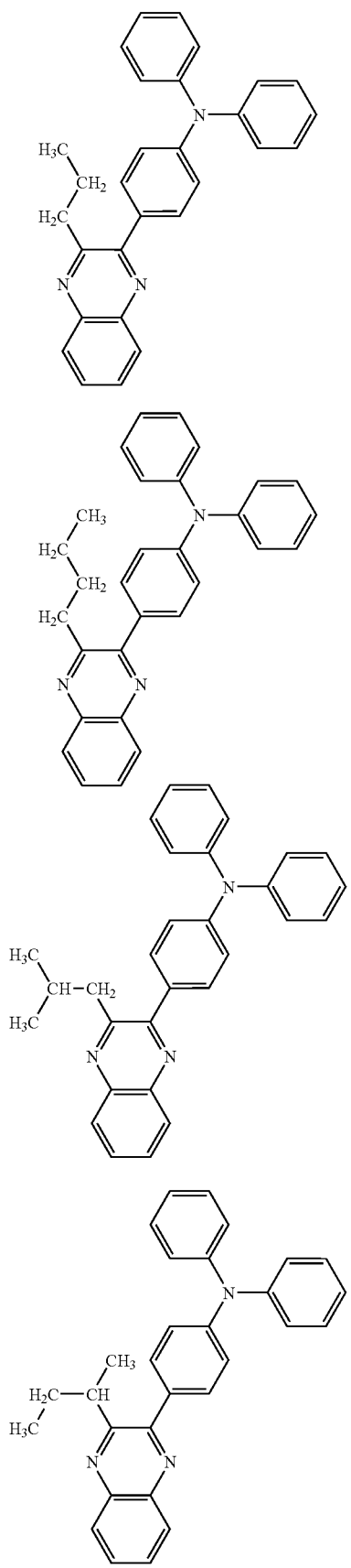
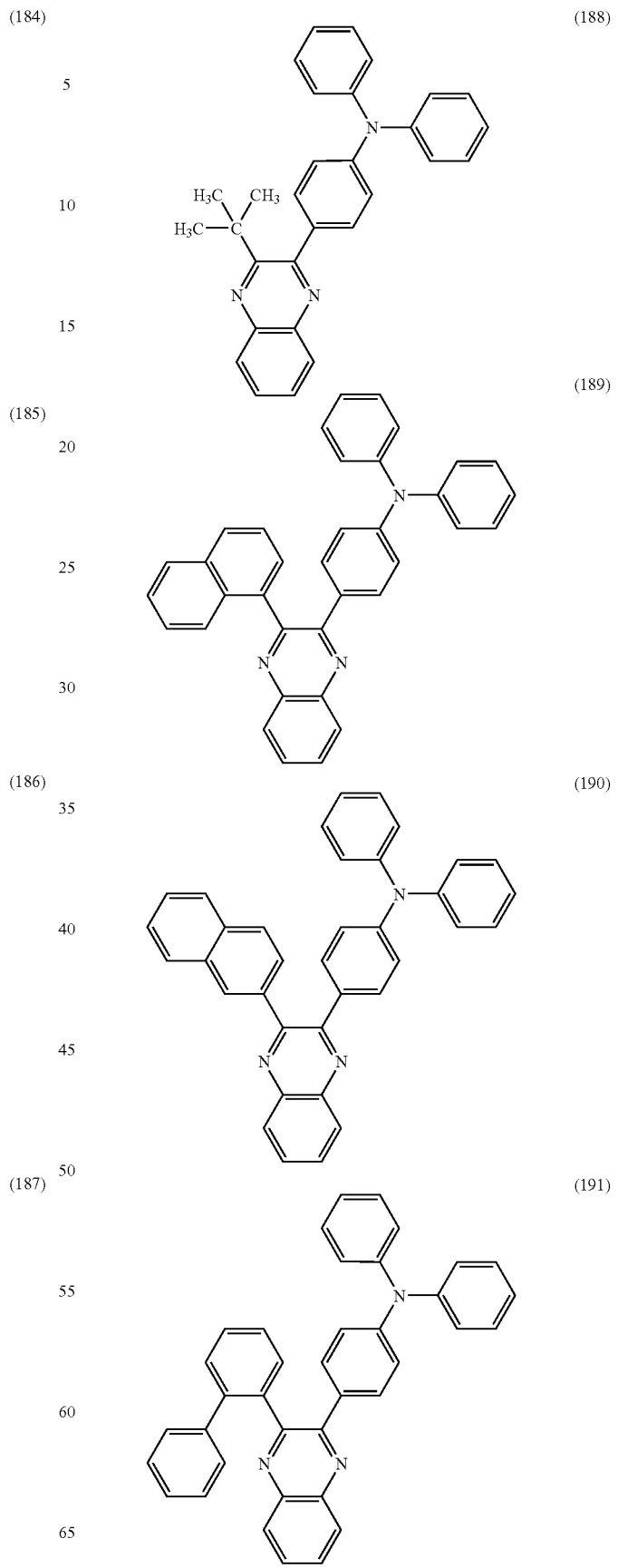

(192)
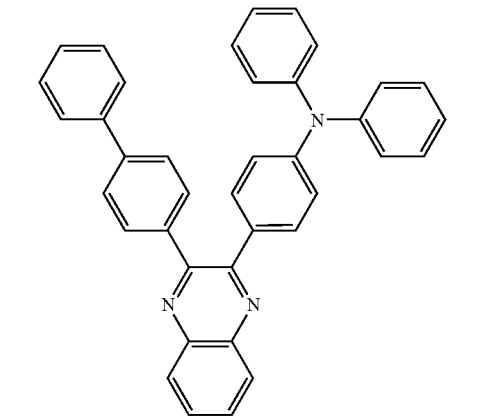
(193)
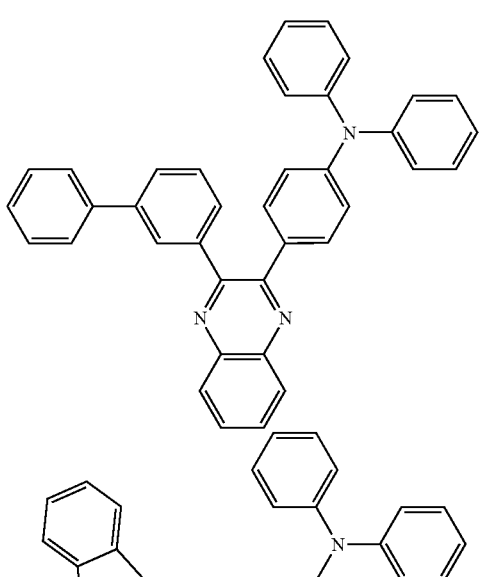
(194)
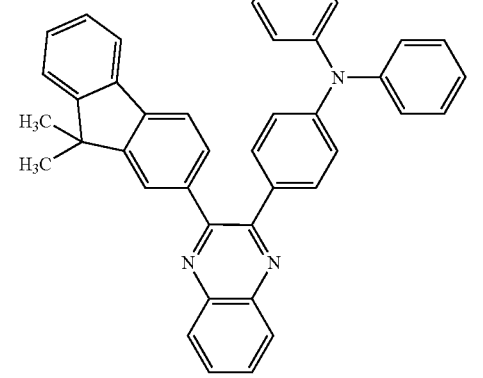
(195)
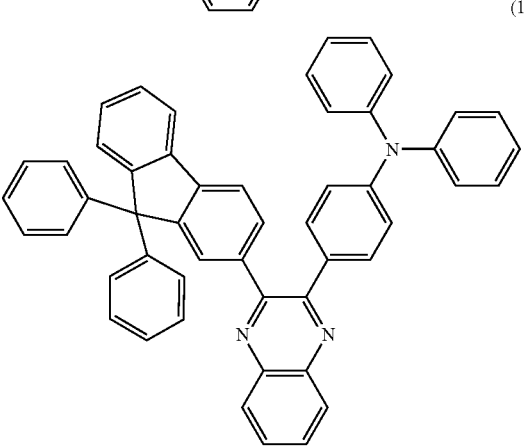
(196)
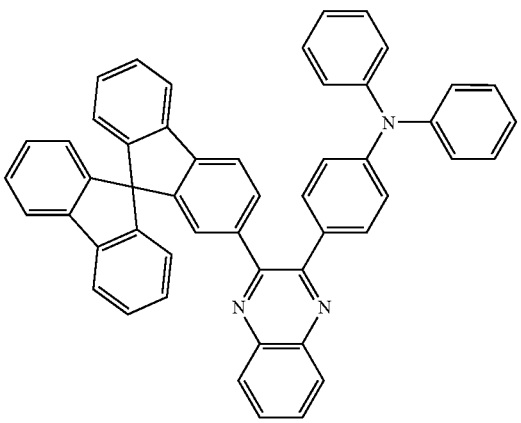
(197)
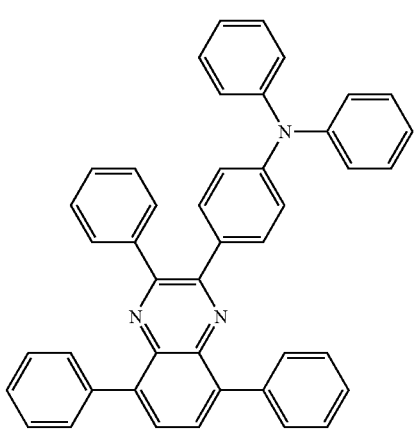
(198)
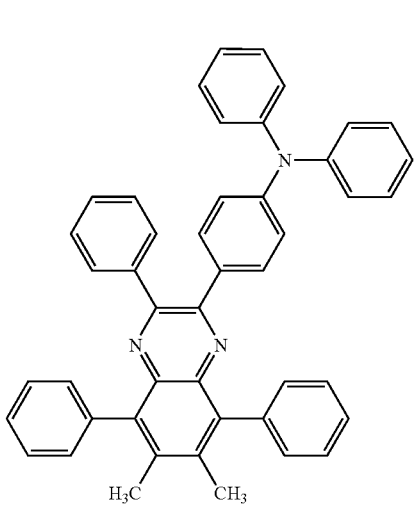

(199)
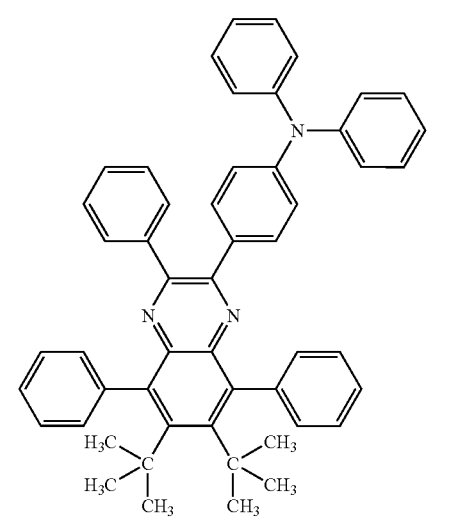
(200)
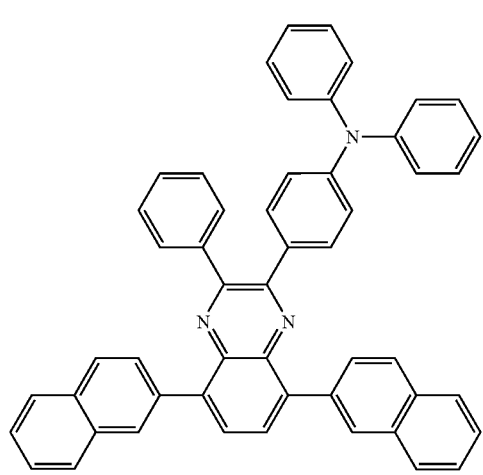
(201)
(202)
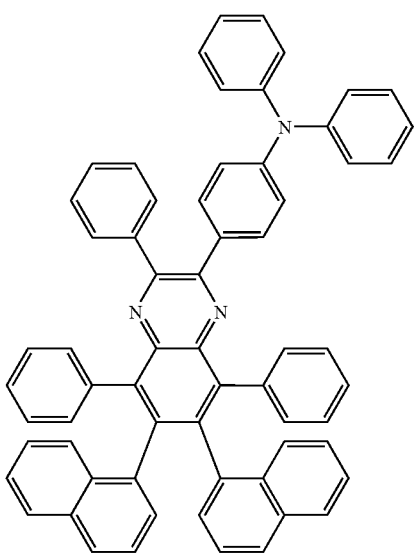
(203)
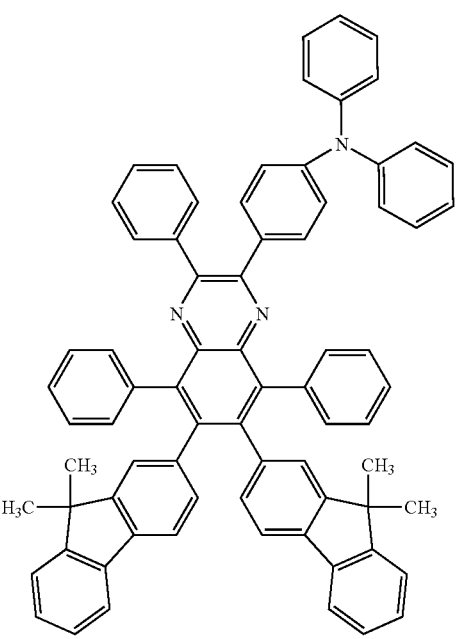

(204)
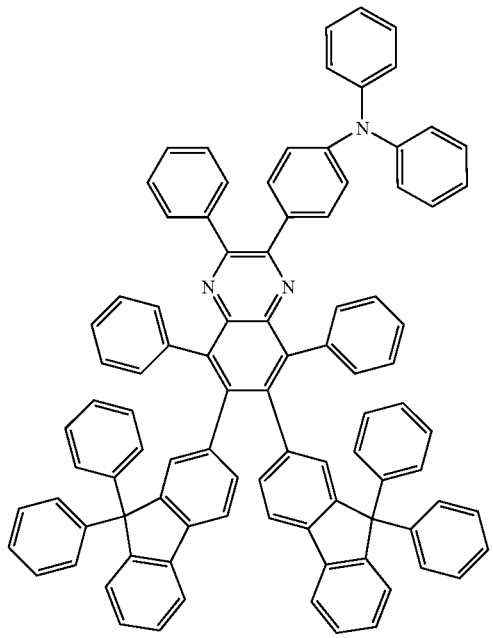
(205)
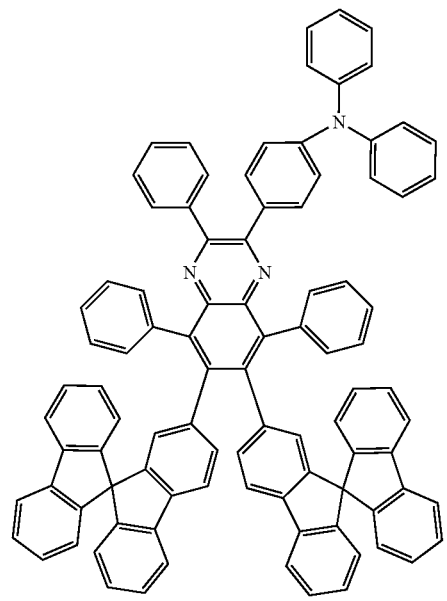
(206)
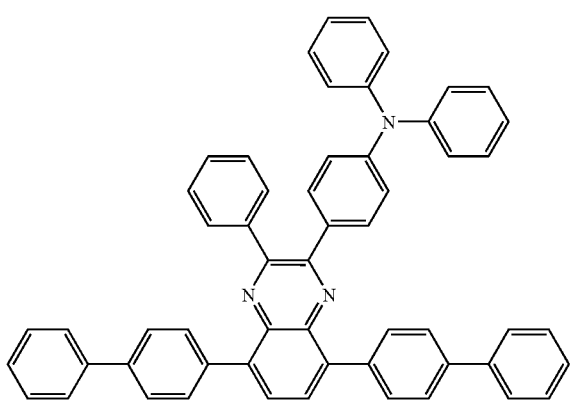
(207)
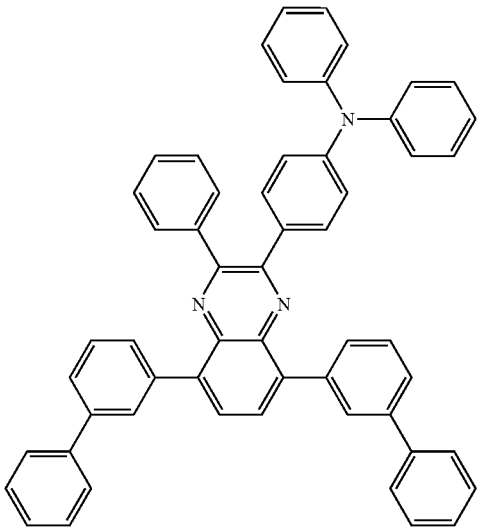
(208)
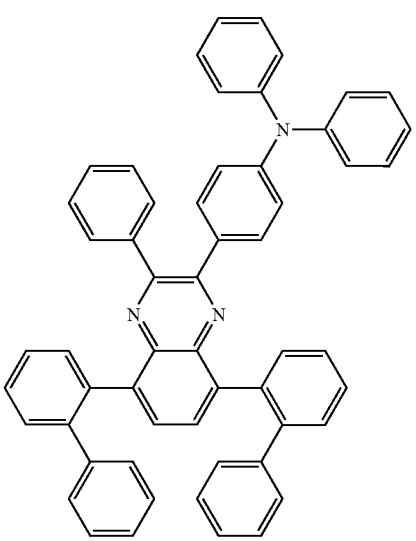
(209)
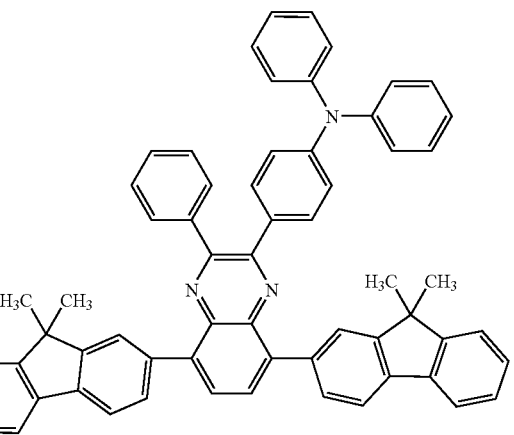

(210)
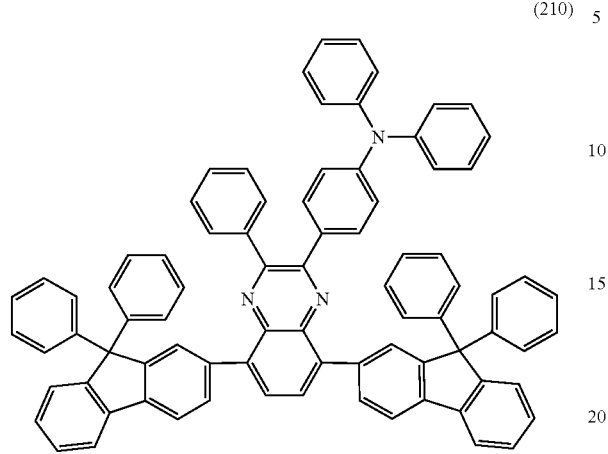
(211)
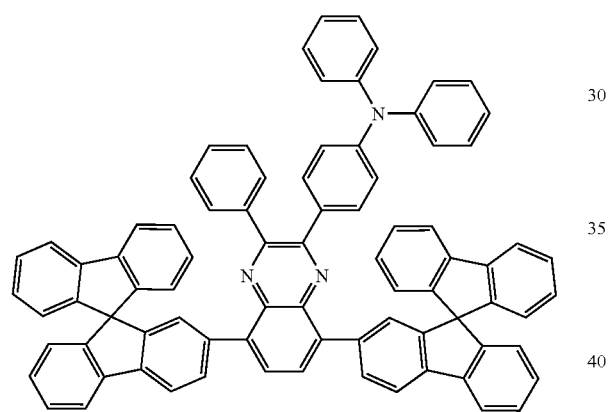
(212)
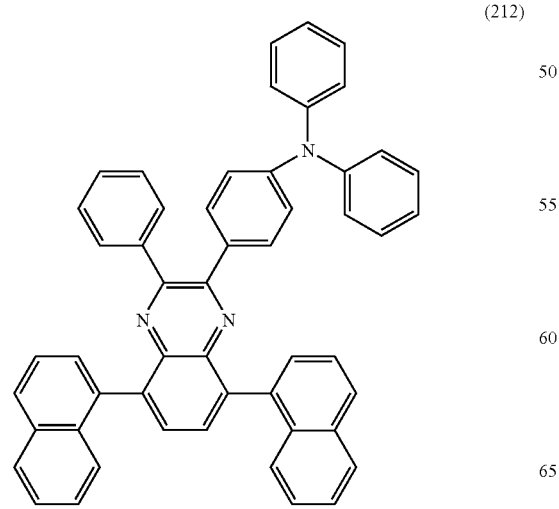
(213)
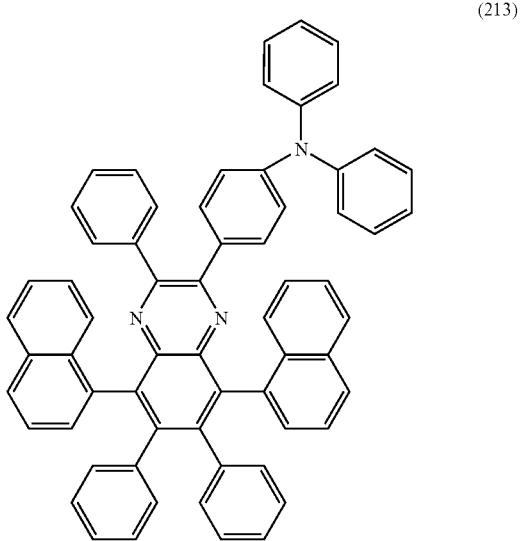
(214)
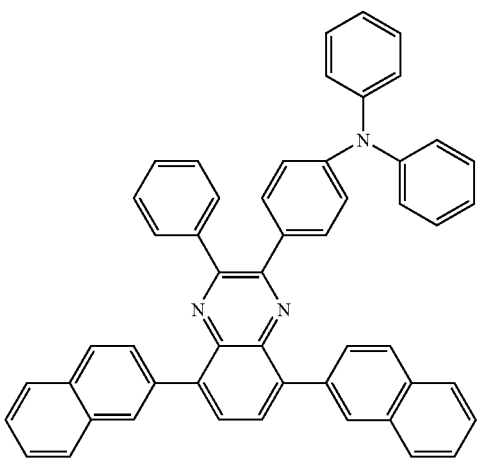
(215)
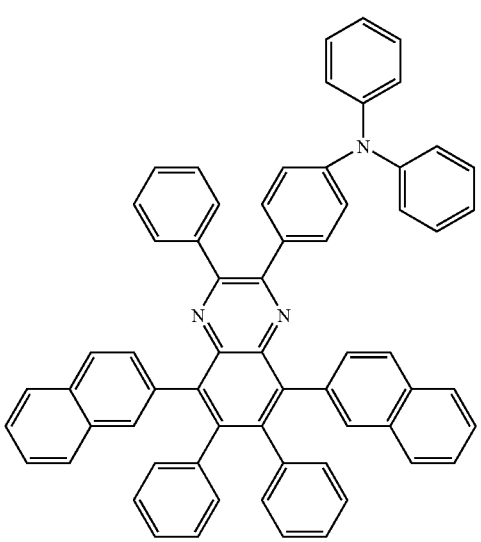

(216)
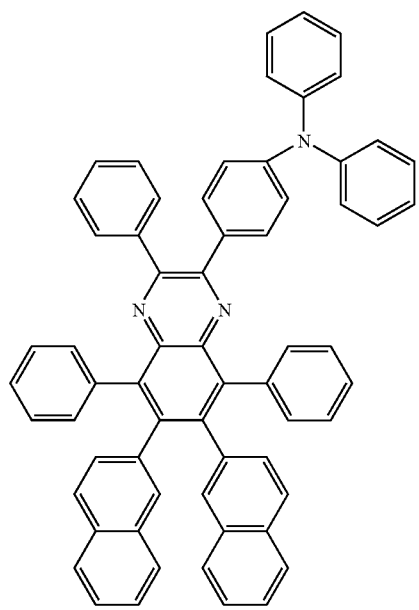
(217)
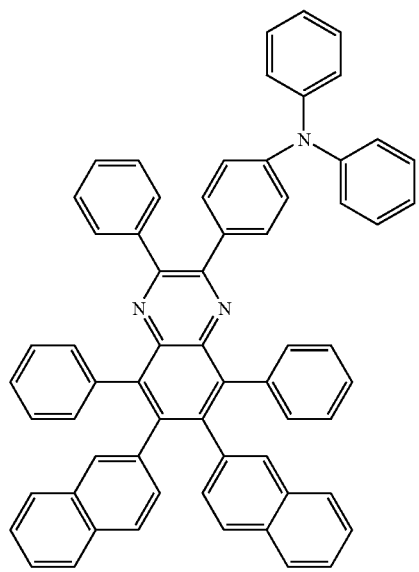
(218)
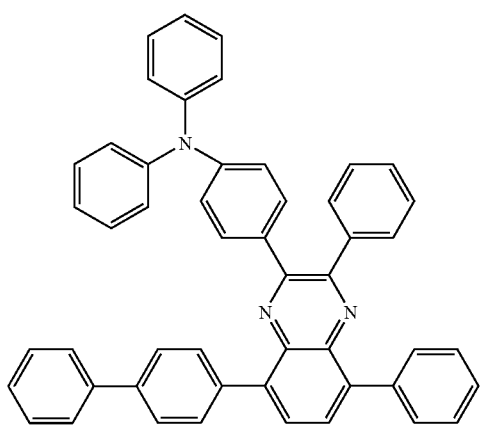
(219)
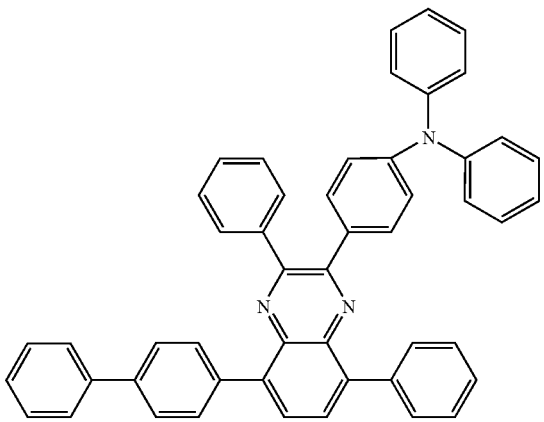
(220)
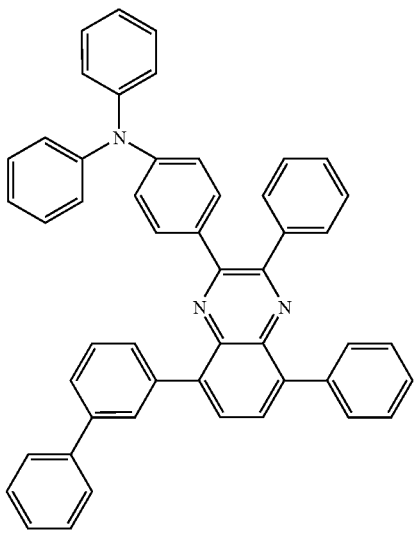
(221)
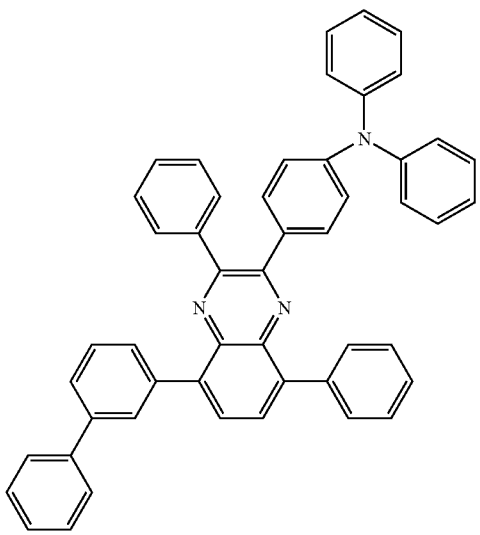

-continued
(222)
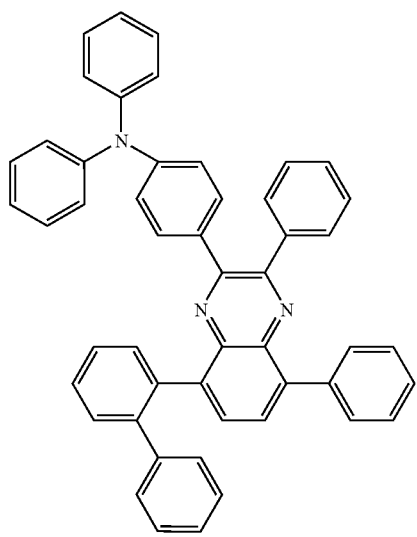
(223)
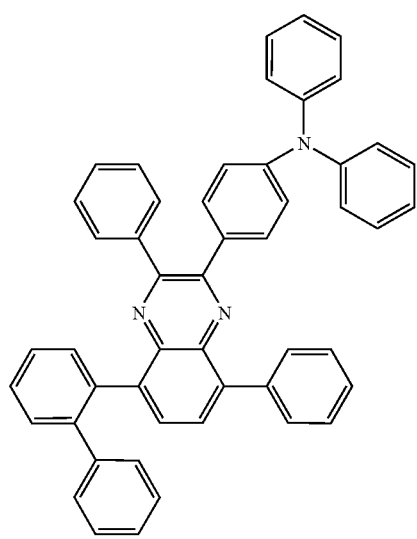
(224)
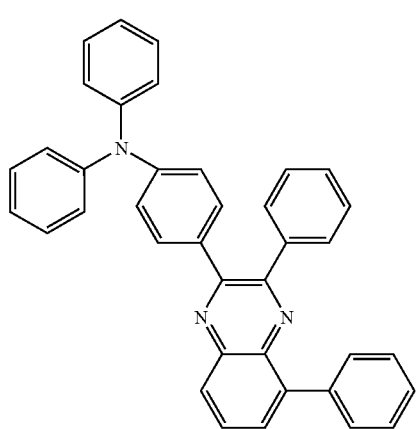
-continued
(225)
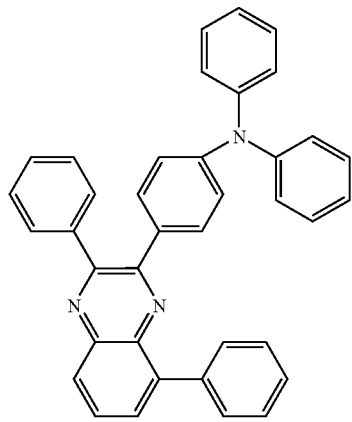
(226)
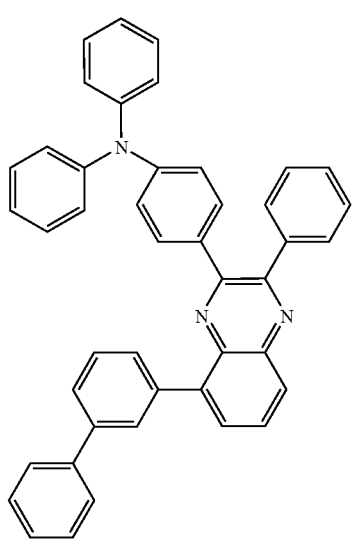
(227)
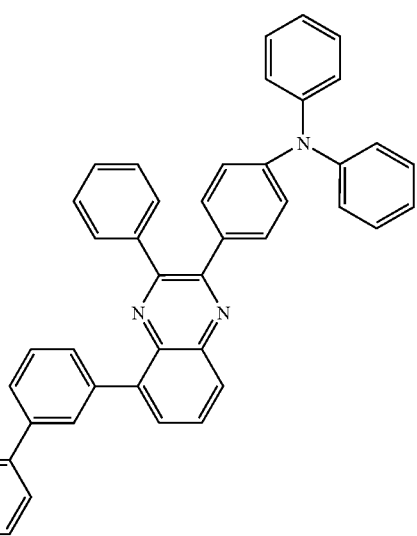

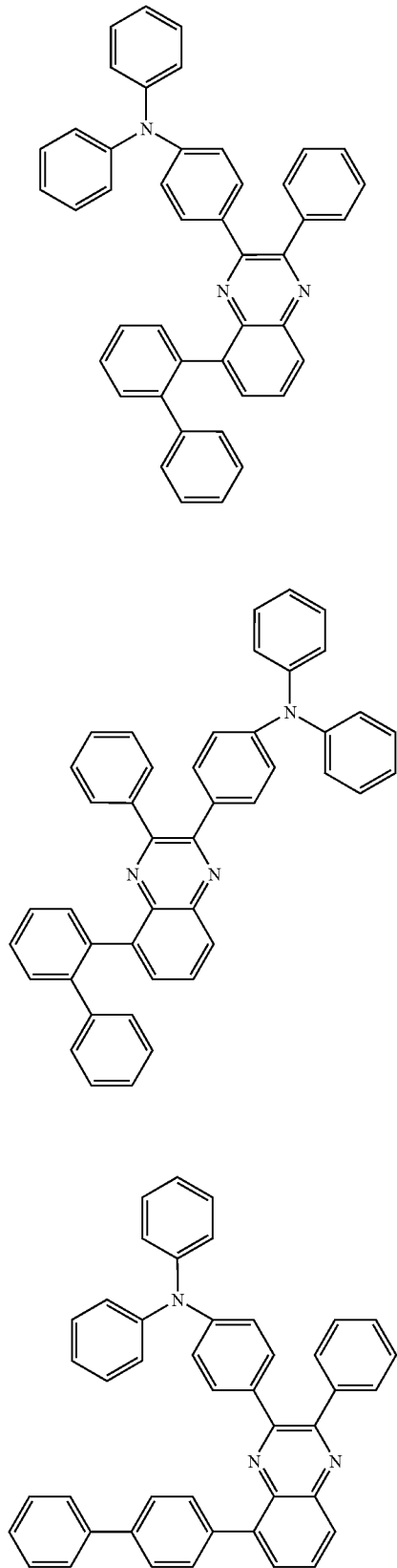
(228)
(229)
(230)
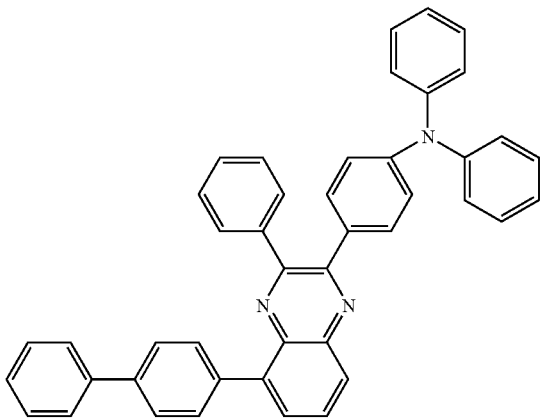
(231)
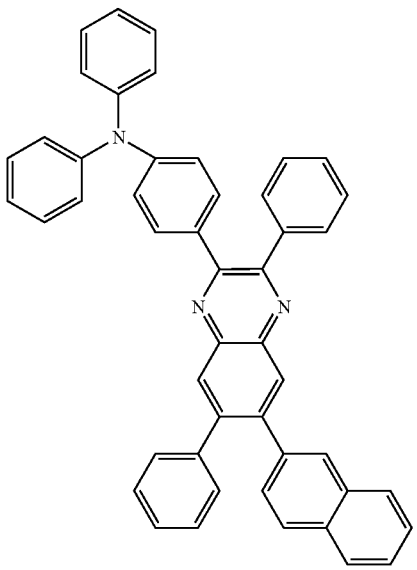
(232)
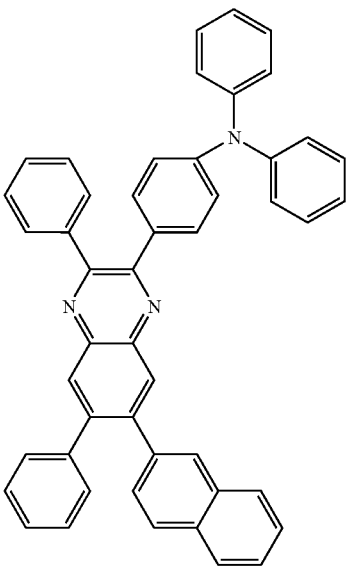
(233)

(234)
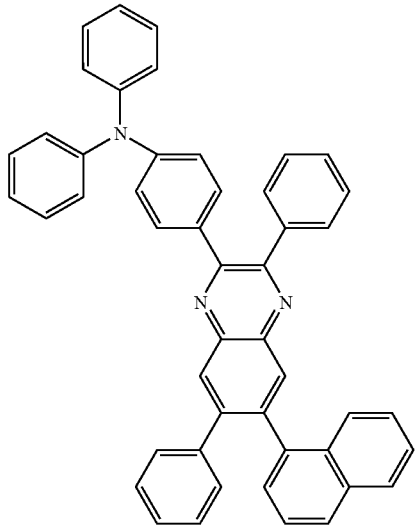
(235)
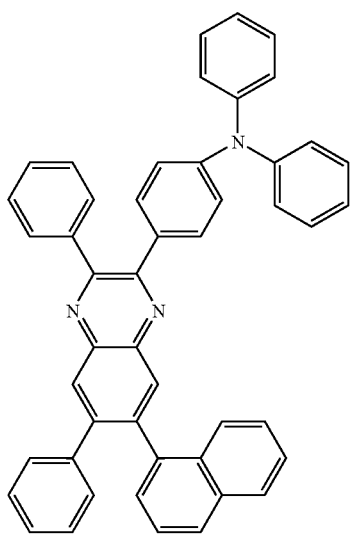
(236)
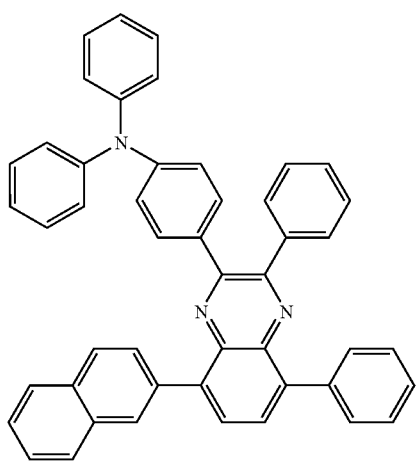
(237)
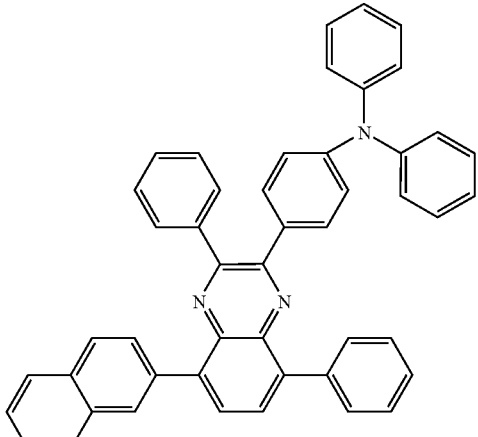
(238)
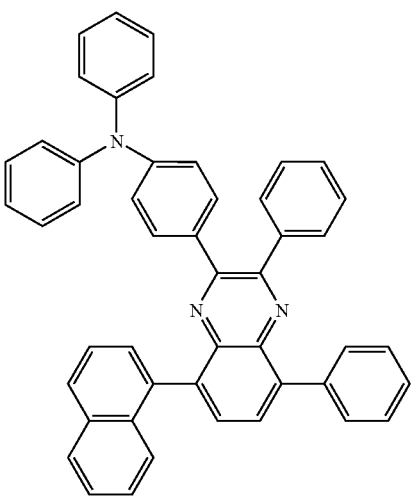
(239)
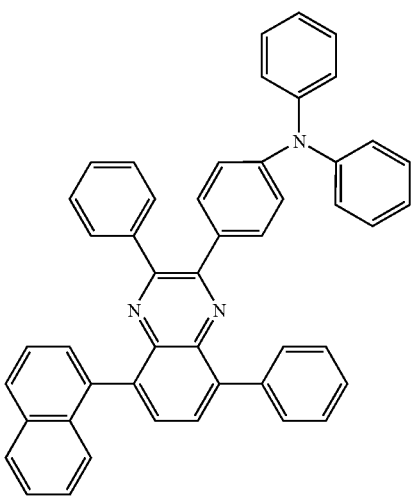

(240)
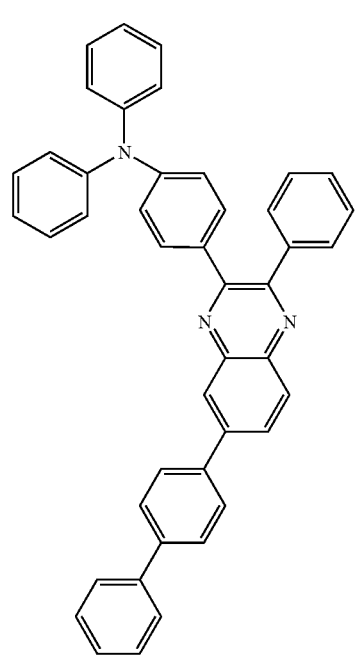
(241)
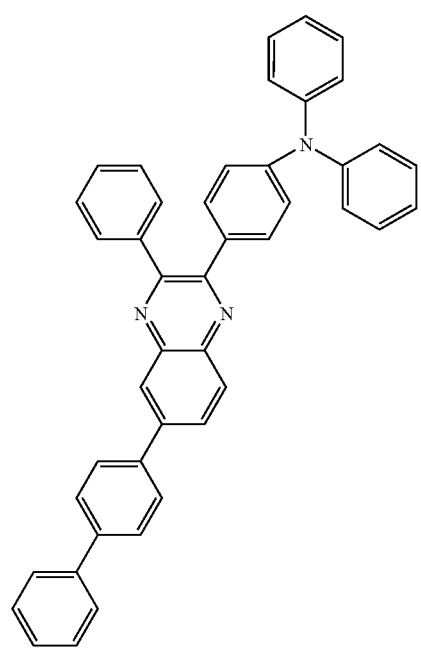
(242)
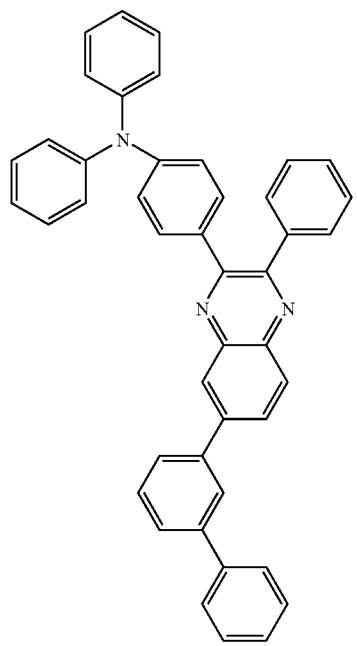
(243)
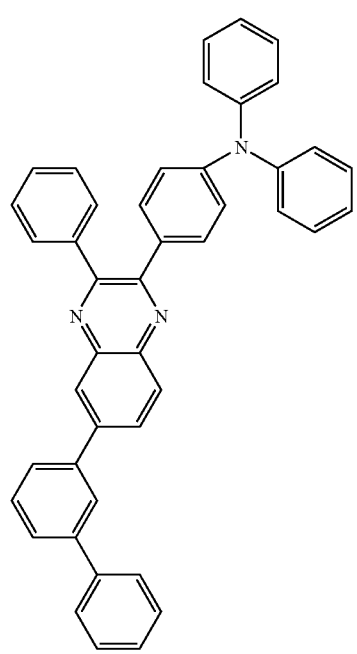

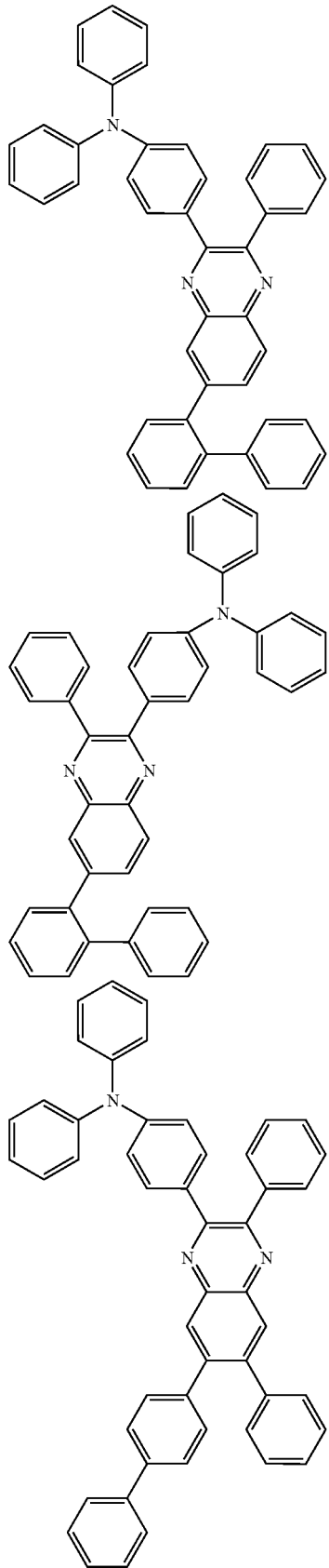
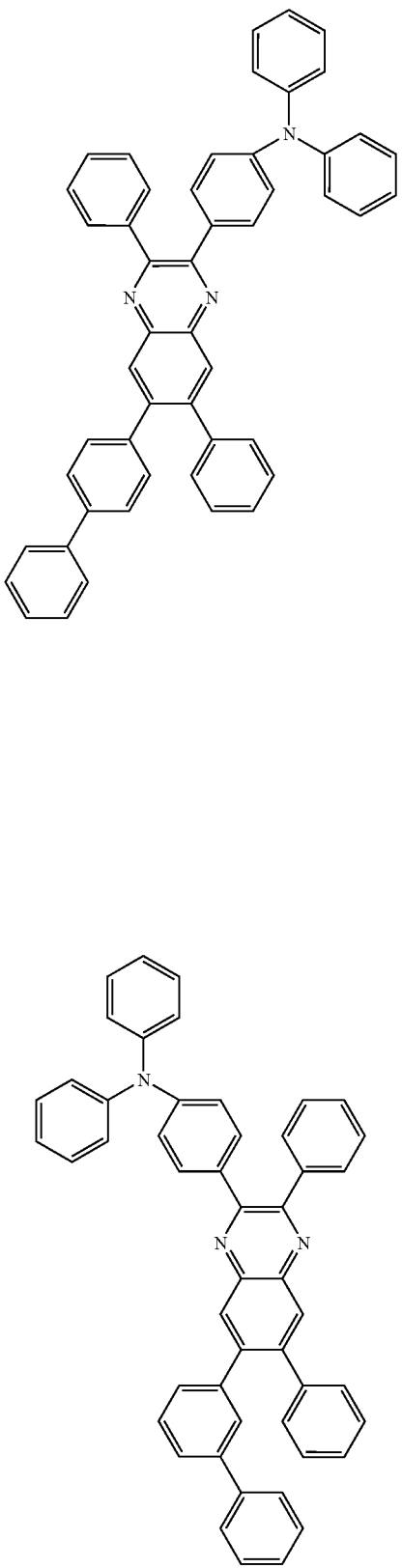

(249)
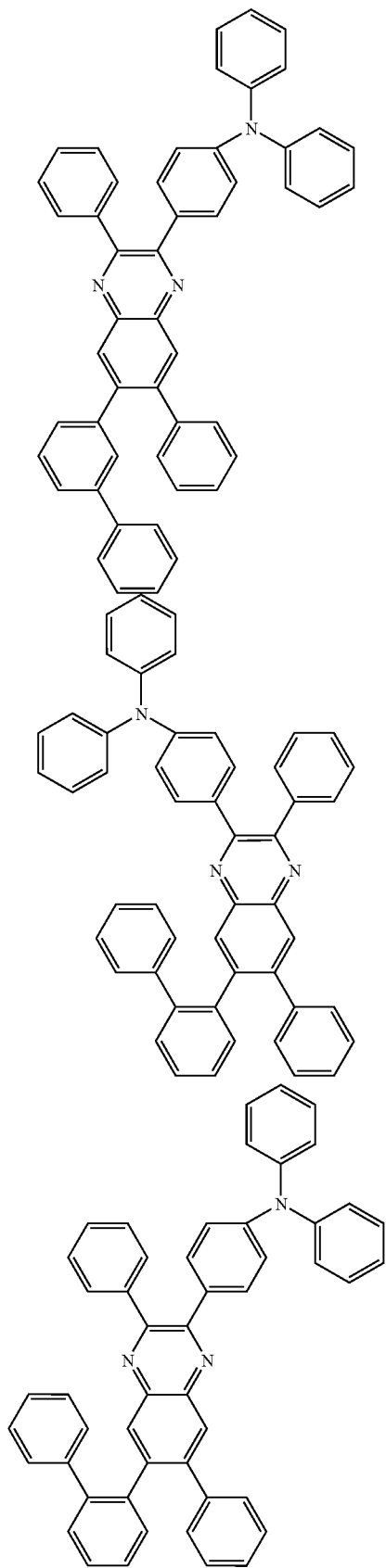
(250)
(251)
(252)
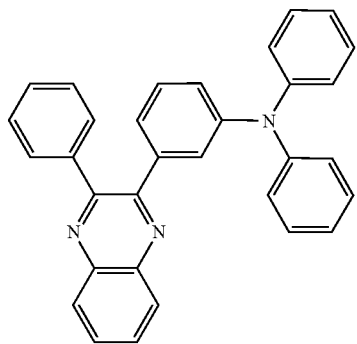
(253)
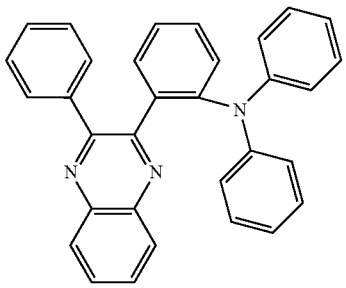
(254)
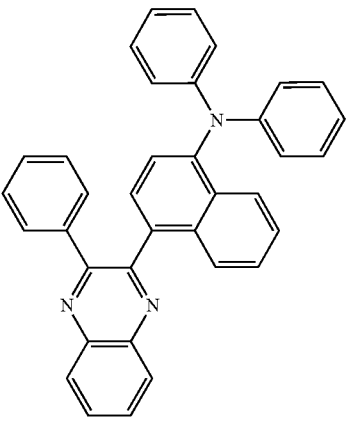
(255)
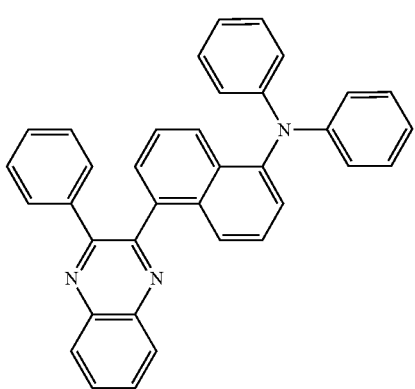

(256)

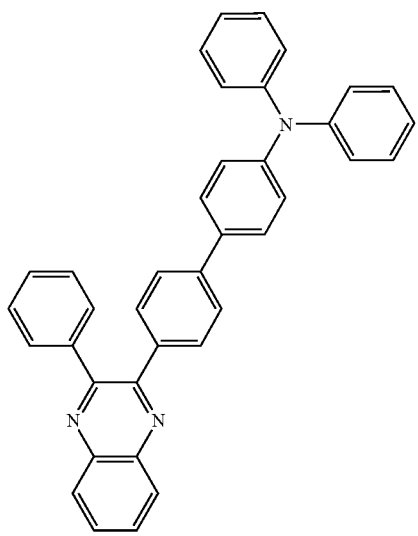

(257)

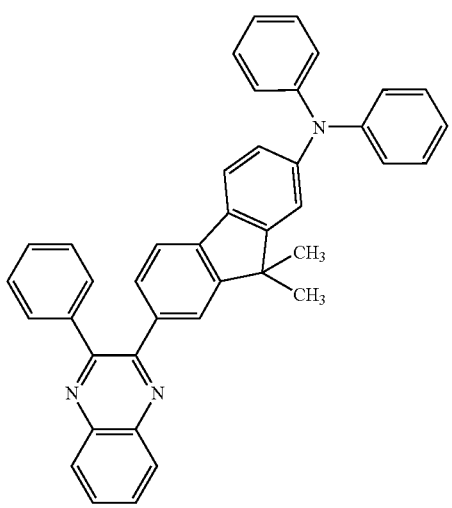

(258)

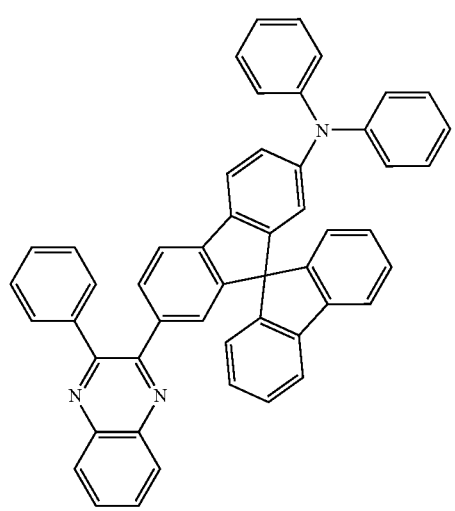

(259)

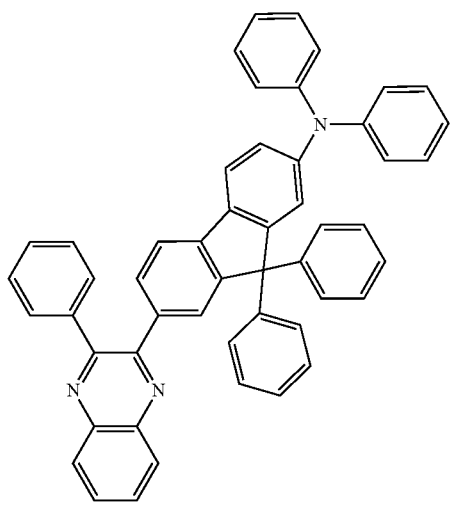

The quinoxaline derivatives of the present invention are bipolar because each of them has a hole-transporting amine skeleton and an electron-transporting quinoxaline skeleton in the same molecule. Any of the quinoxaline derivatives is preferably used, in a light-emitting element, as a material in which a light-emitting substance is dispersed, because of the bipolar properties. Furthermore, any of the quinoxaline derivatives of the present invention can be used for a carrier transporting layer because the quinoxaline derivatives can transport carriers.

The quinoxaline derivative represented by the general formula (1) has high singlet excitation energy because $Ar^1$ and $Ar^2$ are not condensed rings. Thus, it is preferred that, in a light-emitting element, the quinoxaline derivative be used as a material that disperses a light-emitting substance, or for a layer in contact with a layer containing a light-emitting substance. That is, the above quinoxaline derivative of the present invention can contact with a light-emitting substance. In particular, the above quinoxaline derivative can contact with a fluorescent substance because of the high singlet excitation energy. The quinoxaline derivative can prevent quenching of emission from a fluorescent substance even when this quinoxaline derivative contacts with a fluorescent substance emitting fluorescence at a relatively short wavelength because of the high singlet excitation energy.

In the above quinoxaline derivative, it is preferable that each of $\alpha^1$ and $R^{11}$ to $R^{15}$ not be a condensed ring in view of triplet excitation energy. In other words, it is preferable that the quinoxaline derivative represented by the general formula $\alpha^1$) be a quinoxaline derivative in which each of $\alpha^1$ and $R^{11}$ to $R^{15}$ is not a condensed ring.

That is, the quinoxaline derivative represented by the following general formula (2) is preferable.

(2)

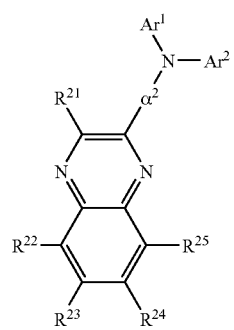

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^2$ represents an arylene group having 6 to 25 carbon atoms, which is not a condensed ring; and $R^{21}$ to $R^{25}$ may be the same or different from one another, and each of them represents any one of a hydrogen atom, an alkyl group having 1 to 4 carbon atoms, and a substituted or unsubstituted aryl group having 6 to 25 carbon atoms, which is not a condensed ring.

In the general formula (2), a quinoxaline derivative having high triplet excitation energy can be obtained when $\alpha^2$ and $R^{21}$ to $R^{25}$ are not condensed rings. Accordingly, it is preferred that, in a light-emitting element, the quinoxaline derivative be used as a material in which a phosphorescent substance is dispersed or for a layer in contact with a layer containing a phosphorescent substance. That is, the quinoxaline derivative of the present invention can contact with a phosphorescent substance. The quinoxaline derivative can prevent quenching of emission from a phosphorescent substance even when this quinoxaline derivative contacts with a phosphorescent substance emitting phosphorescence at a relatively short wavelength because of the high triplet excitation energy.

Specific examples of an aryl group that is not a condensed ring include a substituted or unsubstituted phenyl group, a substituted or unsubstituted biphenyl group, and a substituted or unsubstituted fluorene group. Specific examples of an arylene group that is not a condensed ring include a phenylene group, a biphenyl-diyl group, and a fluorene-diyl group.

That is, the quinoxaline derivative represented by the following general formula (3) is preferable.

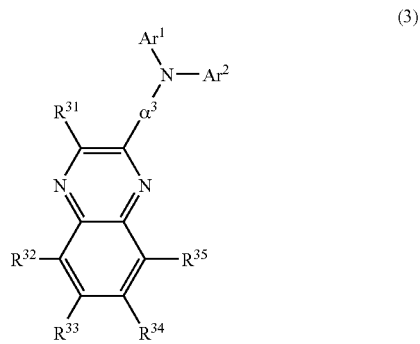

(3)

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^3$ represents any one of a phenylene group, a biphenyl-diyl group, and a fluorene-diyl group; and $R^{31}$ to $R^{35}$ may be the same or different from one another, and each of them represents any one of a hydrogen atom, an alkyl group having 1 to 4 carbon atoms, a substituted or unsubstituted phenyl group, a substituted or unsubstituted biphenyl group, and a substituted or unsubstituted fluorene group.

In a general formula (3), it is preferable that $\alpha^3$ be one of a phenylene group and a biphenyl-diyl group in terms of synthesis. Further, it is preferable that each of $R^{31}$ to $R^{35}$ be any one of a hydrogen atom, an alkyl group having 1 to 4 carbon atoms, a substituted or unsubstituted phenyl group, and a substituted or unsubstituted biphenyl group. These substituents can be easily synthesized through fewer synthetic steps. Furthermore, cost of the synthesis is low.

Therefore, the quinoxaline derivative represented by the following general formula (4) is preferable.

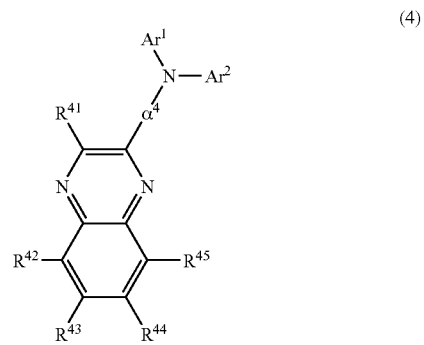

(4)

In the formula, $Ar^1$ and $Ar^2$ may be the same or different from one another and may be combined with one another, and each represents any one of a substituted or unsubstituted phenyl group, a substituted or unsubstituted biphenyl group, and a substituted or unsubstituted terphenyl group; $\alpha^4$ represents one of a phenylene group and a biphenyl-diyl group; and $R^{41}$ to $R^{45}$ may be the same or different from one another, and each of them represents any one of a hydrogen atom, an alkyl group having 1 to 4 carbon atoms, a substituted or unsubstituted phenyl group, and a substituted or unsubstituted biphenyl group.

Another aspect of the present invention is the quinoxaline derivative represented by the general formula (5).

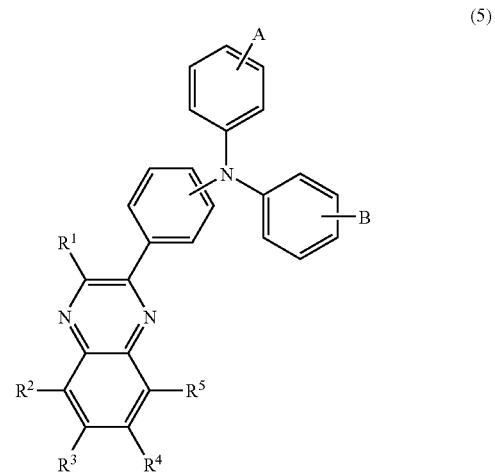

(5)

In the formula, A and B may be the same or different from one another, and each represents one of hydrogen and a phenyl group; and $R^1$ to $R^5$ may be the same or different from one another, and each represents any one of a hydrogen atom, an alkyl group having 1 to 4 carbon atoms, a substituted or unsubstituted phenyl group, and a substituted or unsubstituted biphenyl group.

Another aspect of the present invention is the quinoxaline derivative represented by the general formula (6).

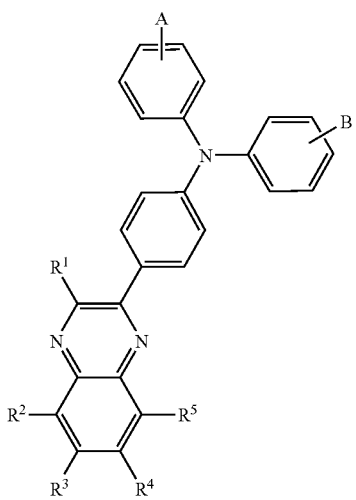

(6)

In the formula, A and B may be the same or different from one another, and each represents one of hydrogen and a phenyl group; and $R^1$ to $R^5$ may be the same or different from one another, and each represents any one of a hydrogen atom, an alkyl group having 1 to 4 carbon atoms, a substituted or unsubstituted phenyl group, and a substituted or unsubstituted biphenyl group.

In the above general formula (6), it is preferable that each of $R^2$ to $R^5$ be a hydrogen atom in terms of synthesis.

Therefore, the quinoxaline derivative represented by the general formula (7) is preferable.

(7)

In the formula, A and B may be the same or different from one another, and each represents one of hydrogen and a phenyl group; and $R^1$ represents any one of a substituted or unsubstituted phenyl group and a substituted or unsubstituted biphenyl group.

The quinoxaline derivatives of the present invention can be synthesized by any of various reactions. For example, one of the quinoxaline derivatives of the present invention can be formed by synthetic reactions shown in the following reaction schemes (A-1) and (A-2).

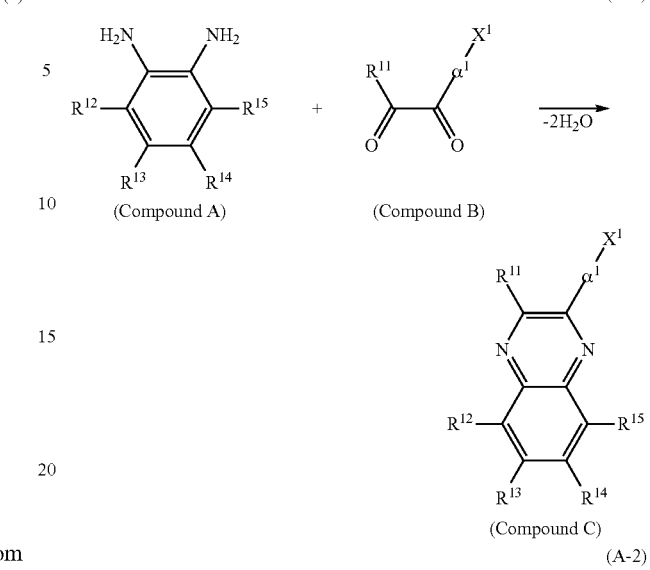

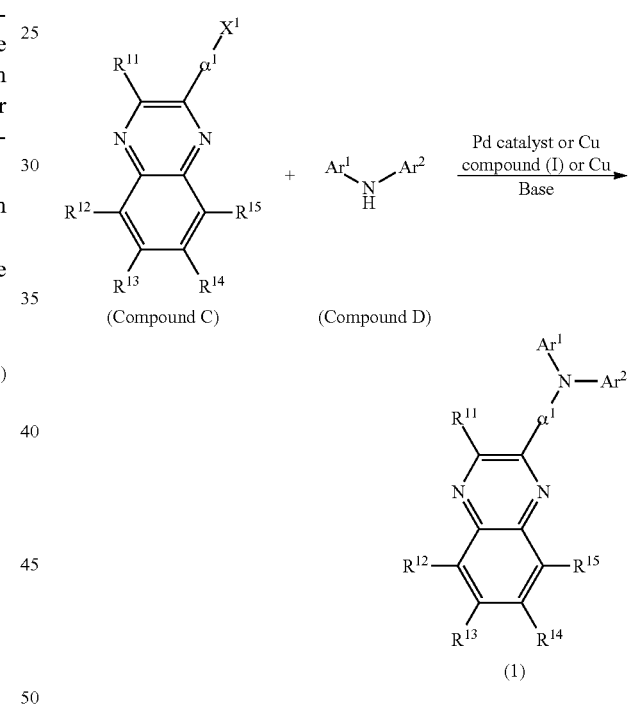

First, a quinoxaline skeleton is formed by a condensation reaction of a diketone compound substituted with a halogen atom $X^1$ (a compound B) and a compound having 1,2-diaminobenzene as the skeleton (a compound A). Although bromine, iodine, or chlorine is used as the halogen atom $X^1$, iodine or chlorine is preferable in consideration of easiness of handling and moderate reactivity.

One equivalent of diarylamine ($Ar^1$—NH—$Ar^2$) (a compound D) is coupled with the obtained quinoxaline compound substituted with aryl halide (a compound C), using a palladium catalyst, a metal compound of monovalent copper or the like, or metal such as copper, in the presence of a base; thus, an objective quinoxaline derivative of the present invention can be synthesized. Examples of the base include inorganic bases such as potassium carbonate and sodium carbonate, and organic bases such as metal alkoxide. Examples of the palladium catalyst include palladium(II) acetate, and bis(dibenzylideneacetone)palladium(0). Examples of the solvent include toluene, xylene, and benzene.

Diarylamine (Ar¹—NH—Ar²) (the compound D) in the above scheme can be synthesized as shown in the following scheme, for example.

Aryl halide (Ar¹—X²) is coupled with an arylamine compound (Ar²—NH₂), using a palladium catalyst, a metal compound of monovalent copper or the like, or metal such as copper; thus, diarylamine (Ar¹—NH—Ar²) (compound D) can be synthesized (synthetic scheme (A-3)). In this reaction, toluene, xylene, benzene, or the like can be used for the solvent.

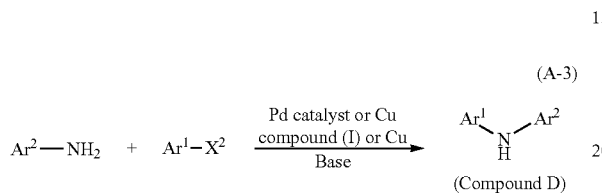

(A-3)

When Ar¹ is a biphenyl group, one equivalent of arylamine (Ar²—NH₂) is coupled with halogen-substituted biphenyl in which the 2, 3, or 4 position is substituted with halogen (X³), using a palladium catalyst, a metal compound of monovalent copper or the like, or metal such as copper, in the presence of a base; thus, objective arylamine (Ar¹—NH—Ar²; Ar¹ represents biphenyl group) can be obtained (synthetic scheme (A-4)). Examples of the base include inorganic bases such as potassium carbonate and sodium carbonate, and organic bases such as metal alkoxide. Examples of the palladium catalyst include palladium(II) acetate, and bis(dibenzylideneacetone)palladium(0). Examples of the solvent include toluene, xylene, and benzene.

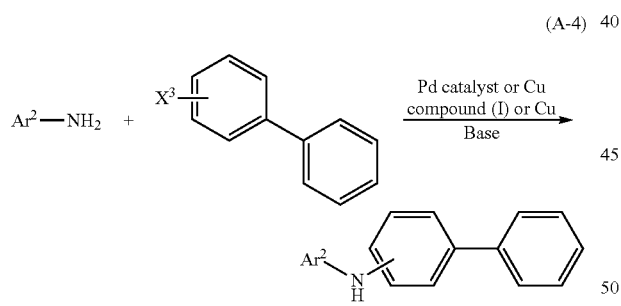

(A-4)

Alternatively, when each of Ar¹ and Ar² is a biphenyl group, two equivalents of phenylboronic acid or phenylboranes (e.g., 2-phenyl-4,4,5,5-tetramethyl-1,3,2-dioxaborolane) are coupled with diphenylamine in which both of two phenyl groups are substituted with halogen (X⁵ and X⁴), using a palladium catalyst in the presence of a base; thus, objective arylamine (Ar¹—NH—Ar²; both Ar¹ and Ar² represent biphenyl groups) can be obtained (synthetic scheme (A-5)). Examples of the base include inorganic bases such as potassium carbonate and sodium carbonate, and organic bases such as metal alkoxide. Examples of the palladium catalyst include palladium(II) acetate and tetrakis(triphenylphosphine)palladium(0). Examples of the solvent include alcohol such as ethanol; mixed solvents such as alcohol and toluene, alcohol and xylene, and alcohol and benzene; and ether solvents such as ethylene glycol diethyl ether and ethylene glycol dimethyl ether. This method is preferred in that N,N-di(4-biphenylyl) amine can be synthesized without using 4-aminobiphenyl that is harmful to humans.

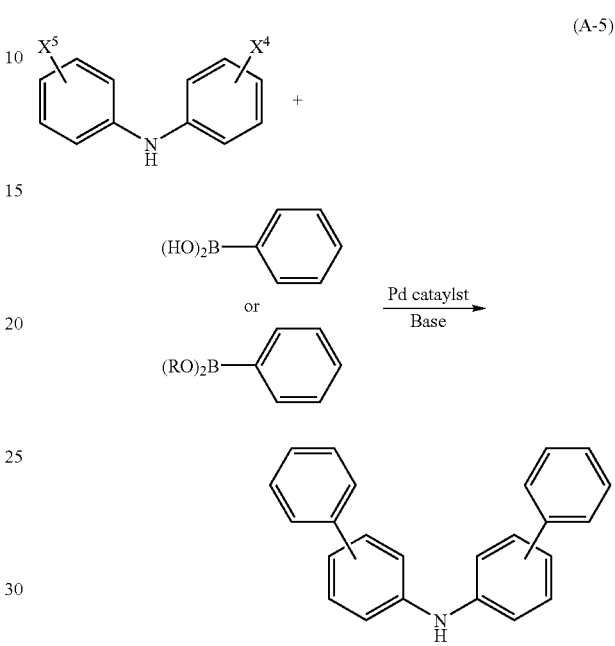

(A-5)

When arylamine in which Ar¹ is a terphenyl group is synthesized, first, one equivalent of phenylboronic acid or phenylboranes in which the 2, 3, or 4 position is substituted with a phenyl group is coupled with aniline in which the 2, 3, or 4 position is substituted with halogen (X⁵), using a palladium catalyst in the presence of a base; thus, various types of terphenylamine which are substituted at different positions can be synthesized (synthetic scheme (A-6)). Examples of the base include inorganic bases such as potassium carbonate and sodium carbonate, and organic bases such as metal alkoxide. Examples of the palladium catalyst include palladium(II) acetate and tetrakis(triphenylphosphine)palladium(0). Examples of the solvent include alcohol such as ethanol; mixed solvents such as alcohol and toluene, alcohol and xylene, and alcohol and benzene; and ether solvents such as ethylene glycol diethyl ether and ethylene glycol dimethyl ether.

Then, one equivalent of terphenylamine which is obtained above is coupled with aryl substituted with halogen (Ar²—X⁶), using a palladium catalyst, a metal compound of monovalent copper or the like, or metal such as copper in the presence of a base; thus, objective arylamine (Ar¹—NH—Ar²; Ar¹ represents a terphenyl group) can be obtained (synthetic scheme (A-7)). Examples of the base include inorganic bases such as potassium carbonate and sodium carbonate, and organic bases such as metal alkoxide, Examples of the palladium catalyst include palladium(II) acetate and bis(dibenzylideneacetone)palladium(0). Examples of the solvent include toluene, xylene, and benzene.

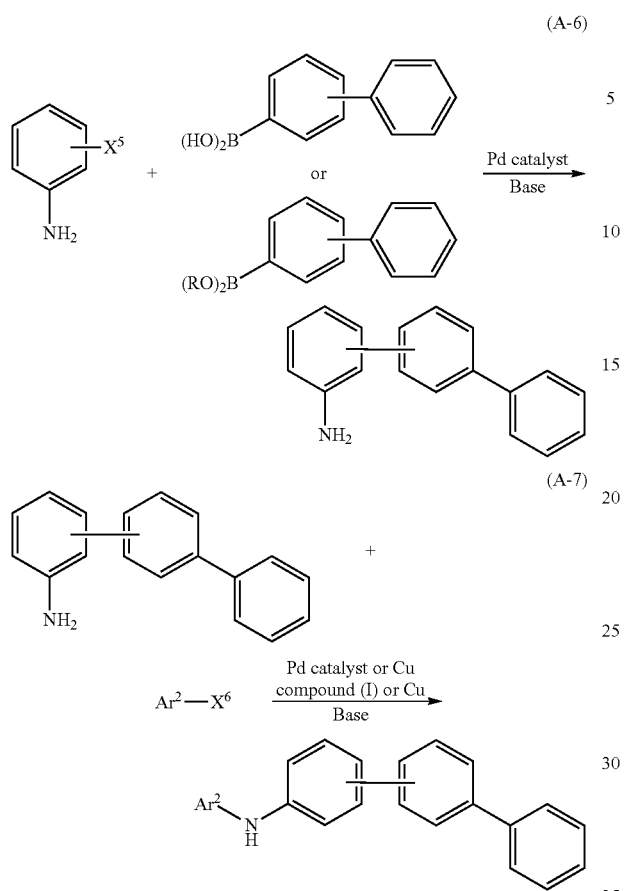

When Ar¹ is a terphenyl group and the central benzene ring of the terphenyl group is substituted with an amino group, first, two equivalents of phenylboronic acid or phenylboranes are coupled with aniline in which two positions are substituted with halogen (X⁷), using a palladium catalyst in the presence of a base; thus, terphenylamine in which the central benzene ring of the terphenyl group is substituted with an amino group is synthesized (synthetic scheme (A-8)). Examples of the base include inorganic bases such as potassium carbonate and sodium carbonate, and organic bases such as metal alkoxide. Examples of the palladium catalyst include palladium(II) acetate and tetrakis(triphenylphosphine)palladium(0) Examples of the solvent include alcohol such as ethanol; mixed solvents such as alcohol and toluene, alcohol and xylene, and alcohol and benzene; and ether solvents such as ethylene glycol diethyl ether and ethylene glycol dimethyl ether.

Then, one equivalent of terphenylamine which is obtained above is coupled with aryl substituted with halogen (Ar²—X¹), using a palladium catalyst, a metal compound of monovalent copper or the like, or metal such as copper in the presence of a base; thus, objective arylamine (Ar¹—NH—Ar²; Ar¹ represents a terphenyl group) can be obtained (synthetic scheme (A-9)). Examples of the base include inorganic bases such as potassium carbonate and sodium carbonate and organic bases such as metal alkoxide. Examples of the palladium catalyst include palladium(II) acetate and bis(dibenzylideneacetone)palladium(0). Examples of the solvent include toluene, xylene, and benzene.

The quinoxaline derivatives of the present invention are bipolar and excellent in both electron-transporting properties and hole-transporting properties; therefore, an electronic device using any of the quinoxaline derivatives of the present invention can have favorable characteristics. Furthermore, the quinoxaline derivatives of the present invention are stable to electrochemical oxidation and reduction; therefore, an electronic device using any of the quinoxaline derivatives of the present invention can have a long life.

(Embodiment Mode 2)

One mode of a light-emitting element including any of the quinoxaline derivatives of the present invention is described below with reference to FIG. 1A.

A light-emitting element of the present invention has a plurality of layers between a pair of electrodes. In this embodiment mode, the light-emitting element includes a first electrode 102, a second electrode 104, and an EL layer which is provided between the first electrode 102 and the second electrode 104. In this embodiment mode, the first electrode 102 is assumed as an anode and the second electrode 104 is assumed as a cathode. That is, light emission is obtained when a voltage is applied to the first electrode 102 and the second electrode 104 so that the potential of the first electrode 102 is higher than that of the second electrode 104.

A substrate 101 is a support of the light-emitting element. For example, glass, plastic, or the like can be used for the substrate 101. Any material other than these materials may be used as long as it functions as the support of the light-emitting element.

It is preferred that the first electrode 102 be formed using any of metal, alloy, and an electrically conductive compound each having a high work function (4.0 eV or higher), a mixture thereof, or the like. Specifically, indium tin oxide (ITO), ITO containing silicon or silicon oxide, indium zinc oxide (IZO), indium oxide containing tungsten oxide and zinc oxide (IWZO), or the like can be used. Films of such electrically conductive metal oxide are typically formed by sputtering, but may also be formed by applying a sol-gel method or the like. For example, indium zinc oxide (IZO) can be formed by a sputtering method using a target in which 1 to 20 wt % of zinc oxide is added to indium oxide. Indium oxide containing tungsten oxide and zinc oxide (IWZO) can be formed by a sputtering method using a target in which 0.5 to 5 wt % of tungsten oxide and 0.1 to 1 wt % of zinc oxide are added to indium oxide. Further, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used as the material for the first electrode 102.

There is no particular limitation on a stacked structure of an EL layer 103. It is acceptable as long as the EL layer 103 is formed by any combination of a layer containing any of the quinoxaline derivatives of the present invention, which are described in Embodiment Mode 1, with layers each containing a substance having high electron-transporting properties, a substance having high hole-transporting properties, a substance having high electron-injecting properties, a substance having high hole-injecting properties, a bipolar substance (a substance having high electron-transporting and hole-transporting properties), or the like. For example, any combination of a hole-injecting layer, a hole-transporting layer, a light-emitting layer, an electron-transporting layer, an electron-injecting layer, and the like can be employed. This embodiment mode describes a structure of the EL layer 103, in which a hole-injecting layer 111, a hole-transporting layer 112, a light-emitting layer 113, and an electron-transporting layer 114 are sequentially stacked over the first electrode 102.

The hole-injecting layer 111 is a layer containing a substance having high hole-injecting properties. As a substance having high hole-injecting properties, molybdenum oxide, vanadium oxide, ruthenium oxide, tungsten oxide, manganese oxide, or the like can be used. Alternatively, the hole-injecting layer 111 can be formed using any one of the following materials: phthalocyanine compounds such as phthalocyanine ($H_2PC$) and copper phthalocyanine (CuPc); aromatic amine compounds such as 4,4'-bis[N-(4-diphenylaminophenyl)-N-phenylamino]biphenyl (DPAB) and 4,4'-bis(N-{4-[N-(3-methylphenyl)-N-phenylamino]phenyl}-N-phenylamino)biphenyl (DNTPD); polymer compounds such as poly(3,4-ethylenedioxythiophene)/poly(styrenesulfonic acid) (PEDOT/PSS); and the like.

Alternatively, the hole-injecting layer 111 can be formed using a composite material in which an acceptor substance is mixed into a substance having high hole-transporting properties. It is to be noted that a material for forming the electrode can be selected regardless of its work function by using the composite material in which an acceptor substance is mixed into a substance having high hole-transporting properties. That is, not only a high-work function material, but also a low-work function material can be used for the first electrode 102. Examples of the acceptor substance include 7,7,8,8-tetracyano-2,3,5,6-tetrafluoroquinodimethane ($F_4$-TCNQ); chloranil; transition metal oxide; and oxide of metals that belong to Group 4 to Group 8 of the periodic table. Specifically, any of vanadium oxide, niobium oxide, tantalum oxide, chromium oxide, molybdenum oxide, tungsten oxide, manganese oxide, and rhenium oxide is preferably used because of their high electron accepting properties. In particular, molybdenum oxide is more preferable because of its stability in the atmosphere, low hygroscopic properties, and easiness of handling.

As the substance having high hole-transporting properties used for the composite material, any of various compounds such as an aromatic amine compound, a carbazole derivative, aromatic hydrocarbon, and a polymer compound (such as an oligomer, a dendrimer, or a polymer) can be used. It is preferable that the organic compound used for the composite material have high hole-transporting properties. Specifically, a substance having a hole mobility of greater than or equal to $10^{-6}$ $cm^2/Vs$ is preferable. Any substance other than the above substances may also be used as long as the hole-transporting properties of the substance is higher than the electron-transporting properties thereof. The organic compounds that can be used for the composite material are specifically shown below.

Examples of the aromatic amine compound include N,N'-di(p-tolyl)-N,N'-diphenyl-β-phenylenediamine (DTDPPA); 4,4'-bis[N-(4-diphenylaminophenyl)-N-phenylamino]biphenyl (DPAB); 4,4'-bis(N-{4-[N-3-methylphenyl)-N'-phenylamino]phenyl}-N-phenylamino)biphenyl (DNTPD), and 1,3,5-tris[N-(4-diphenylaminophenyl)-N-phenylamino]benzene (DPA3B).

Examples of the carbazole derivatives which can be used for the composite material include 3-[N-(9-phenylcarbazol-3-yl)-N-phenylamino]-9-phenylcarbazole (PCzPCA1); 3,6-bis[N-(9-phenylcarbazol-3-yl)-N-phenylamino]-9-phenylcarbazole (PCzPCA2), and 3-[N-(1-naphtyl)-N-(9-phenylcarbazol-3-yl)amino]-9-phenylcarbazole (PCzPCN1).

Examples of the carbazole derivatives which can be used for the composite material further include 4,4'-di(N-carbazolyl)biphenyl (CBP); 1,3,5-tris[4-(N-carbazolyl)phenyl]benzene (TCPB); 9-[4-(N-carbazolyl)]phenyl-10-phenylanthracene (CzPA), and 1,4-bis[4-(N-carbazolyl)phenyl]-2,3,5,6-tetraphenylbenzene.

Examples of the aromatic hydrocarbon which can be used for the composite material include 2-tert-butyl-9,10-di(2-naphthyl)anthracene (t-BuDNA); 2-tert-butyl-9,10-di(1-naphthyl)anthracene; 9,10-bis(3,5-diphenylphenyl)anthracene (DPPA); 2-tert-butyl-9,10-bis(4-phenylphenyl)anthracene (t-BuDBA); 9,10-di(2-naphthyl)anthracene (DNA); 9,10-diphenylanthracene (DPAnth); 2-tert-butylanthracene (t-BuAnth); 9,10-bis(4-methyl-1-naphthyl)anthracene (DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene, and 2,5,8,11-tetra(tert-butyl)perylene. Besides these compounds, pentacene, coronene, or the like can also be used. In particular, an aromatic hydrocarbon which has a hole mobility of greater than or equal to $1\times10^{-6}$ $cm^2/Vs$ and has 14 to 42 carbon atoms is more preferable.

The aromatic hydrocarbon which can be used for the composite material may have a vinyl skeleton. Examples of the aromatic hydrocarbon having a vinyl skeleton include 4,4'-bis(2,2-diphenylvinyl)biphenyl (DPVBi) and 9,10-bis[4-(2,2-diphenylvinyl) phenyl]anthracene (DPVPA).

Examples of the substance used for the composite material further include polymer compounds such as poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA); and poly[N,N'-bis(4-butylphenyl)-N,N'-bis(phenyl)benzidine] (Poly-TPD).

The hole-transporting layer 112 is a layer containing a substance having high hole-transporting properties. Examples of the substance having high hole-transporting properties include aromatic amine compounds such as 4,4'-bis[N-(1-naphthyl)-N-phenylamino]biphenyl (NPB), N,N'- bis(3-methylphenyl)-N,N'-diphenyl-[1,1'-biphenyl]-4,4'-diamine (TPD), 4,4',4''-tris(N,N-diphenylamino)triphenylamine (TDATA), 4,4',4''-tris[N-(3-methylphenyl)-N-phenylamino]triphenylamine (m-MTDATA), and 4,4'-bis[N-(spiro-9,9'-bifluoren-2-yl)-N-phenylamino]-1,1'-biphenyl (BSPB). These substances described here mainly are substances each having a hole mobility of greater than or equal to $10^{-6}$ cm$^2$/Vs. Any substance other than the above substances may also be used as long as the hole-transporting properties of the substance is higher than the electron-transporting properties thereof. The layer containing a substance having high hole-transporting properties is not limited to a single layer, and may be a stack of two or more layers each containing the aforementioned substance.

Alternatively, a polymer compound such as poly(N-vinylcarbazole) (PVK) or poly(4-vinyltriphenylamine) (PVTPA) can also be used for the hole-transporting layer 112.

The light-emitting layer 113 is a layer containing a light-emitting substance. In this embodiment mode, the light-emitting layer 113 contains any of the quinoxaline derivatives of the present invention, which are described in Embodiment Mode 1. The quinoxaline derivatives of the present invention can emit blue to green light, and therefore it is preferred that any of the quinoxaline derivatives of the present invention be used as a light-emitting substance.

The electron-transporting layer 114 is a layer containing a substance having high electron-transporting properties. For example, it is possible to employ a layer made of a metal complex or the like having a quinoline or benzoquinoline skeleton, such as tris(8-quinolinolato)aluminum (Alq), tris(4-methyl-8-quinolinolato)aluminum (Almq$_3$), bis(10-hydroxybenzo[h]quinolinato)beryllium (BeBq$_2$), or bis(2-methyl-8-quinolinolato)(4-phenylphenolato)aluminum (BAlq). Alternatively, a metal complex or the like having an oxazole-based or thiazole-based ligand, such as bis[2-(2-hydroxyphenyl)benzoxazolato]zinc (Zn(BOX)$_2$) or bis[2-(2-hydroxyphenyl)-benzothiazolato]zinc (Zn(BTZ)$_2$) can be used. Instead of the metal complex, 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ), bathophenanthroline (BPhen), bathocuproine (BCP), or the like can also be used. The substances described here mainly are substances each having an electron mobility of greater than or equal to $10^{-6}$ cm$^2$/Vs. Any substance other than the above substances may also be used as long as the electron-transporting properties of the substance is higher than the hole-transporting properties thereof. Furthermore, the electron-transporting layer is not limited to a single layer, and may be a stack of two or more layers each including the aforementioned substance.

An electron-injecting layer may be provided. The electron-injecting layer can be formed using an alkali metal, an alkaline earth metal, or a compound thereof such as lithium fluoride (LiF), cesium fluoride (CsF), or calcium fluoride (CaF$_2$). For example, it is possible to use a layer made of a substance having electron-transporting properties, in which an alkali metal, an alkaline earth metal, or a compound thereof is included, such as a layer made of Alq in which magnesium (Mg) is included. When a layer made of a substance having electron-transporting properties, in which an alkali metal or an alkaline earth metal is included, is used as the electron-injecting layer, electrons are efficiently injected from the electrode layer, which is preferable.

The second electrode 104 can be formed using any of metal, alloy, and an electrically conductive compound each having a low work function (3.8 eV or lower), a mixture of them, or the like. Specific examples of such cathode materials include elements belonging to Group 1 or 2 of the periodic table, i.e., alkali metals such as lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb), and alloys of them. However, when the electron-injecting layer is provided between the second electrode 104 and the electron-transporting layer, any of various conductive materials such as Al, Ag, ITO, and ITO containing silicon or silicon oxide can be used for the second electrode 104 regardless of its work function. Films of these electrically conductive materials can be formed by a sputtering method, an ink-jet method, a spin coating method, or the like.

Any of various methods can be employed for forming the EL layer 103 regardless of whether it is a dry process or a wet process. For example, a vacuum evaporation method, an ink-jet method, a spin coating method, or the like can be used. Further, different deposition methods may be employed for each electrode or layer.

Similarly, the electrodes may be formed by a wet process such as a sol-gel process or by a wet process using a metal paste. Alternatively, the electrodes may be formed by a dry process such as a sputtering method or a vacuum evaporation method.

In the light-emitting element of the present invention having the structure as described above, the potential difference generated between the first electrode 102 and the second electrode 104 makes a current flow, whereby holes and electrons are recombined in the light-emitting layer 113 that is a layer containing high light-emitting properties and thus light is emitted. That is, a light-emitting region is formed in the light-emitting layer 113.

Figure 1B:
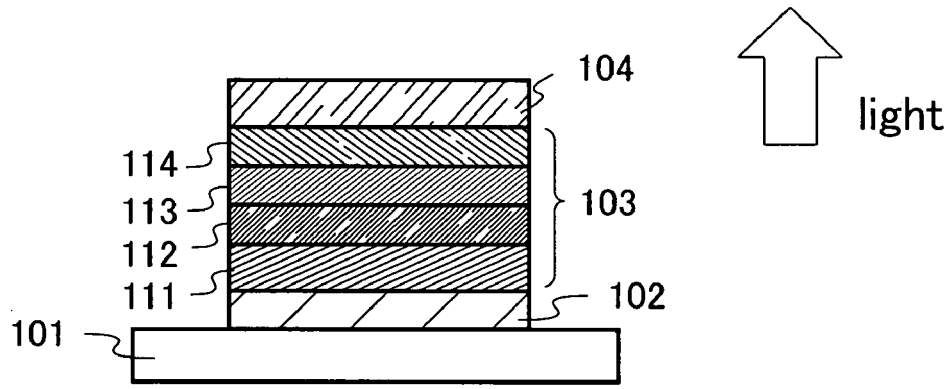
Figure 1C:
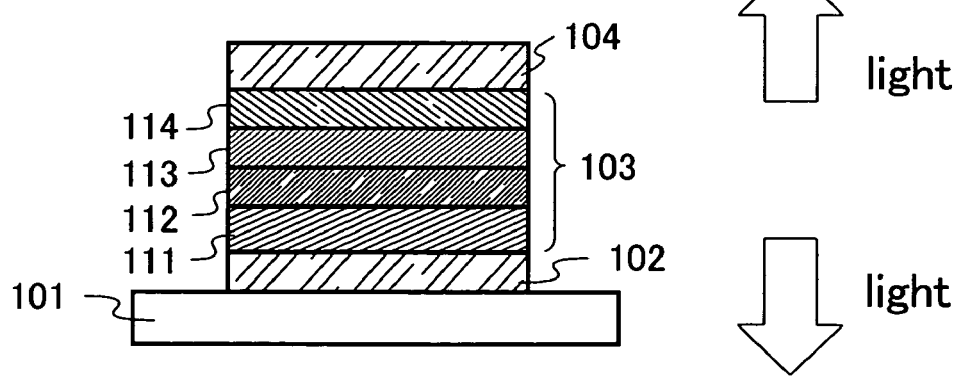

Light is extracted outside through one or both of the first electrode 102 and the second electrode 104. Therefore, one or both of the first electrode 102 and the second electrode 104 are light-transmissive electrodes. When only the first electrode 102 is a light-transmissive electrode, light is extracted from the substrate side through the first electrode 102 (FIG. 1A). In contrast, when only the second electrode 104 is a light-transmissive electrode, light is extracted from the side opposite to the substrate side through the second electrode 104 (FIG. 1B). When both the first electrode 102 and the second electrode 104 are light-transmissive electrodes, light is extracted from both the substrate side and the side opposite to the substrate side through the first electrode 102 and the second electrode 104 (FIG. 1C).

The structure of the layers provided between the first electrode 102 and the second electrode 104 is not limited to the above, and may be any structure as long as the light-emitting region for recombination of holes and electrons is positioned away from the first electrode 102 and the second electrode 104 so as to suppress quenching which would otherwise be caused by the proximity of the light-emitting region to metal.

That is, there is no particular limitation on the stacked structure of the layers. It is acceptable as long as the layer containing any of the quinoxaline derivatives of the present invention is freely combined with the layers each including a substance having high electron-transporting properties, a substance having high hole-transporting properties, a substance having high electron-injecting properties, a substance having high hole-injecting properties, or a bipolar substance (a substance having high electron-transporting and hole-transporting properties).

Figure 2:
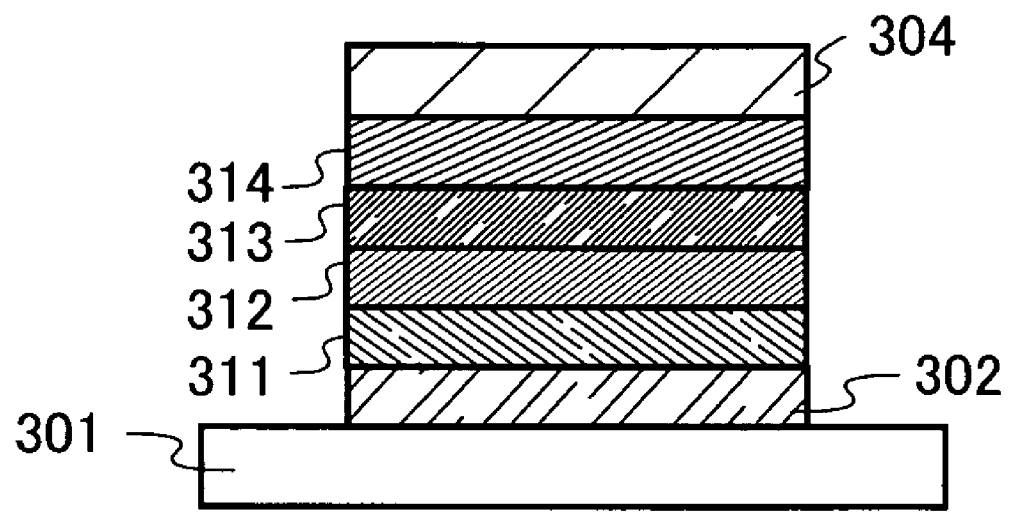
FIG. 2 is a view illustrating a light-emitting element of the present invention.

In a light-emitting element shown in FIG. 2, a first electrode 302 serving as a cathode, an electron-transporting layer 311, a light-emitting layer 312, a hole-transporting layer 313, and a hole-injecting layer 314, and a second electrode 204 serving as an anode are sequentially stacked over a substrate 301.

In this embodiment mode, the light-emitting element is formed over a substrate including glass or plastic. When a plurality of such light-emitting elements are formed over a substrate, a passive matrix light-emitting device can be manufactured. In addition, it is also possible to form, for example, thin film transistors (TFTs) over a substrate including glass or plastic and fabricate light-emitting elements over electrodes that are electrically connected to the TFTs. Accordingly, an active matrix light-emitting device in which drive of the light-emitting elements is controlled by the TFTs can be manufactured. There is no particular limitation on the structure of the TFTs, and either staggered TFTs or inversely staggered TFTs may be employed. Further, there is no particular limitation on the crystallinity of a semiconductor used for forming the TFTs, and either an amorphous semiconductor or a crystalline semiconductor may be used. In addition, a driver circuit formed over a TFT substrate may be formed of either or both n-channel and p-channel TFTs.

The quinoxaline derivatives of the present invention are bipolar and have light-emitting properties, and therefore any of the quinoxaline derivatives of the present invention can be included in the light-emitting layer without other light-emitting substances, as described in this embodiment mode.

Further, since the quinoxaline derivatives of the present invention are bipolar, the light-emitting region is not readily localized at an interface of the stacked layers. Hence, it is possible to provide a high-performance light-emitting element that shows few changes in the emission spectrum and a small decrease in emission efficiency, resulting from interactions such as exciplex formation. Furthermore, a light-emitting element with high emission efficiency can be obtained.

Furthermore, microcrystalline components are hardly included during film formation of the quinoxaline derivatives of the present invention, and thus the film includes few microcrystalline components; accordingly, the amorphous film can be obtained. Therefore, such a film with high quality makes it possible to fabricate a light-emitting element that exhibits fewer element defects such as dielectric breakdown due to electric field concentration The quinoxaline derivatives of the present invention are bipolar and excellent in carrier-transporting properties (both electron-transporting properties and hole-transporting properties); therefore, by using any of the quinoxaline derivatives in a light-emitting element, a driving voltage of the light-emitting element can be reduced, which leads to the reduction in power consumption.

Further, the quinoxaline derivatives of the present invention are stable to repetitive oxidation-reduction or reduction-oxidation reactions. That is, the quinoxaline derivatives are electrochemically stable. Therefore, by using any of the quinoxaline derivatives of the present invention, a long-life light-emitting element can be obtained.

(Embodiment Mode 3)

In this embodiment mode, a light-emitting element having a different structure from that described in Embodiment Mode 2 is described.

The light-emitting layer 113 described in Embodiment Mode 2 contains any of the quinoxaline derivatives of the present invention, which is dispersed in another substance; accordingly, light emission can be obtained from this quinoxaline derivative of the present invention. Since the quinoxaline derivatives of the present invention emit blue to blue green light, a blue to blue green light-emitting element can be obtained.

In this embodiment mode, any of various materials can be used as the substance in which one of the quinoxaline derivatives of the present invention is dispersed. In addition to the substance having high hole-transporting properties and the substance having high electron-transporting properties, which are described in Embodiment Mode 2, 4,4'-di(N-carbazolyl)-biphenyl (CBP), 2,2',2''-(1,3,5-benzenetriyl)-tris[1-phenyl-1H-benzimidazole] (TPBI), 9,10-di(2-naphthyl)anthracene (DNA), 2-tert-butyl-9,10-di(2-naphthyl)anthracene (t-BuDNA), or the like can be used.

The quinoxaline derivatives of the present invention are bipolar and excellent in carrier-transporting properties (electron-transporting properties and hole-transporting properties); therefore, by using any of the quinoxaline derivatives of the present invention for a light-emitting element, a driving voltage of the light-emitting element can be reduced, which leads to the reduction in power consumption.

Further, the quinoxaline derivatives of the present invention are stable to repetitive oxidation-reduction or reduction-oxidation reactions. That is, the quinoxaline derivatives are electrochemically stable. Therefore, a long-life light-emitting element can be obtained by using any of the quinoxaline derivatives of the present invention.

Layers other than the light-emitting layer 113 can have the structures described in Embodiment Mode 2 as appropriate.

(Embodiment Mode 4)

In this embodiment mode, a light-emitting element having a different structure from those described in Embodiment Modes 2 and 3 is described.

When the light-emitting layer 113 described in Embodiment Mode 2 has a structure in which a light-emitting substance is dispersed in any of the quinoxaline derivatives of the present invention, light emission can be obtained from the light-emitting substance.

The quinoxaline derivatives of the present invention are bipolar. Further, microcrystalline components are hardly included during film formation of the quinoxaline derivatives of the present invention and thus the film with a high quality can be obtained. Therefore, it is preferred that any of the quinoxaline derivatives of the present invention be used as a material in which another light-emitting substance is dispersed.

When any of the quinoxaline derivatives of the present invention is used as the material in which another light-emitting substance is dispersed, an emission color depending on the light-emitting substance can be obtained. Further, it is also possible to obtain an emission color that is a mixture of the emission color depending on this quinoxaline derivative of the present invention and the emission color depending on the light-emitting substance dispersed in the quinoxaline derivative.

In this case, any of various materials can be used for the light-emitting substance dispersed in any of the quinoxaline derivatives of the present invention. Specific examples of such materials include fluorescent substances that exhibit fluorescence, such as 4-(dicyanomethylene)-2-methyl-6-p-dimethylaminostyryl)-4H-pyran (DCM1), 4-(dicyanomethylene)-2-methyl-6-(julolidin-4-yl-vinyl)-4H-pyran (DCM2), N,N-dimethylquinacridone (DMQd), 9,10-diphenylanthracene (DPA); 5,12-diphenyltetracene (DPT), coumarin 6, perylene, and rubrene; and phosphorescent substances that exhibit phosphorescence, such as bis(2-phenylbenzothiazolato-N,$C^{2'}$)iridium(III)acetylacetonate (Ir(bt)$_2$(acac)), tris(2-phenylquinolnato-N,$C^{2'}$)iridium(III) (Ir(pq)$_3$), bis(2-phenylquinolinato-N,$C^{2'}$)iridium(III) acetylacetonate (Ir(pq)$_2$(acac)), bis[2-(2'-benzo[4,5-α]thienyl)pyridinato-N,$C^{3'}$]iridium(III)acetylacetonate (Ir(btp)$_2$(acac)), bis(1- phenylisoquinolinato-N,C$^{2'}$)iridium(III)acetylacetonate (Ir(piq)$_2$(acac)), (acetylacetonato)bis[2,3-bis(4-fluorophenyl)quinoxalinato]iridium(III) (Ir(Fdpq)$_2$(acac)), and (2,3,7,8,12,13,17,18-octaethyl-21H,23H-porphyrinato)platinum(II) (PtOEP). In the case of using a phosphorescent substance as the light-emitting substance to be dispersed, it is preferable that an emission spectrum of the phosphorescent substance have a peak at 560 to 700 nm. In the case of using the fluorescent substance, it is preferable that an emission spectrum of the phosphorescent substance have a peak at 500 to 700 nm, and more preferably, 500 to 600 nm.

The quinoxaline derivatives of the present invention are bipolar and excellent in carrier-transporting properties (both electron-transporting properties and hole-transporting properties); therefore, by using any of the quinoxaline derivative of the present invention for a light-emitting element, a driving voltage of the light-emitting element can be reduced, which leads to the reduction in power consumption.

Further, since the quinoxaline derivatives of the present invention are bipolar, the light-emitting region is not readily localized at an interface of the stacked layers. Hence, it is possible to provide a high-performance light-emitting element that shows few changes in the emission spectrum and a small decrease in emission efficiency, resulting from interactions such as exciplex formation.

Further, since the quinoxaline derivatives of the present invention are bipolar, a light-emitting region is not readily localized at an interface of stacked films. Therefore, in the case where a phosphorescent substance that exhibits phosphorescence is used, T-T annihilation can be prevented. Accordingly, a light-emitting element with high emission efficiency can be obtained.

Further, the quinoxaline derivatives of the present invention are stable to repetitive oxidation-reduction or reduction-oxidation reactions. That is, the quinoxaline derivatives are electrochemically stable. Therefore, a long-life light-emitting element can be obtained by using any of the quinoxaline derivatives of the present invention.

Layers other than the light-emitting layer 113 can have the structures described in Embodiment Mode 2 as appropriate.
(Embodiment Mode 5)

In this embodiment mode, a mode of a light-emitting element in which a plurality of light-emitting units according to the present invention are stacked (hereinafter, referred to as a stacked-type element) is described with reference to FIG. 3. The light-emitting element is a stacked-type light-emitting element including a plurality of light-emitting units between a first electrode and a second electrode. The light-emitting units can be similar to the EL layer 103 described in Embodiment Mode 2. That is, a light-emitting element including one light-emitting unit is described in Embodiment Mode 2, and a light-emitting element including a plurality of light-emitting units is described in this embodiment mode.

Figure 3:
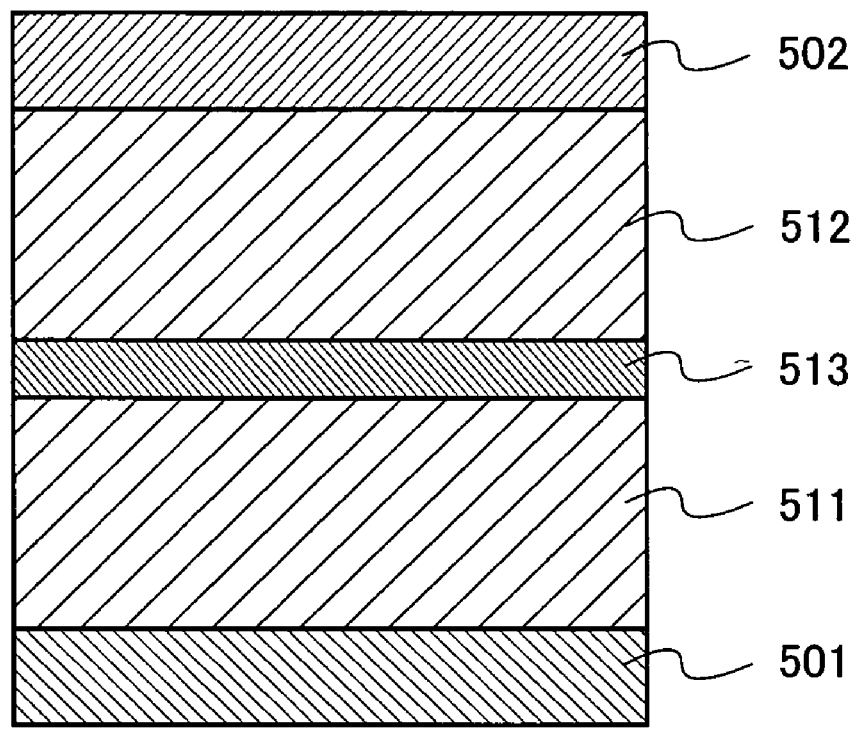
FIG. 3 is a view illustrating a light-emitting element of the present invention.

In FIG. 3, a first light-emitting unit 511 and a second light-emitting unit 512 are stacked between a first electrode 501 and a second electrode 502. A charge generation layer 513 is provided between the first light-emitting unit 511 and the second light-emitting unit 512. The first electrode 501 and the second electrode 502 can be similar to the electrodes shown in Embodiment Mode 2. The first light-emitting unit 511 and the second light-emitting unit 512 may have either the same structure or a different structure, which can be similar to those shown in Embodiment Modes 2 to 4.

The charge generation layer 513 may contain a composite material of an organic compound and metal oxide. This composite material of an organic compound and metal oxide has been described in Embodiment Mode 2 and contains an organic compound and metal oxide such as vanadium oxide, molybdenum oxide, or tungsten oxide. As the organic compound, any of various compounds such as an aromatic amine compound, a carbazole derivative, aromatic hydrocarbon, and a polymer compound (e.g., oligomer, dendrimer, or polymer) can be used. The compound having a hole mobility of greater than or equal to $1\times10^{-6}$ cm$^2$/Vs is preferably applied as the organic compound having hole-transporting properties. Any substance other than the above compounds may also be used as long as the hole-transporting properties of the substance is higher than the electron-transporting properties thereof. A composite of an organic compound with metal oxide is excellent in carrier-injecting properties and carrier-transporting properties, and hence low-voltage driving and low-current driving can be achieved.

The charge generation layer 513 may be formed by a combination of a layer containing the composite material of an organic compound and metal oxide with a layer containing another material. For example, the charge generation layer 513 may be formed by a combination of the layer containing the composite material of an organic compound and metal oxide with a layer containing one compound selected from electron donating substances and a compound having high electron-transporting properties. Alternatively, the charge generation layer 513 may be formed by a combination of a transparent conductive film with a layer containing the composite material of an organic compound and metal oxide.

The charge generation layer 513 interposed between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, the following is acceptable: in FIG. 3, the charge generation layer 513 injects electrons to the first light-emitting unit 511 and injects hole to the second light-emitting unit 512 when a voltage is applied so that the potential of the first electrode is higher than that of the second electrode.

In this embodiment mode, the light-emitting element having two light-emitting units is described; however, the present invention can be similarly applied to a light-emitting element in which three or more light-emitting units are stacked. When a plurality of light-emitting units are arranged between a pair of electrodes so that two of the light-emitting units are partitioned with a charge generation layer, like the light-emitting element according to this embodiment mode, the element emits light with a high luminance while a Low current density is maintained and thus can have a long life. When the light-emitting element is applied to lighting, a voltage drop which would be caused by the resistance of the electrode materials can be suppressed, and thus uniform emission in a large area can be realized. Furthermore, a light-emitting device that can drive at a low voltage and consumes low power can be achieved.

When emission colors vary depending on each light-emitting unit, a desired emission color can be obtained from the light-emitting element as a whole. For example, it is possible to obtain a light-emitting element having two light-emitting units, from which white light is emitted as a whole, when an emission color of the first light-emitting unit and an emission color of the second light-emitting unit are complementary colors. It is to be noted that the complementary colors refer to colors that can produce an achromatic color when they are mixed. That is, white light emission can be obtained by mixture of light from substances, of which the emission colors are complementary colors. The same can be said for a light-emitting element having three light-emitting units. For example, white light can be obtained from the light-emitting element as a whole when emission colors of the first, second, and third light-emitting units are red, green, and blue, respectively.

This embodiment mode can be combined with other embodiment modes as appropriate.

(Embodiment Mode 6)

In this embodiment mode, a mode in which any of the quinoxaline derivatives of the present invention is used for an active layer of a vertical transistor (SIT) which is one kind of an organic semiconductor element is exemplified.

Figure 4:
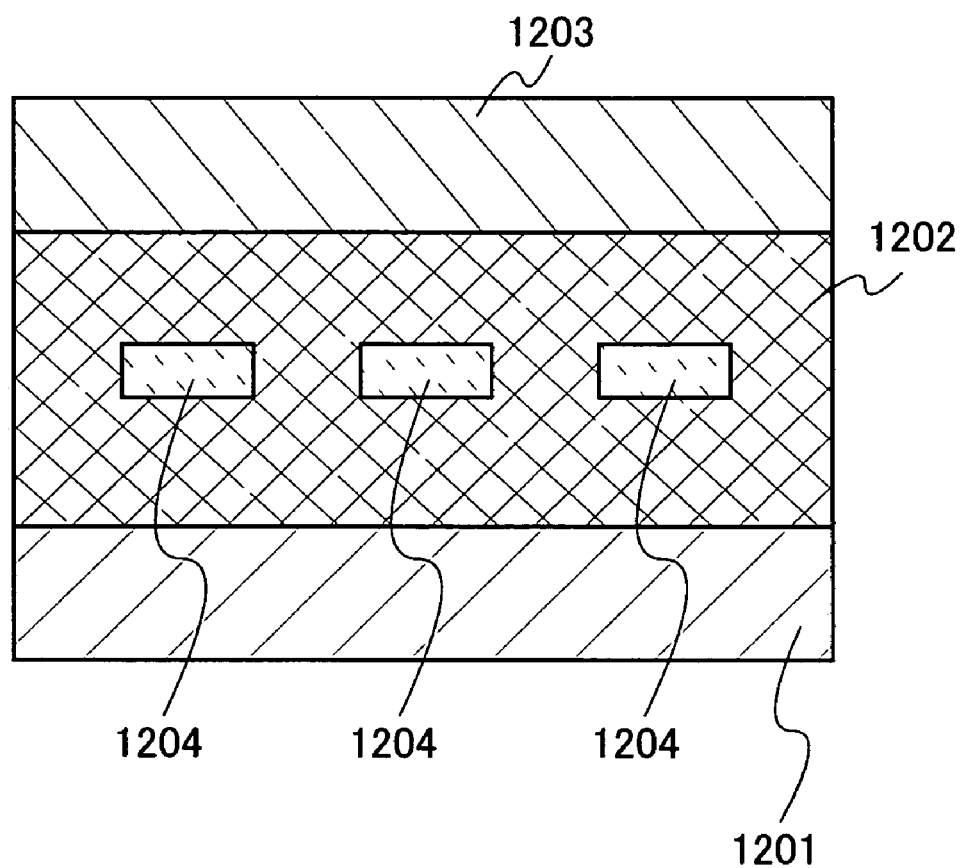
FIG. 4 is a view illustrating an organic semiconductor element of the present invention.

FIG. 4 is a cross-sectional view of the element structure in which a thin active layer 1202 containing any of the quinoxaline derivatives of the present invention is interposed between a source electrode 1201 and a drain electrode 1203, and a gate electrode 1204 is embedded in the active layer 1202. The gate electrode 1204 is electrically connected to a unit to apply a gate voltages and the source electrode 1201 and the drain electrode 1203 are electrically connected to a unit to control the voltage between the source and the drain.

In such an element structure, when a voltage is applied between the source and the drain under the condition where a gate voltage is not applied, a current flows (an ON state). Then, when a gate voltage is applied in this state, a depletion layer is generated in the periphery of the gate electrode 1204, and thus a current does not flow (an OFF state). With such a mechanism, the element operates as a transistor.

In a similar manner to a light-emitting element, the active layer of the vertical transistor should be formed using a material having both carrier-transporting properties and an excellent film quality. The quinoxaline derivatives of the present invention are useful because they sufficiently meet the requirement of such a material.

(Embodiment Mode 7)

In this embodiment mode, a light-emitting device manufactured using any of the quinoxaline derivatives of the present invention is described.

In this embodiment mode, a light-emitting device manufactured using any of the quinoxaline derivatives of the present invention is described with reference to FIGS. 5A and 5B. FIG. 5A is a top view of a light-emitting device and FIG. 5B is a cross-sectional view of FIG. 5A, taken along lines A-A' and B-B'. This light-emitting device includes a driver circuit portion (a source side driver circuit) 601; a pixel portion 602; and a driver circuit portion (a gate side driver circuit) 603, which are indicated by dotted lines, so as to control light emission from the light-emitting elements. Reference numeral 604 denotes a sealing substrate; reference numeral 605 denotes a sealing material; and a portion surrounded by the sealing material 605 corresponds to a space 607.

A lead wiring 608 is a wiring for transmitting signals to be inputted to the source side driver circuit 601 and the gate side driver circuit 603. The wiring 608 receives a video signal, a clock signal, a start signal, a reset signal, and the like from a flexible printed circuit (FPC) 609 which is an external input terminal. Although only the FPC is shown here, the FPC may be provided with a printed wiring board (PWB). The category of the light-emitting device in this specification includes not only a light-emitting device itself but also a light-emitting device attached with the FPC or the PWB.

Next, a cross-sectional structure is described with reference to FIG. 51B. Although the driver circuit portions and the pixel portion are formed over an element substrate 610, FIG. 5B shows one pixel in the pixel portion 602 and the source side driver circuit 601 which is one of the driver circuit portions.

A CMOS circuit, which is a combination of an n-channel TFT 623 with a p-channel TFT 624, is formed as the source side driver circuit 601. Each driver circuit portion may be any of various circuits such as a CMOS circuit, PMOS circuit, and an NMOS circuit. Although a driver integration type in which a driver circuit is formed over a substrate is described in this embodiment mode, a driver circuit is not necessarily formed over a substrate and can be formed outside a substrate.

The pixel portion 602 has a plurality of pixels, each of which includes a switching TFT 611, a current control TFT 612, and a first electrode 613 which is electrically connected to a drain of the current control TFT 612. An insulator 614 is formed so as to cover end portions of the first electrode 613. In this case, the insulator 614 is formed using a positive photosensitive acrylic resin film.

The insulator 614 is formed so as to have a curved surface having curvature at an upper end portion or lower end portion thereof in order to make the coverage favorable. For example, in the case of using positive photosensitive acrylic as a material for the insulator 614, it is preferable that the insulator 614 be formed so as to have a curved surface with a curvature radius (0.2 μm to 3 μm) only at the upper end portion thereof. The insulator 614 can be formed using either a negative type which becomes insoluble in an etchant by light irradiation or a positive type which becomes soluble in an etchant by light irradiation.

An EL layer 616 and a second electrode 617 are formed over the first electrode 613. In this case, it is preferred that the first electrode 613 serving as an anode be formed using a high-work function material. For example, the first electrode 613 can be formed using a single-layer film of an ITO film, an indium tin oxide film containing silicon, an indium oxide film containing 2 to 20 wt % of zinc oxide, a titanium nitride film, a chromium film, a tungsten film, a Zn film, a Pt film, or the like; a stack of a titanium nitride film and a film containing aluminum as its main component; a three-layer structure of a titanium nitride film, a film containing aluminum as its main component, and another titanium nitride film; or the like. When the first electrode 613 has a stacked structure, it can have low resistance as a wiring, form a favorable ohmic contact, and further function as an anode.

The EL layer 616 is formed by any of various methods such as an evaporation method using an evaporation mask, an ink-jet method, and a spin coating method. The EL layer 616 contains any of the quinoxaline derivatives of the present invention described in Embodiment Mode 1. Further, the EL layer 616 may be formed using another material such as a low molecular weight compound or a polymer compound (a category of the high molecular weight compound includes an oligomer and a dendrimer).

As a material used for the second electrode 617 which is formed over the EL layer 616 and serves as a cathode, it is preferable that a low-work function material (e.g., Al, Mg, Li, Ca, or an alloy or compound thereof such as MgAg, Mg—In, Al—Li, LiF, or $CaF_2$) be used. In the case where light generated in the EL layer 616 is transmitted through the second electrode 617, the second electrode 617 may be formed of a stack of a metal thin film and a transparent conductive film (e.g., ITO, indium oxide containing 2 to 20 wt % of zinc oxide, indium tin oxide containing silicon, or zinc oxide (ZnO)). The sealing substrate 604 is attached to the element substrate 610 with the sealing material 605; thus, a light-emitting element 618 is provided in the space 607 surrounded by the element substrate 610, the sealing substrate 604, and the sealing material 605. The space 607 is filled with a filler such as an inert gas (e.g., nitrogen or argon) or the sealing material 605.

It is preferable that the sealing material 605 be formed of any of epoxy-based resins and such materials permeate little moisture and oxygen as much as possible. The sealing substrate 604 can be formed of a glass substrate; a quartz substrate; or a plastic substrate including fiberglass-reinforced plastics (FRP), polyvinyl fluoride (PVF), polyester, acrylic, or the like.

Accordingly, a light-emitting device manufactured using any of the quinoxaline derivatives of the present invention can be obtained.

Since any of the quinoxaline derivatives which are described in Embodiment Mode 1 is used for the light-emitting device of the present invention, a light-emitting device having favorable characteristics can be obtained. Specifically, a light-emitting device with low power consumption can be obtained.

The quinoxaline derivatives of the present invention are bipolar and excellent in carrier-transporting properties (both electron-transporting properties and hole-transporting properties); therefore, by using any of the quinoxaline derivatives of the present invention for a light-emitting element, a driving voltage of the light-emitting element can be reduced, which leads to the reduction in power consumption. In particular, when a phosphorescent substance is used as a light-emitting substance, a light-emitting device with high emission efficiency and further reduced power consumption can be obtained.

Further, since the quinoxaline derivatives of the present invention are electrochemically stable, a long-life light-emitting device can be obtained.

Figure 6A:
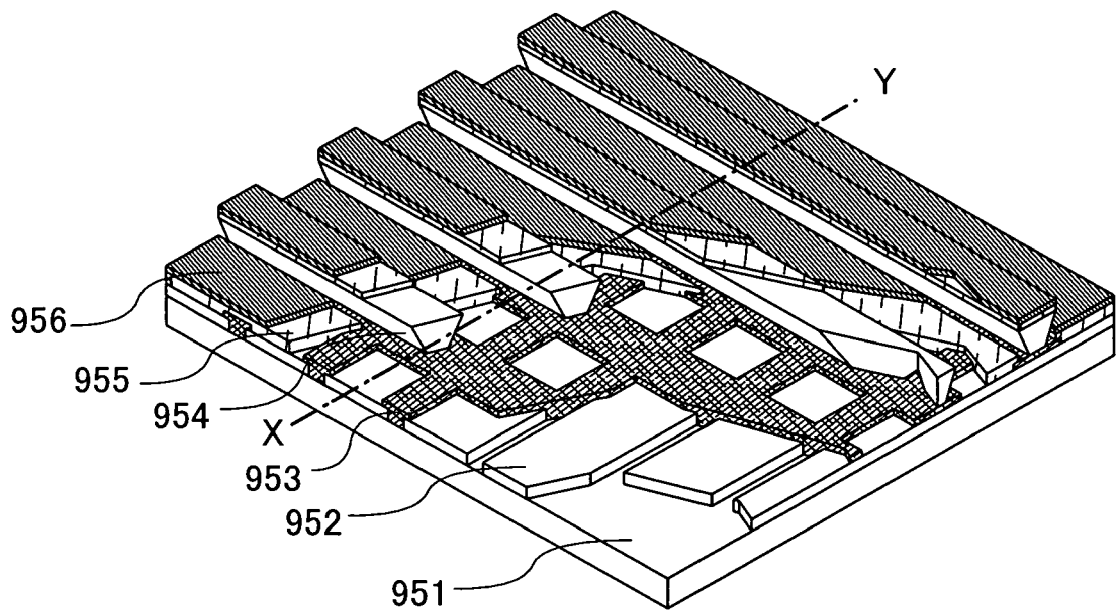
FIGS. 6A and 6B are views illustrating a light-emitting device of the present invention.
Figure 6B:
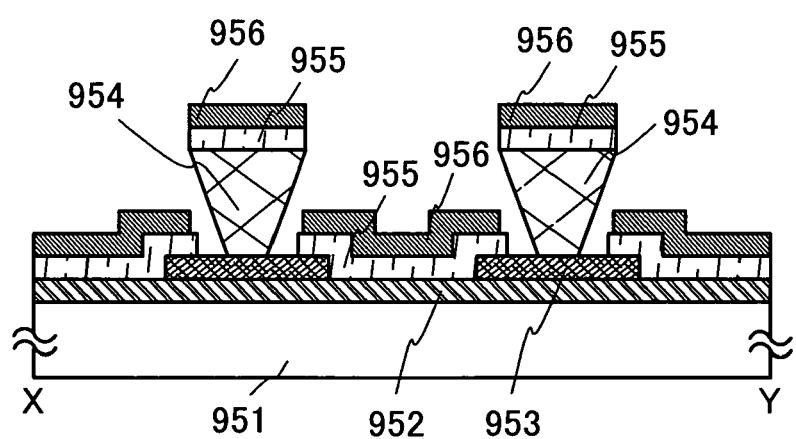

As described above, this embodiment mode describes an active matrix light-emitting device in which operation of a light-emitting element is controlled by transistors, which may be replaced with a passive matrix light-emitting device. FIGS. 6A and 6B show a passive matrix light-emitting device to which the present invention is applied. FIG. 6A is a perspective view of the light-emitting device, and FIG. 6B is a cross-sectional view taken along a line X-Y of FIG. 6A. In FIGS. 6A and 6B, an EL layer 955 is provided between an electrode 952 and an electrode 956 over a substrate 951. End portions of the electrode 952 are covered with an insulating layer 953. Then, a partition layer 954 is provided over the insulating layer 953. A side wall of the partition layer 954 slopes so that a distance between one side wall and the other side wall becomes narrow toward the substrate surface. In other words, a cross section taken in the direction of the short side of the partition layer 954 is trapezoidal, and the base of the cross-section (a side facing in the same direction as a plane direction of the insulating layer 953 and in contact with the insulating layer 953) is shorter than the upper side thereof (a side facing in the same direction as the plane direction of the insulating layer 953 and not in contact with the insulating layer 953). The partition layer 954 provided in this manner can prevent the light-emitting element from being defective due to static electricity or the like. The passive matrix light-emitting device can also be driven with low power consumption when it includes the light-emitting element of the present invention, which operates at a low driving voltage.

(Embodiment Mode 8)

In this embodiment mode, electronic devices of the present invention, each including the light-emitting device described in Embodiment Mode 7, are described. The electronic devices of the present invention each contain any of the quinoxaline derivatives described in Embodiment Mode 1 and include a display portion with reduced power consumption and a long life.

Examples of the electronic devices each including the light-emitting element fabricated using any of the quinoxaline derivatives of the present invention include cameras such as video cameras or digital cameras, goggle type displays, navigation systems, audio reproducing devices (e.g., car audio components and audio components), computers, game machines, portable information terminals (e.g., mobile computers, cellular phones, portable game machines, and e-book readers), and image reproducing devices each provided with recording media (specifically, devices capable of reproducing a recording medium such as a digital versatile disc (DVD) and provided with a display device that can display the image). Specific examples of these electronic devices are illustrated in FIGS. 7A to 7D.

Figure 7A:
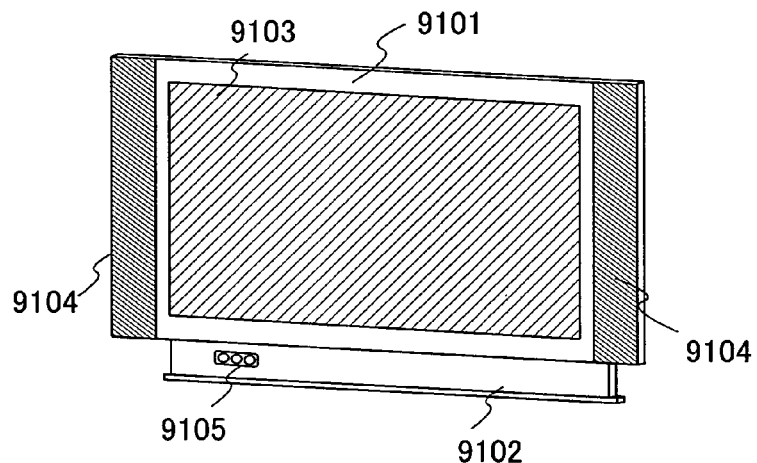
FIGS. 7A to 7D are views each illustrating an electronic device of the present invention.

FIG. 7A shows a television device according to the present invention, which includes a chassis 9101, a supporting base 9102, a display portion 9103, a speaker portion 9104, and a video input terminal 9105. In the television device, the display portion 9103 includes light-emitting elements similar to those described in Embodiment Modes 2 to 5, which are arranged in matrix. The light-emitting elements are characterized by their capability of driving at a low voltage, and having a long life. The display portion 9103 which includes the light-emitting elements has similar characteristics. Therefore, the television device has little deterioration in an image quality and consumes low power. Such characteristics can dramatically reduce or downsize deterioration compensation function circuits and power supply circuits in the television device; therefore, the chassis 9101 and the supporting base 9102 can be reduced in size and weight. In the television device according to the present invention, low power consumption, high image quality, and reduction in size and weight are achieved; therefore, a product suitable for living environment can be provided.

Figure 7B:
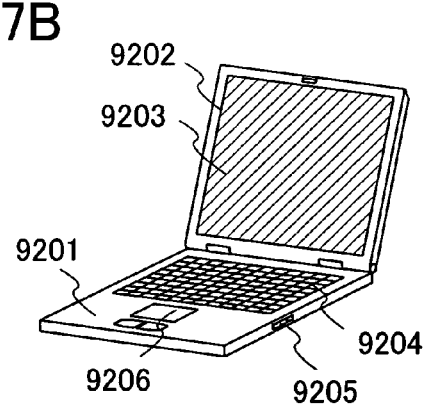

FIG. 7B shows a computer according to the present invention, which includes a main body 9201, a chassis 9202, a display portion 9203, a keyboard 9204, an external connection port 9205, and a pointing device 9206. In the computer, the display portion 9203 includes light-emitting elements similar to those described in Embodiment Modes 2 to 5, which are arranged in matrix. The light-emitting elements are characterized by their capability of driving at a low voltage, and having a long life. The display portion 9203 which includes the light-emitting elements has similar characteristics. Therefore, the computer has little deterioration in an image quality and consumes low power. Such characteristics can dramatically reduce or downsize deterioration compensation function circuits and power supply circuits in the computer; therefore, the main body 9201 and the chassis 9202 can be reduced in size and weight. In the computer according to the present invention, low power consumption, high image quality, and reduction in size and weight are achieved; therefore, a product suitable for the environment can be provided.

Figure 7C:
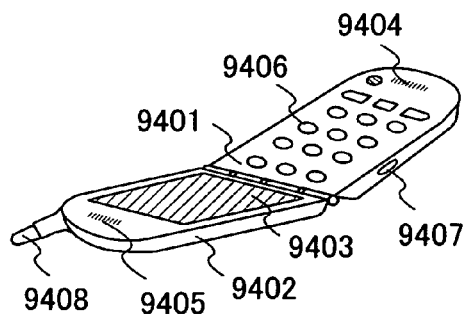
Figure 7D:
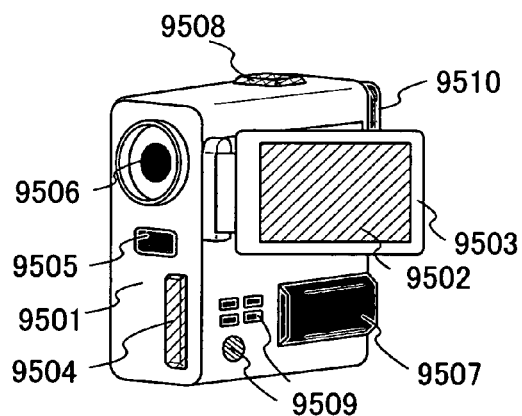

FIG. 7C shows a cellular phone according to the present invention, which includes a main body 9401, a chassis 9402, a display portion 9403, an audio input portion 9404, an audio output portion 9405, an operation key 9406, an external connection port 9407, and an antenna 9408. In the cellular phone, a display portion 9403 includes light-emitting elements similar to those described in Embodiment Modes 2 to 5, which are arranged in matrix. The light-emitting elements are characterized by their capability of driving at a low voltage, and having a long life. The display portion 9403 which includes the light-emitting elements has similar characteristics. Therefore, the cellular phone has little deterioration in an image quality and consumes low power. Such characteristics can dramatically reduce or downsize deterioration compensation function circuits and power supply circuits in the cellular phone; therefore, the main body 9401 and the chassis 9402 can be reduced in size and weight. In the cellular phone according to the present invention, low power consumption, high image quality, and a small size and lightweight are achieved; therefore, a product suitable for carrying can be provided.

FIG. 1D shows a camera according to the present invention, which includes a main body 9501, a display portion 9502, a chassis 9503, an external connection port 9504, a remote control receiving portion 9505, an image receiving portion 9506, a battery 9507, an audio input portion 9508, operation keys 9509, and an eye piece portion 9510. In the camera, the display portion 9502 includes light-emitting elements similar to those described in Embodiment Modes 2 to 5, which are arranged in matrix. The light-emitting elements are characterized by their capability of driving at a low voltage, and having a long life. The display portion 9502 which includes the light-emitting elements has similar characteristics. Therefore, the camera has little deterioration in an image quality and consumes low power. Such characteristics can dramatically reduce or downsize deterioration compensation function circuits and power supply circuits in the camera; therefore, the main body 9501 can be reduced in size and weight. In the camera according to the present invention, low power consumption, high image quality, and reduction in size and weight are achieved; therefore, a product suitable for carrying can be provided.

As described above, the applicable range of the light-emitting device of the present invention is so wide that the light-emitting device can be applied to electronic devices in various fields. By using any of the quinoxaline derivatives of the present invention, an electronic device including a display portion with low power consumption and a long life can be provided.

The light-emitting device of the present invention can also be used as a lighting device. One mode using the light-emitting device of the present invention as the lighting device is described with reference to FIG. 8.

Figure 8:
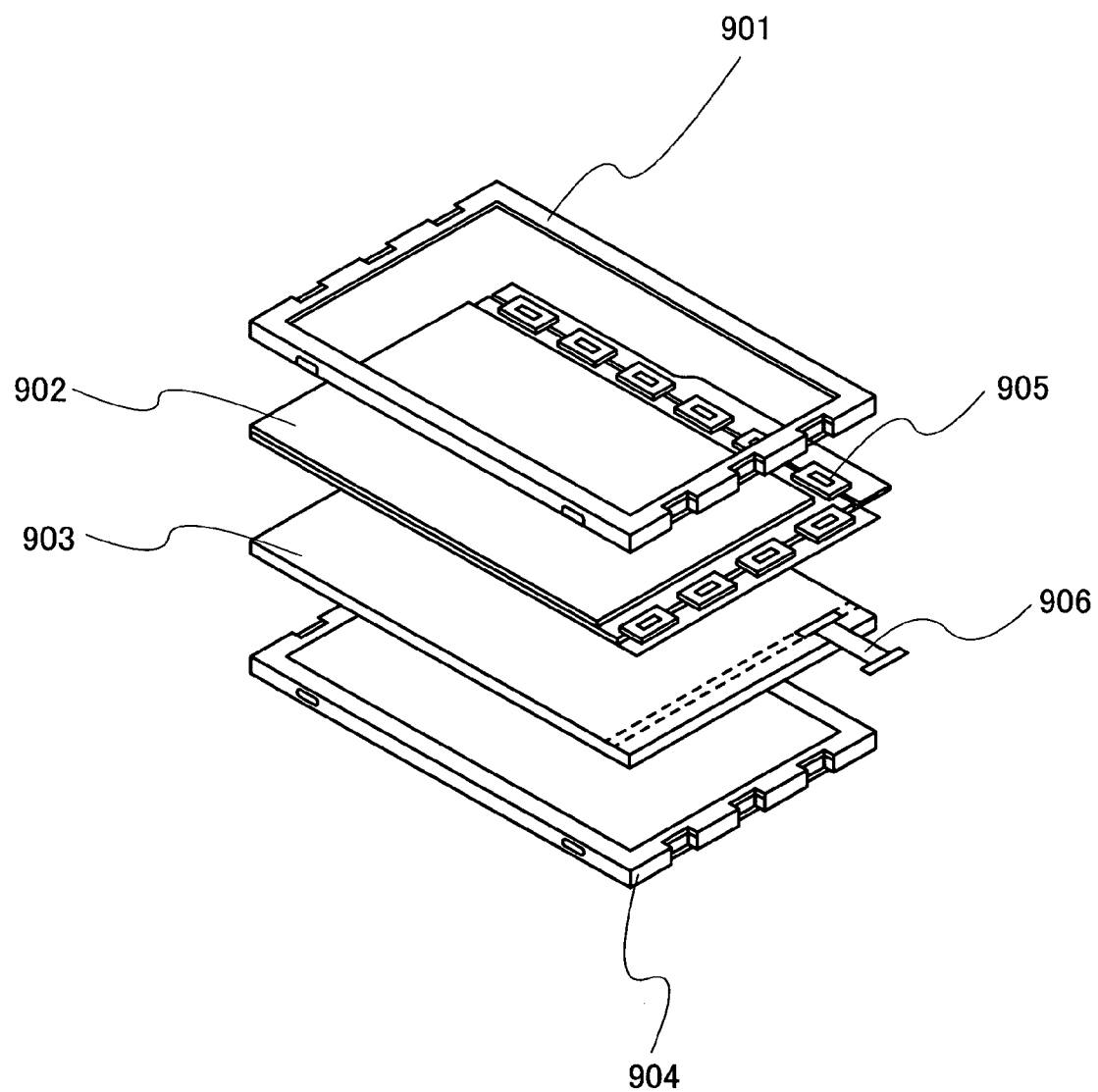
FIG. 8 is a view illustrating an electronic device of the present invention.

FIG. 8 shows an example of a liquid crystal display device using the light-emitting device of the present invention as a backlight. The liquid crystal display device shown in FIG. 8 includes a chassis 901, a liquid crystal layer 902, a backlight 903, and a chassis 904. The liquid crystal layer 902 is connected to a driver IC 905. The light-emitting device of the present invention is used as the backlight 903, and a current is supplied through a terminal 906.

When the light-emitting device of the present invention is used as the backlight of the liquid crystal display device, the backlight can reduce its power consumption. The light-emitting device of the present invention is a lighting device with plane emission area and this emission area can be readily increased; accordingly, it is possible that the backlight has a larger emission area and the liquid crystal display device has a larger display area. Furthermore, the light-emitting device of the present invention has a thin shape and consumes low power; thus, the display device can also be reduced in thickness and power consumption. Moreover, the light-emitting device of the present invention has a long life, and thus a liquid crystal display device including the light-emitting device of the present invention also has a long life.

Figure 9:
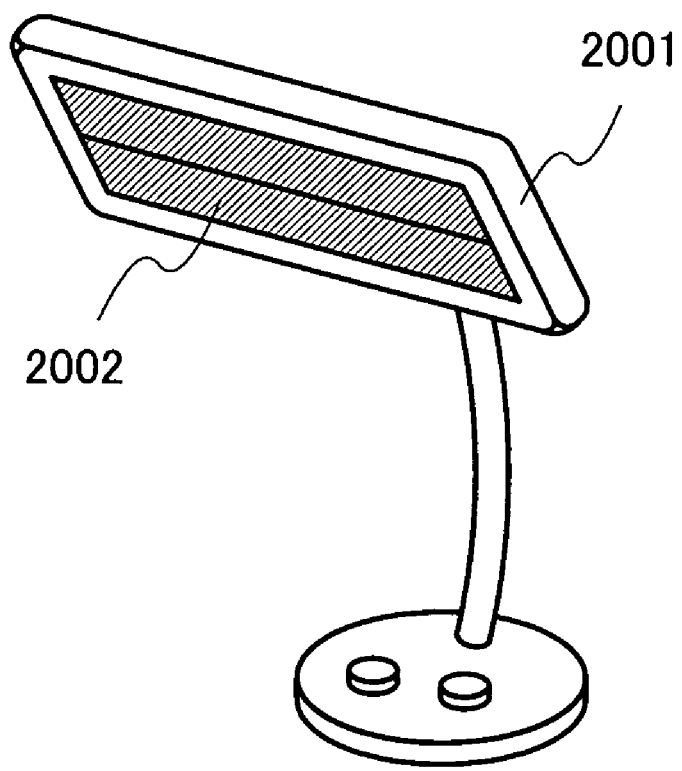
FIG. 9 is a view illustrating a lighting device of the present invention.

FIG. 9 shows an example using the light-emitting device of the present invention as a table lamp that is a lighting device. A table lamp shown in FIG. 9 has a chassis 2001 and a light source 2002, and the light-emitting device of the present invention is used as the light source 2002. The light-emitting device of the present invention can emit light with high luminance, and thus it can illuminate the area where detail work or the like is being done.

Figure 10:
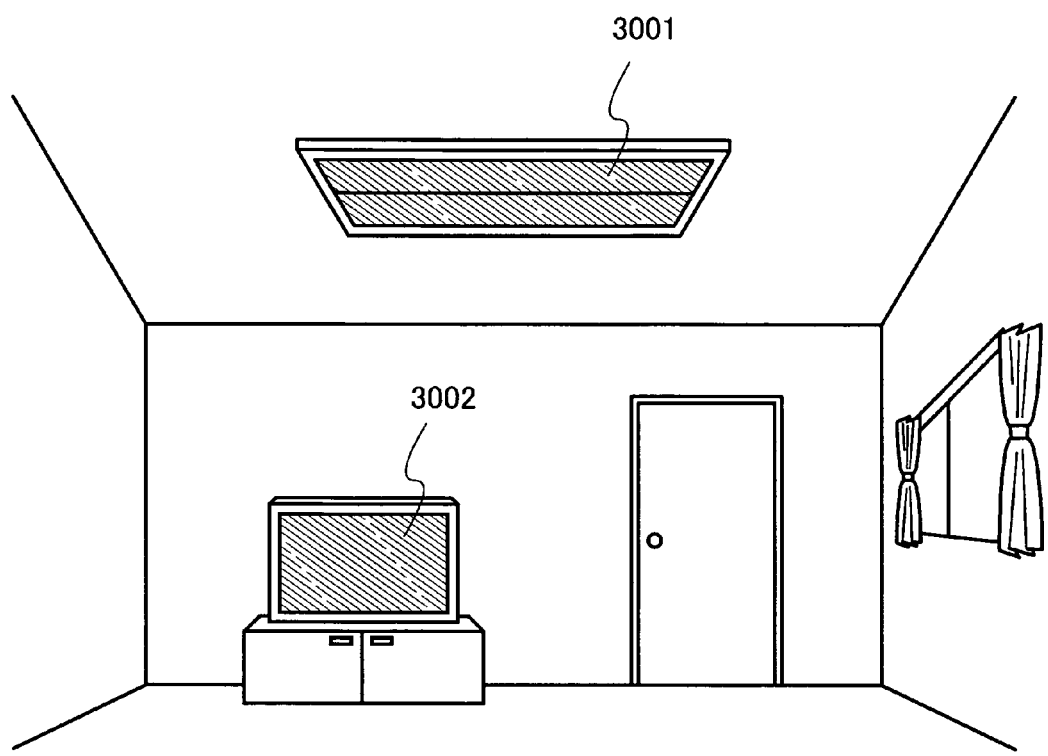
FIG. 10 is a view illustrating a lighting device of the present invention.

FIG. 10 shows an example using the light-emitting device of the present invention as an indoor lighting device 3001. Since the light-emitting device of the present invention can have a larger emission area, the light-emitting device of the present invention can be used as a lighting device having a larger emission area. Further, the light-emitting device of the present invention has a thin shape and consumes low power; therefore, the light-emitting device of the present invention can be used as a lighting device having a thin shape and consuming low power. A television device according to the present invention as described in FIG. 7A is placed in a room in which the present invention is applied to the indoor lighting device 3001 as a light-emitting device; thus, public broadcasting and movies can be watched. In such a case, since both of the devices consume low power, a powerful image can be watched in a bright room without concern about electricity charges.

Example 1

This example exemplifies a synthetic method of the quinoxaline derivative of the present invention represented by the following structural formula (102), 2-{4-[N-(biphenyl-4-yl)-N-phenylamino]phenyl}-3-phenylquinoxaline (BPA1PQ).

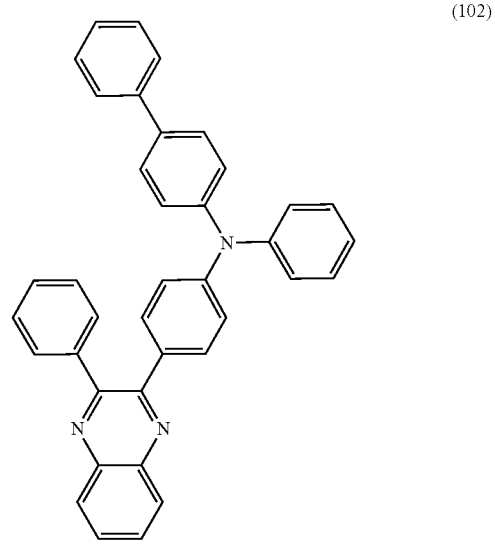

(102)

A synthetic method of BPA1PQ is described. A synthetic scheme of BPA1PQ is shown in (B-1).

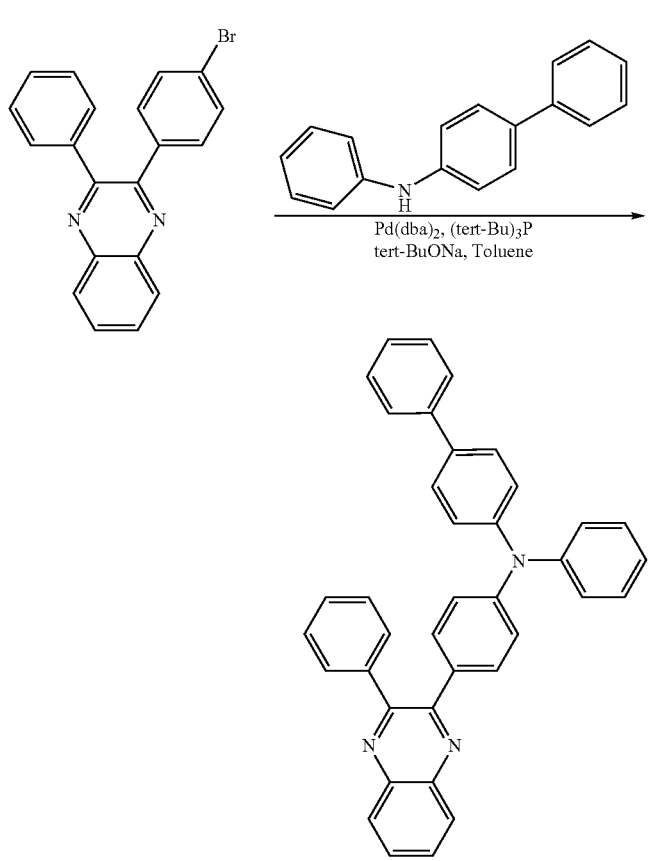

(B-1)

2-(4-bromophenyl)-3-phenylquinoxaline (1.5 g, 4.2 mmol), sodium tert-butoxide (1.0 g, 10 mmol), 4-phenyldiphenylamine (1.0 g, 4.2 mmol), and bis(dibenzylideneacetone)palladium(0) (0.10 g, 0.20 mmol) are put into a 50 mL three-neck flask, and the air in the flask is replaced with nitrogen. To the mixture are added toluene (20 mL) and a 10 wt % hexane solution of tri(tert-butyl)phosphine (0.1 mL). This mixture is heated and stirred at 80° C. for 5 hours to be reacted. After the reaction, toluene is added to the reaction mixture, and this suspension is subjected to suction filtration through Florisil (produced by Wako Pure Chemical Industries, Ltd., Catalog No. 540-00135), celite (produced by Wako Pure Chemical Industries, Ltd., Catalog No. 531-16855) and alumina. The obtained filtrate is washed with a saturated sodium hydrogen carbonate solution and a saturated saline solution in this order. Magnesium sulfate is added to the organic layer that has been separated from the aqueous layer so that the organic layer is dried. This mixture is subjected to suction filtration in order to remove the magnesium sulfate. The obtained filtrate is concentrated, and then a solid is obtained. This solid is recrystallized with a mixed solvent of chloroform and hexane to give 1.2 g of a yellow powdered solid (55% yield). Nuclear magnetic resonance measurement (NMR) confirms that this compound is BPA1PQ.

The obtained yellow solid (1.2 g) is sublimed for purification by train sublimation, which is carried out under reduced pressure of 7.0 Pa, with a flow rate of argon at 3 mL/min, at 233° C. for 15 hours to give 0.93 g of the resultant solid (78% yield).

Figure 11A:
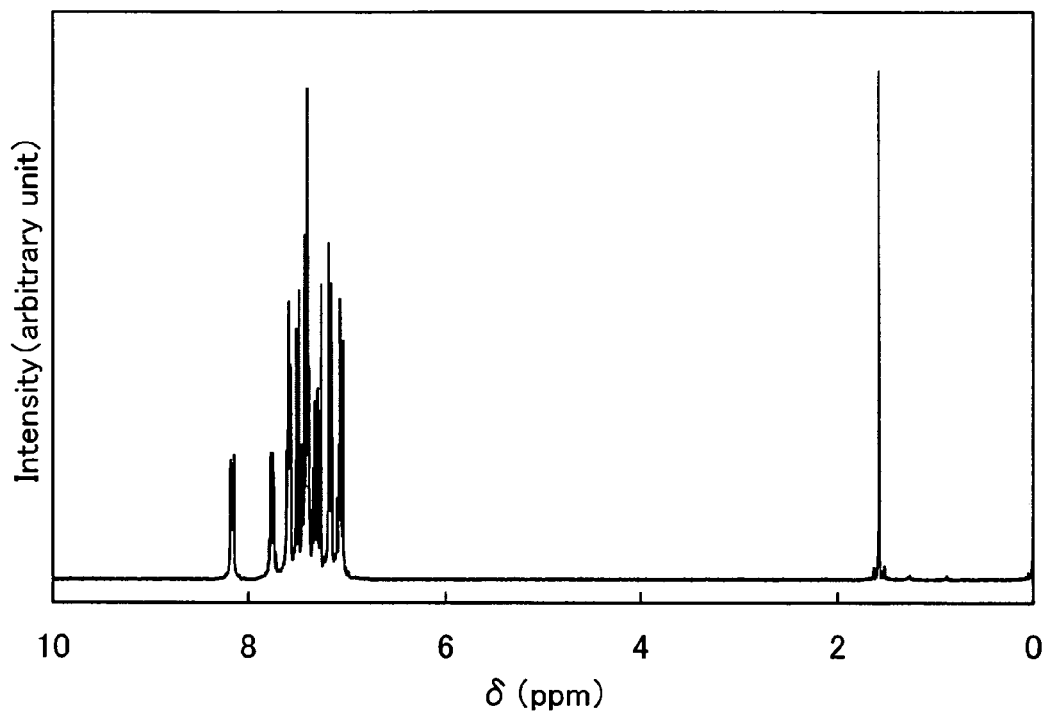
FIGS. 11A and 11B are $^1$H NMR charts of 2-{4-[N-(biphenyl-4-yl)-N-phenylamino]phenyl}-3-phenylquinoxaline (BPA1PQ) which is a quinoxaline derivative of the present invention.
Figure 11B:
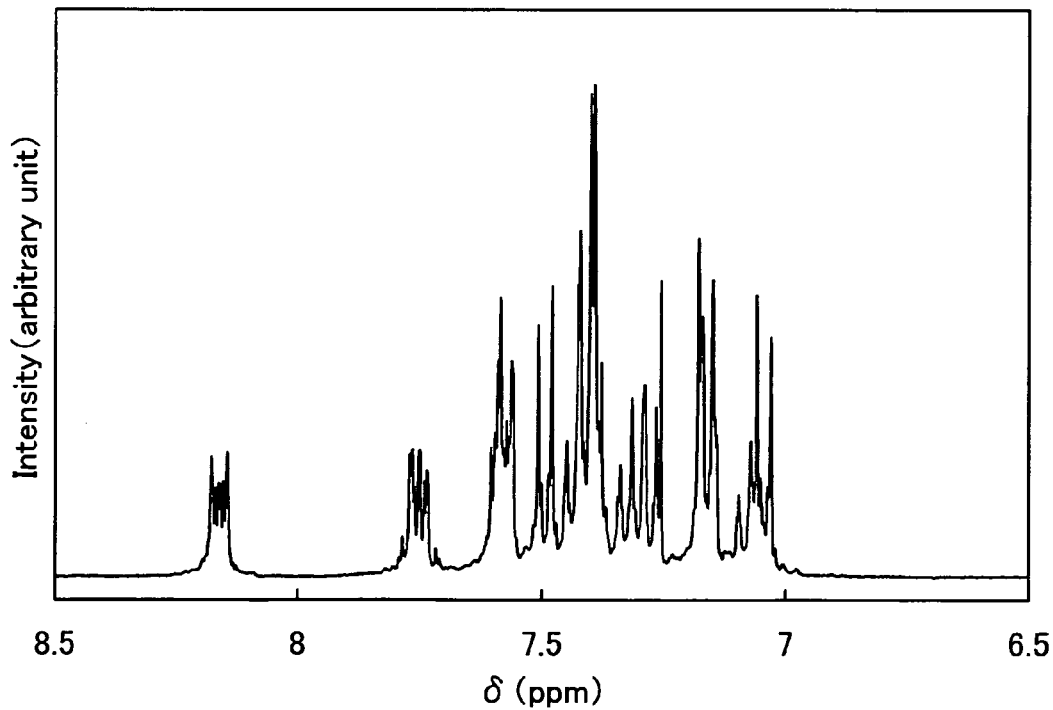

$^1$H NMR data of BPA1PQ is as follows: $^1$H NMR (CDCl$_3$, 300 MHz): δ=6.99-7.47 (m, 17H), 7.49 (d, J=8.8 Hz, 2H), 7.55-7.63 (m, 4H), 7.70-7.81 (m, 2H), 8.10-8.20 (m, 2H). FIGS. 11A and 11B each show a $^1$H NMR chart. The range of 6.5 ppm to 8.5 ppm in FIG. 11A is expanded to be shown in FIG. 11B.

Figure 12:
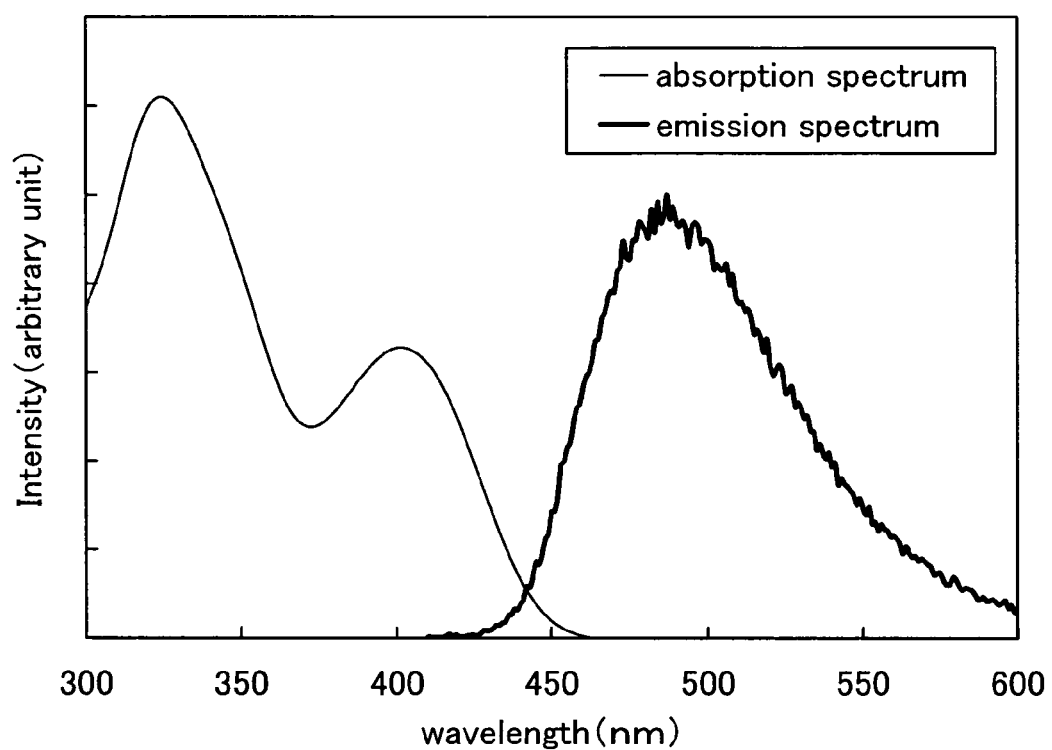
FIG. 12 is a graph showing an absorption spectrum and emission spectrum of a toluene solution of 2-{4-[N-(biphenyl-4-yl)-N-phenylamino]phenyl}-3-phenylquinoxaline (BPA1PQ) which is a quinoxaline derivative of the present invention.

FIG. 12 shows the absorption spectrum and emission spectrum of a toluene solution of BPA1PQ. An ultraviolet-visible spectrophotometer (V-550, manufactured by JASCO Corporation) is used for the measurement. The solution is put into a quartz cell, and the absorption spectrum thereof, from which the absorption spectrum of quartz is subtracted, is shown in FIG. 12. In FIG. 12, the horizontal axis indicates the wavelength (nm) and the vertical axis indicates the intensity (arbitrary unit). In the case of the toluene solution, the absorption is observed at around 324 nm and 402 nm, and the maximum emission wavelength is 487 nm (the excitation wavelength: 401 nm).

Figure 13:
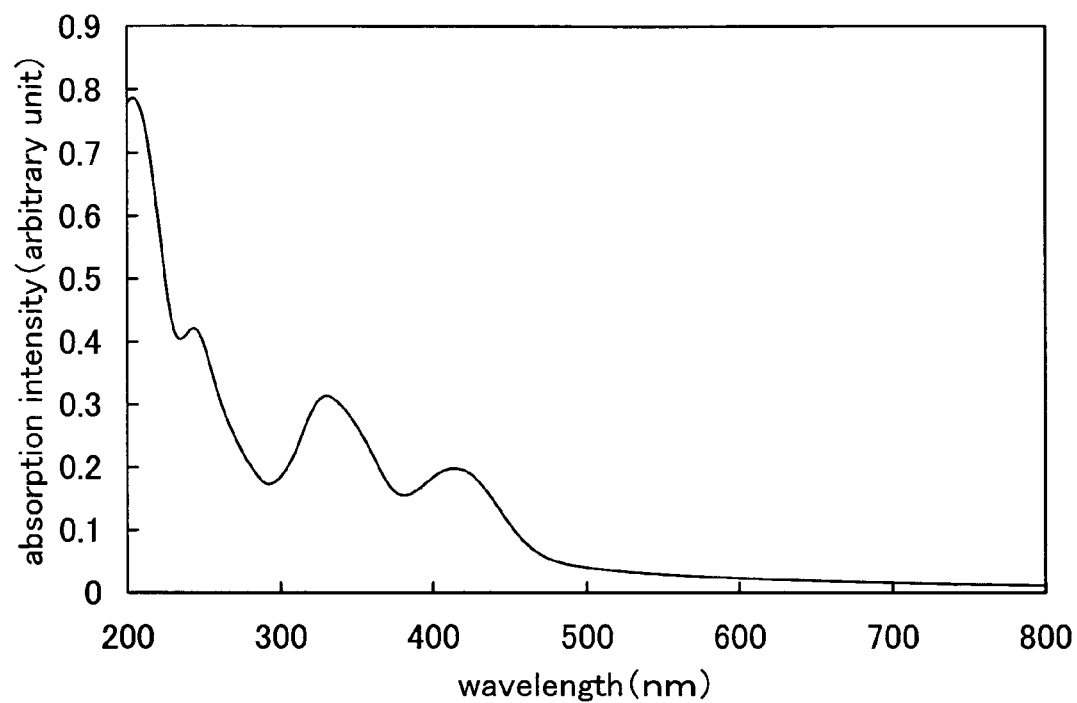
FIG. 13 is a graph showing an absorption spectrum of a thin film of 2-{4-[N-(biphenyl-4-yl)-N-phenylamino]phenyl}-3-phenylquinoxaline (BPA1PQ) which is a quinoxaline derivative of the present invention.
Figure 14:
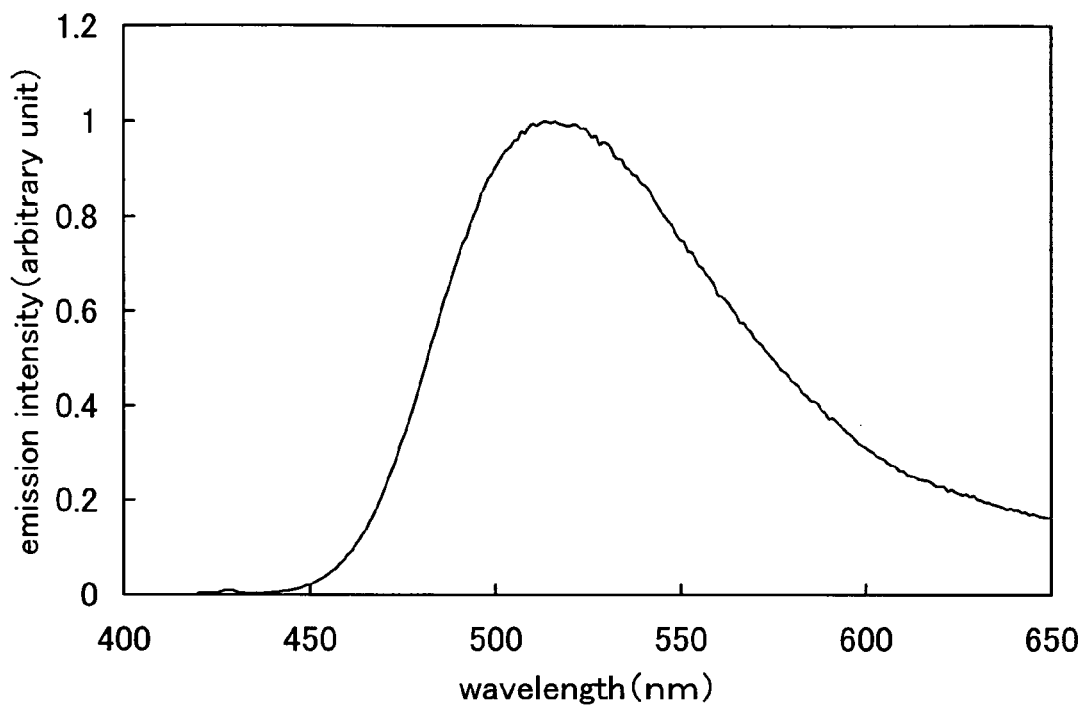
FIG. 14 is a graph showing an emission spectrum of a thin film of 2-{4-[N-biphenyl-4-yl)-N-phenylamino]phenyl}-3-phenylquinoxaline (BPA1PQ) which is a quinoxaline derivative of the present invention.

FIG. 13 shows the absorption spectrum of a thin film of BPA1PQ, and FIG. 14 shows the emission spectrum of the thin film of BPA1PQ. An ultraviolet-visible spectrophotometer (V-550, manufactured by JASCO Corporation) is used for the measurement. The thin film sample is prepared by vapor deposition on a quartz substrate, and the absorption spectrum thereof from which the absorption spectrum of quartz is subtracted, is shown in FIG. 13. In FIG. 13, the horizontal axis indicates the wavelength (nm) and the vertical axis indicates the absorption intensity (arbitrary unit). In FIG. 14, the horizontal axis indicates the wavelength (nm) and the vertical axis indicates the emission intensity (arbitrary unit). In the case of the thin film, the absorption is observed at around 330 nm and 414 nm, and the maximum emission wavelength is 513 nm (the excitation wavelength: 414 nm).

The ionization potential of BPA1PQ in the thin film state is measured using a photoelectron spectrometer (AC-2, manufactured by Riken Keiki Co., Ltd.) in the atmosphere and found to be 5.45 eV. Accordingly, the HOMO level of BPA1PQ in the thin film state is found to be −5.45 eV. The absorption edge is obtained from a Tauc plot assuming direct transition, using data of the absorption spectrum of BPA1PQ in the thin-film state, and the absorption edge is evaluated as the optical energy gap; as a result, the optical energy gap is 2.69 eV. The LUMO level obtained from the obtained energy gap and HOMO level is −2.76 eV.

The oxidation-reduction characteristics of BPA1PQ are measured by cyclic voltammetry (CV). An electrochemical analyzer (ALS model 600A, manufactured by BAS Inc.) is used for the measurement.

The solution for the CV measurement is prepared as follows: tetra-n-butylammonium perchlorate (n-Bu$_4$NClO$_4$) (produced by Tokyo Chemical Industry Co., Ltd., Catalog No. T0836) used as a supporting electrolyte is dissolved at a concentration of 100 mmol/L in dehydrated dimethylformamide (DMF) (produced by Sigma-Aldrich Corp., 99.8%, Catalog No. 22705-6) used as a solvent. BPA1PQ is further dissolved at a concentration of 1 mmol/L therein. A platinum electrode (PTE platinum electrode, produced by BAS Inc.), a platinum electrode (Pt counter electrode (5 cm) for VC-3, produced by BAS Inc.), and an Ag/Ag$^+$ electrode (RE5 non-aqueous solvent reference electrode, produced by BAS Inc.) are used as a working electrode, an auxiliary electrode, and a reference electrode, respectively. The CV measurement is carried out at room temperature.

The oxidation characteristics of BPA1PQ are examined by 100 cycles of measurement on the assumption that one cycle is a scan in which the potential of the working electrode with respect to the reference electrode is scanned from −0.73 V to 1.00 V and then scanned from 1.00 V to −0.73 V. The reduction characteristics of BPA1PQ are examined by 100 cycles of measurement on the assumption that one cycle is a scan in which the potential of the working electrode with respect to the reference electrode is scanned from −0.43 V to −2.20 V and then scanned from −2.20 V to −0.43 V The scan rate of the CV measurement is set to 0.1 V/s.

Figure 15:
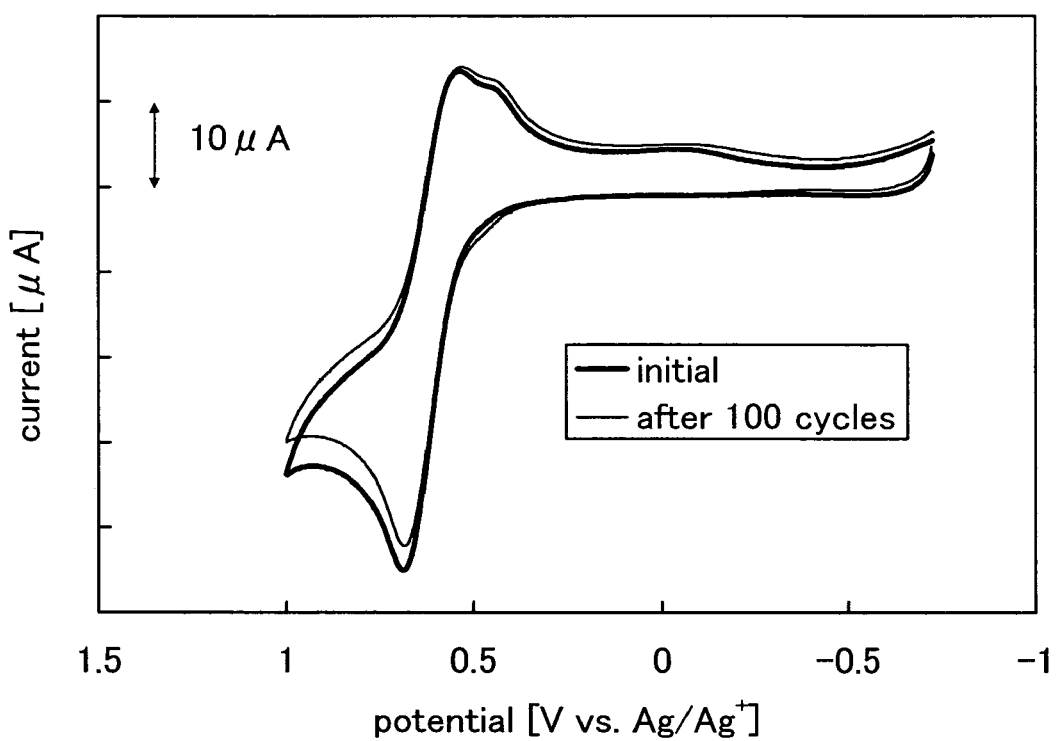
FIG. 15 is a graph showing a result of CV measurement of 2-{4-[N-(biphenyl-4-yl)-N-phenylamino]phenyl}-3-phenylquinoxaline (BPA1PQ) which is a quinoxaline derivative of the present invention.
Figure 16:
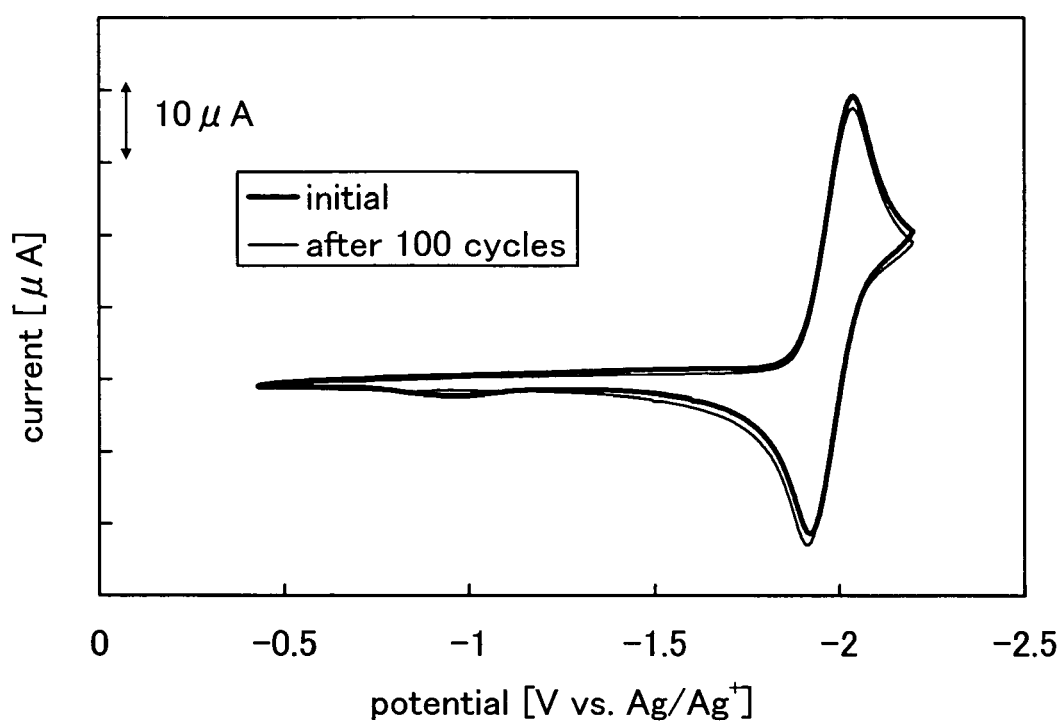
FIG. 16 is a graph showing a result of CV measurement of 2-{4-[N-(biphenyl-4-yl)-N-phenylamino]phenyl}-3-phenylquinoxaline (BPA1PQ) which is a quinoxaline derivative of the present invention.

FIG. 15 shows a result of the CV measurement of BPA1PQ on the oxidation side, and FIG. 16 shows a result of the CV measurement of BPA1PQ on the reduction side. In each of FIGS. 15 and 16, the horizontal axis indicates a potential (V) of the working electrode with respect to the reference electrode, and the vertical axis indicates a current value (μA) flowing between the working electrode and the auxiliary electrode. In FIG. 15, an oxidation current is observed at around 0.69 V (vs. the Ag/Ag$^+$ electrode). In FIG. 16, a reduction current is observed at around −2.04 V (vs. the Ag/Ag$^+$ electrode).

Although the scanning is repeated for 100 cycles, changes in the peak position and peak intensity of the CV curves are scarcely observed in each of the oxidation and the reduction. Accordingly, it is found that the quinoxaline derivatives of the present invention are significantly stable to repetitive oxidation-reduction.

Example 2

This example exemplifies a synthetic method of the quinoxaline derivative of the present invention represented by the following structural formula (105), 2-{4-[N,N-di(biphenyl-4-yl)amino]phenyl}-3-phenylquinoxaline (BBA1PQ).

(105)

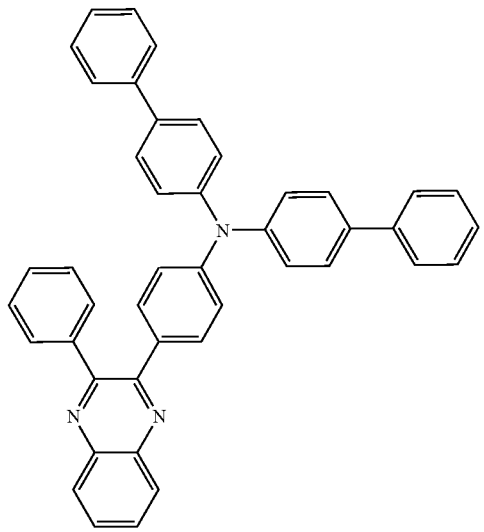

A synthetic method of BBA1PQ is described. A synthetic scheme of BBA1PQ is shown in (C-1).

(C-1)

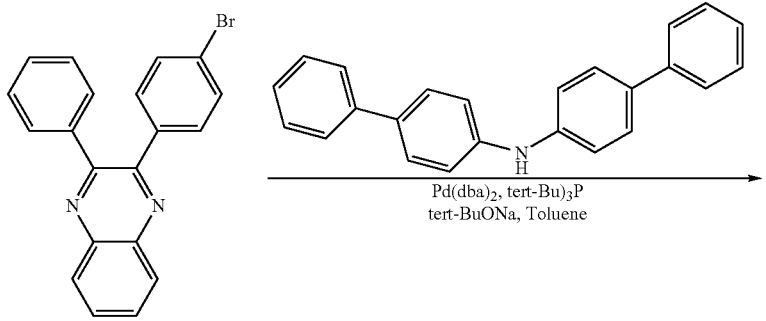

-continued

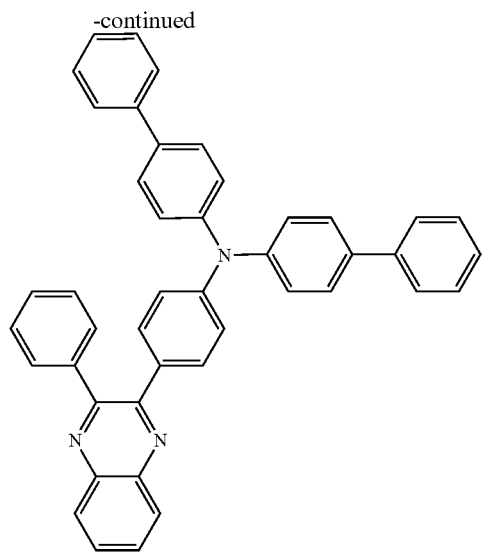

2-(4-bromophenyl)-3-phenylquinoxaline (2.0 g, 5.5 mmol), sodium tert-butoxide (2.0 g, 21 mmol), di(biphenyl-4-yl)amine (1.8 g, 5.5 mmol), and bis(dibenzylideneacetone)palladium(0) (0.10 g, 0.20 mmol) are put into a 50 mL three-neck flask, and the air in the flask is replaced with nitrogen. To the mixture are added toluene (20 mL) and a 10 wt % hexane solution of tri(tert-butyl)phosphine (0.1 mL), and this mixture is heated and stirred at 80° C. for 5 hours to be reacted. After the reaction, toluene is added to the reaction mixture, and this suspension is subjected to suction filtration through Florisil (produced by Wako Pure Chemical Industries, Ltd., Catalog No. 540-00135), celite (produced by Wako Pure Chemical Industries, Ltd., Catalog No. 531-16855) and alumina. The obtained filtrate is washed with a saturated sodium hydrogen carbonate solution and a saturated saline solution in this order. Magnesium sulfate is added to the organic layer that has been separated from the aqueous layer so that the organic layer is dried. This mixture is subjected to suction filtration in order to remove the magnesium sulfate. The obtained filtrate is concentrated, and then a solid is obtained. This solid is recrystallized with a mixed solvent of chloroform and hexane to give 2.9 g of a yellow powdered solid (87% yield). Nuclear magnetic resonance measurement (NMR) confirms that this compound is BBA1PQ.

The obtained yellow solid (2.0 g) is sublimed for purification by train sublimation, which is carried out under reduced pressure of 7.0 Pa, with a flow rate of argon at 3 mL/min, at 280° C. for 15 hours to give 1.9 g of the resultant solid (95% yield).

Figure 17A:
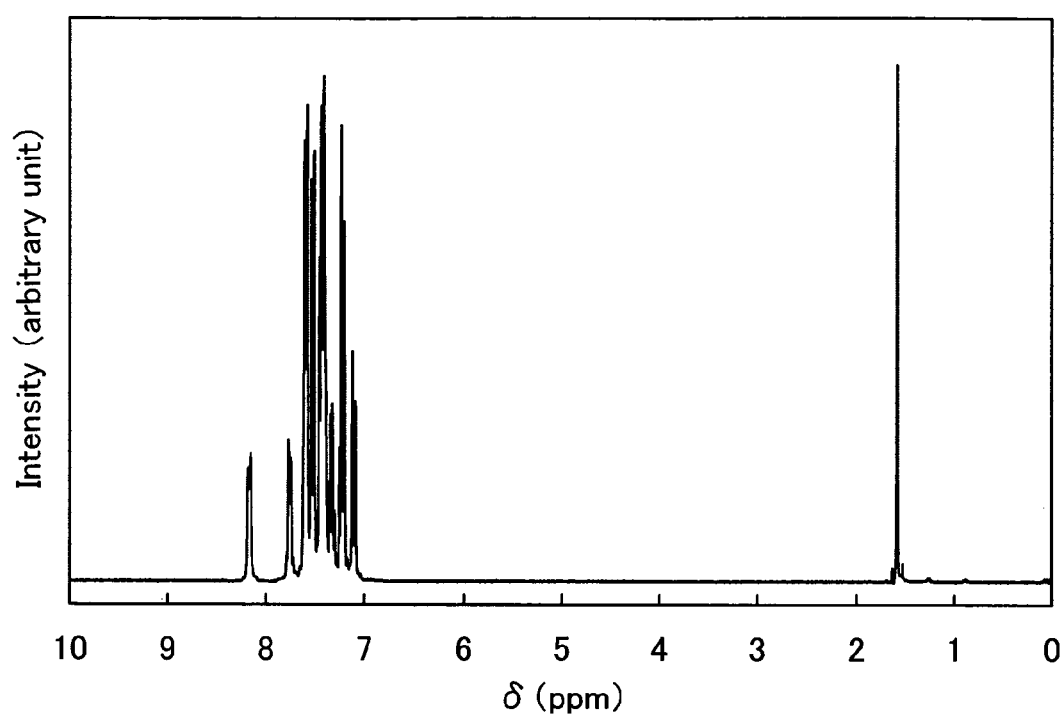
FIGS. 17A and 17B are $^1$H NMR charts of 2-{4-[N,N-di(biphenyl-4-yl)amino]phenyl}-3-phenylquinoxaline (BBA1PQ) which is a quinoxaline derivative of the present invention.
Figure 17B:
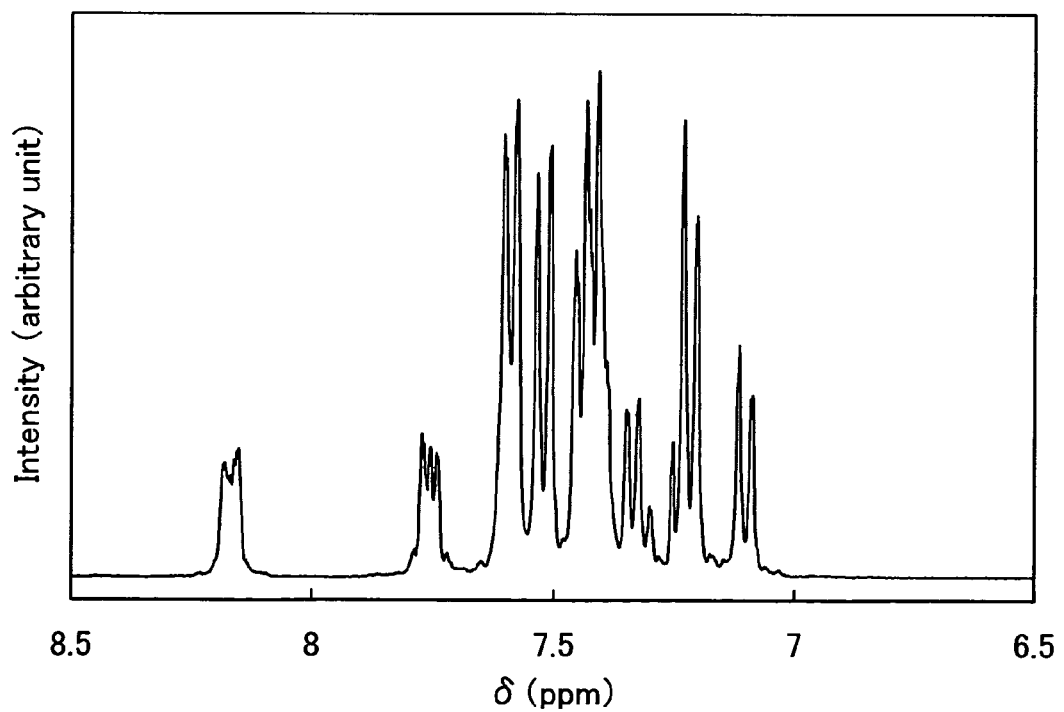

$^1$H NMR data of BBA1PQ is as follows: $^1$H NMR (CDCl$_3$, 300 MHz): δ=7.10 (d, J=8.3 Hz, 2H), 7.19-7.49 (m, 15H), 7.52 (d, J=8.3 Hz, 4H), 7.56-7.64 (m, 6H), 7.73-7.79 (m, 2H), 8.12-8.22 (m, 2H). FIGS. 17A and 17B each show a $^1$H NMR chart. The range of 6.5 ppm to 8.5 ppm in FIG. 17A is expanded to be shown in FIG. 17B.

Figure 18:
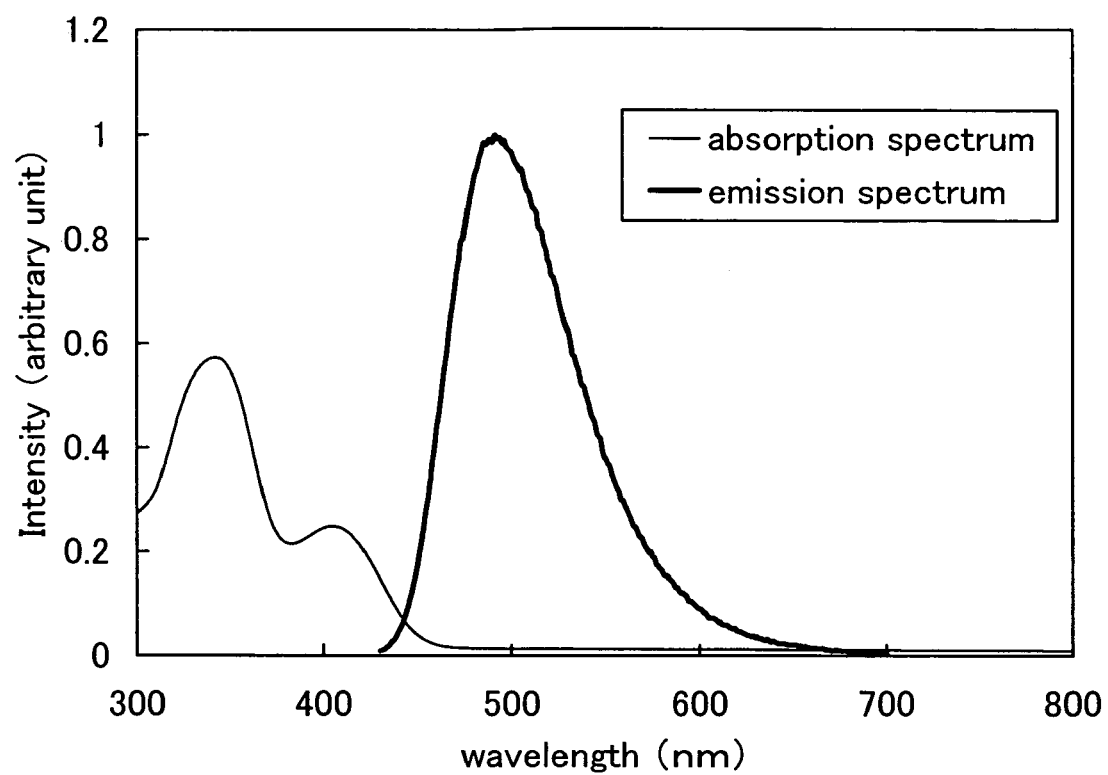
FIG. 18 is a graph showing an absorption spectrum and emission spectrum of a toluene solution of 2-{4-[N,N-di(biphenyl-4-yl)amino]phenyl}-3-phenylquinoxaline (BBA1PQ) which is a quinoxaline derivative of the present invention.

FIG. 18 shows the absorption spectrum and emission spectrum of a toluene solution of BBA1PQ. An ultraviolet-visible spectrophotometer (V-550, manufactured by JASCO Corporation) is used for the measurement. The solution is put into a quartz cell, and the absorption spectrum thereof, from which the absorption spectrum of quartz is subtracted, is shown in FIG. 18. In FIG. 18, the horizontal axis indicates the wavelength (nm) and the vertical axis indicates the intensity (arbitrary unit). In the case of the toluene solution, the absorption is observed at around 342 nm and 405 nm, and the maximum emission wavelength is 491 nm (the excitation wavelength: 406 nm).

Figure 19:
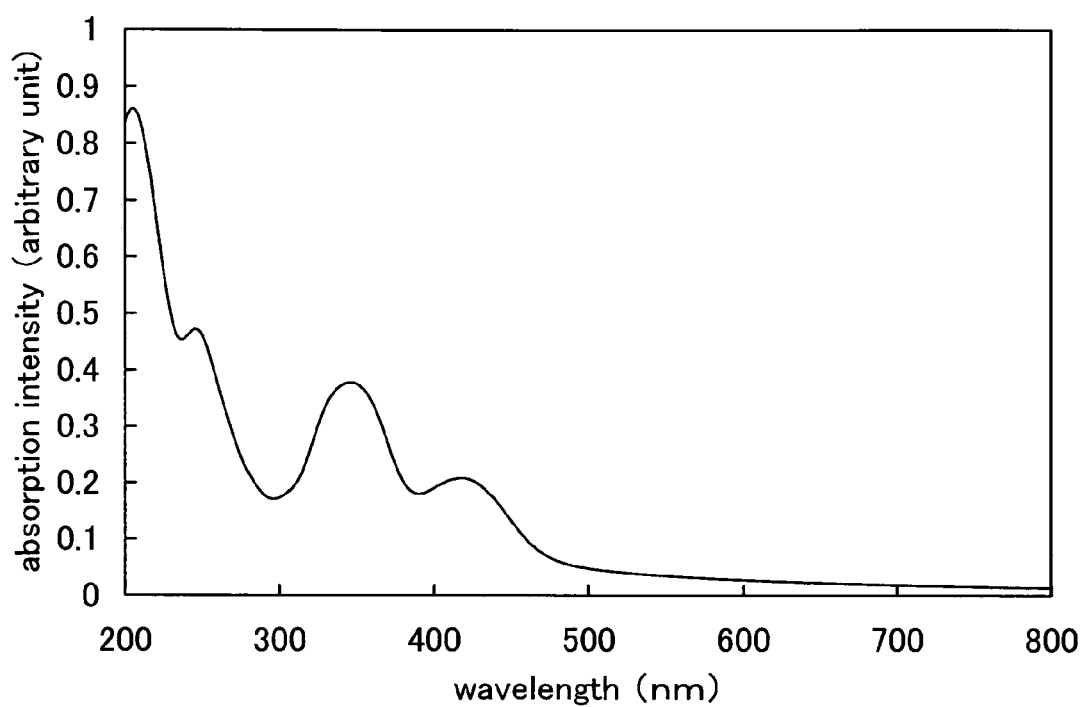
FIG. 19 is a graph showing an absorption spectrum of a thin film of 2-{4-[N,N-di(biphenyl-4-yl)amino]phenyl}-3-phenylquinoxaline (BBA1PQ) which is a quinoxaline derivative of the present invention.
Figure 20:
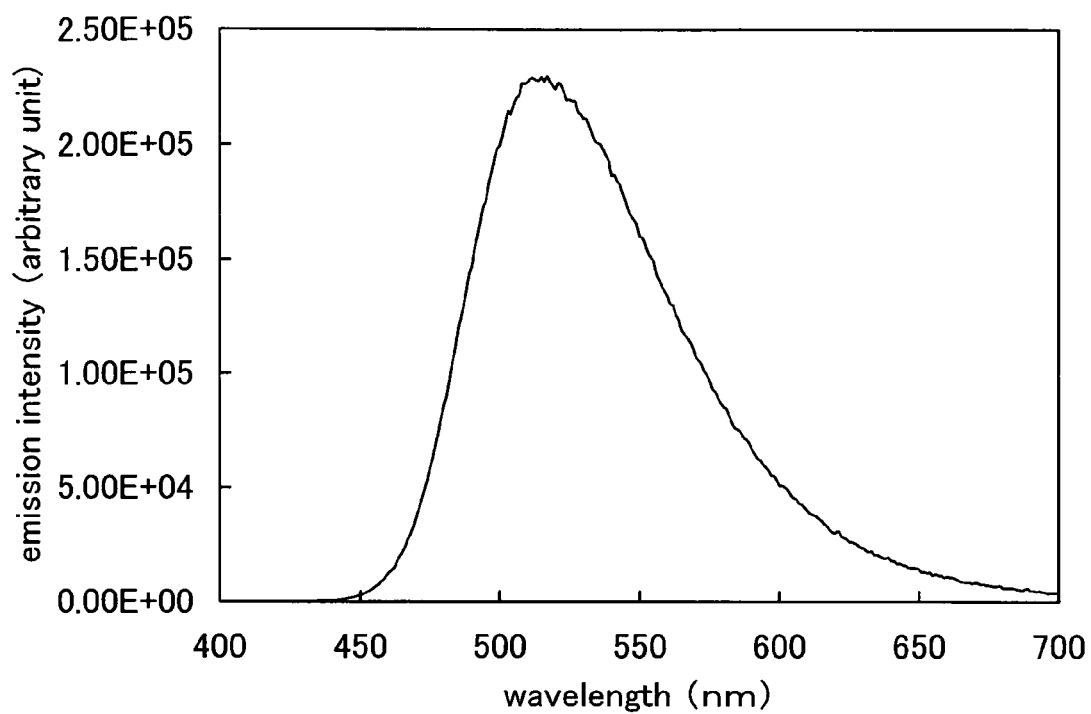
FIG. 20 is a graph showing an emission spectrum of a thin film of 2-{4-[N,N-di(biphenyl-4-yl)amino]phenyl}-3-phenylquinoxaline (BBA1PQ) which is a quinoxaline derivative of the present invention.

FIG. 19 shows the absorption spectrum of a thin film of BBA1PQ, and FIG. 20 shows the emission spectrum of the thin film of BBA1PQ. An ultraviolet-visible spectrophotometer (V-550, manufactured by JASCO Corporation) is used for the measurement. The thin film sample is prepared by vapor deposition on a quartz substrate, and the absorption spectrum thereof, from which the absorption spectrum of quartz is subtracted, is shown in FIG. 19. In FIG. 19, the horizontal axis indicates the wavelength (nm) and the vertical axis indicates the absorption intensity (arbitrary unit). In FIG. 20, the horizontal axis indicates the wavelength (nm) and the vertical axis indicates the emission intensity (arbitrary unit). In the case of the thin film, the absorption is observed at around 346 nm and 414 nm, and the maximum emission wavelength is 518 nm (the excitation wavelength: 418 nm).

The ionization potential of BBA1PQ in the thin film state is measured using a photoelectron spectrometer (AC-2, manufactured by Riken Keiki Co., Ltd.) in the atmosphere and found to be 5.43 eV. Accordingly, the HOMO level of BBA1PQ in the thin film state is found to be −5.43 eV. The absorption edge is obtained from a Tauc plot assuming direct transition, using data of the absorption spectrum of BBA1PQ in the thin-film state, and the absorption edge is evaluated as the optical energy gap; as a result, the optical energy gap is 2.66 eV. The LUMO level obtained from the obtained energy gap and HOMO level is −2.77 eV.

The oxidation-reduction characteristics of BBA1PQ are measured by cyclic voltammetry (CV). An electrochemical analyzer (ALS model 600A, manufactured by BAS Inc.) is used for the measurement.

The solution for the CV measurement is prepared as follows: tetra-n-butylammonium perchlorate (n-Bu$_4$NClO$_4$) (produced by Tokyo Chemical Industry Co., Ltd., Catalog No. T0836) used as a supporting electrolyte is dissolved at a concentration of 100 mmol/L in dehydrated dimethylformamide (DMF) (produced by Sigma-Adrich Corp., 99.8%, Catalog No. 22705-6) used as a solvent. BBA1PQ that is the measurement object is further dissolved at a concentration of 1 mmol/L therein. A platinum electrode (PTE platinum electrode, produced by BAS Inc.), a platinum electrode (Pt counter electrode (5 cm) for VC-3, produced by BAS Inc.), and an Ag/Ag+ electrode (RE5 non-aqueous solvent reference electrode, produced by BAS Inc.) are used as a working electrode, an auxiliary electrode, and a reference electrode, respectively. The CV measurement is carried out at room temperature.

The oxidation characteristics of BBA1PQ are examined by 100 cycles of measurement on the assumption that one cycle is a scan in which the potential of the working electrode with respect to the reference electrode is scanned from −0.57 V to 1.00 V and then scanned from 1.00 V to −0.57 V. The reduction characteristics of BBA1PQ axe examined by 100 cycles of measurement on the assumption that one cycle is a scan in which the potential of the working electrode with respect to the reference electrode is scanned from −0.40 V to −2.20 V and then scanned from −2.20 V to −0.40 V. The scan rate of the CV measurement is set to 0.1 V/s.

Figure 21:
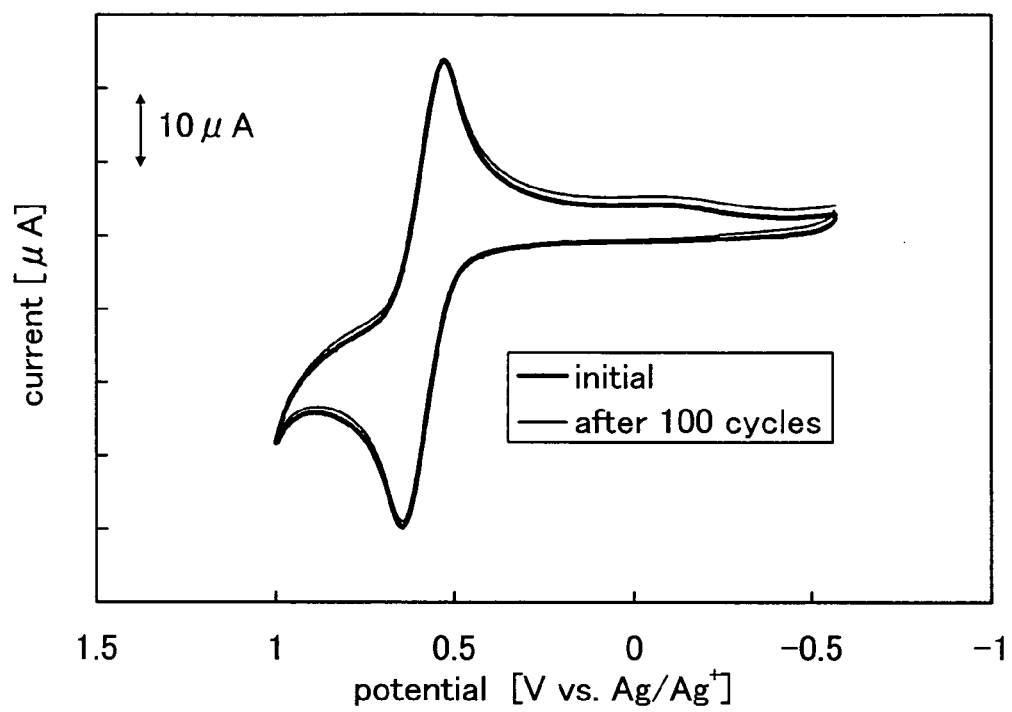
FIG. 21 is a graph showing a result of CV measurement of a thin film of 2-{4-[N,N-di(biphenyl-4-ylamino]phenyl}-3-phenylquinoxaline (BBA1PQ) which is a quinoxaline derivative of the present invention.
Figure 22:
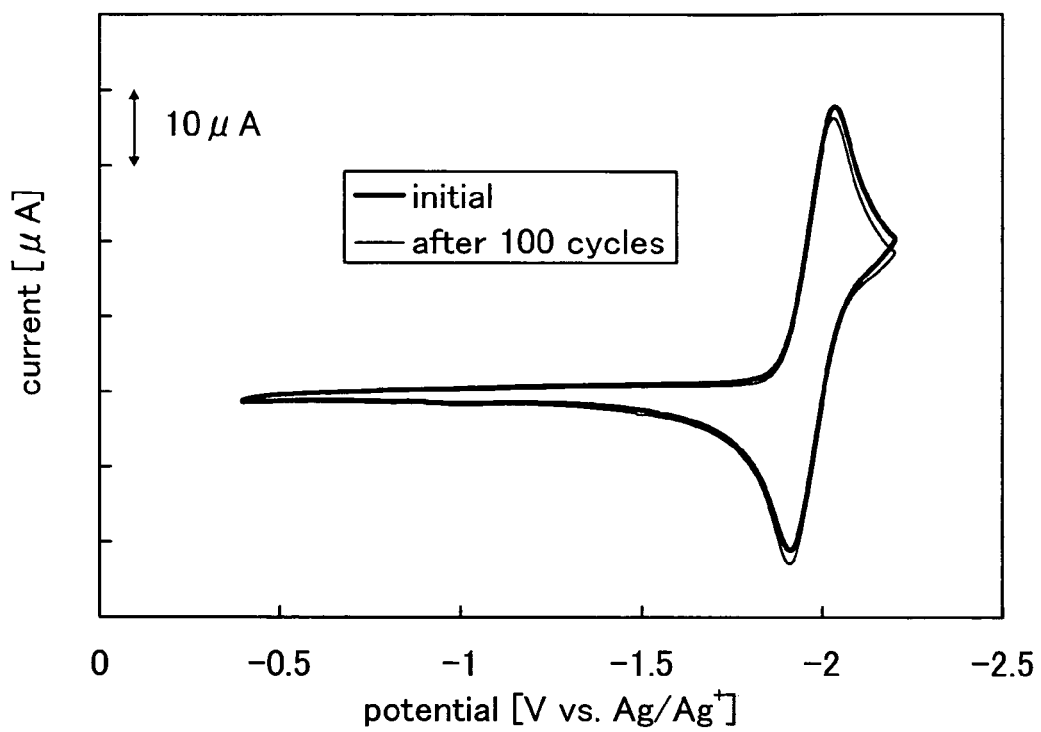
FIG. 22 is a graph showing a result of CV measurement of a thin film of 2-{4-[N,N-di(biphenyl-4-yl)amino]phenyl}-3-phenylquinoxaline (BBA1PQ) which is a quinoxaline derivative of the present invention.

FIG. 21 shows a result of the CV measurement of BBA1PQ on the oxidation side, and FIG. 22 shows a result of the CV measurement of BBA1PQ on the reduction side. In each of FIGS. 21 and 22, the horizontal axis indicates a potential (V) of the working electrode with respect to the reference electrode, and the vertical axis indicates a current value (μA) flowing between the working electrode and the auxiliary electrode. In FIG. 21, an oxidation current is observed at around 0.65 V (vs. the Ag/Ag+ electrode). In FIG. 22, a reduction current is observed at around −2.04 V (vs. the Ag/Ag+ electrode).

Although the scanning is repeated for 100 cycles, changes in the peak position and peak intensity of a CV curve are scarcely observed in each of the oxidation and the reduction. Accordingly, it is found that the quinoxaline derivatives of the present invention are significantly stable to repetitive oxidation-reduction.

Example 3

Figure 23:
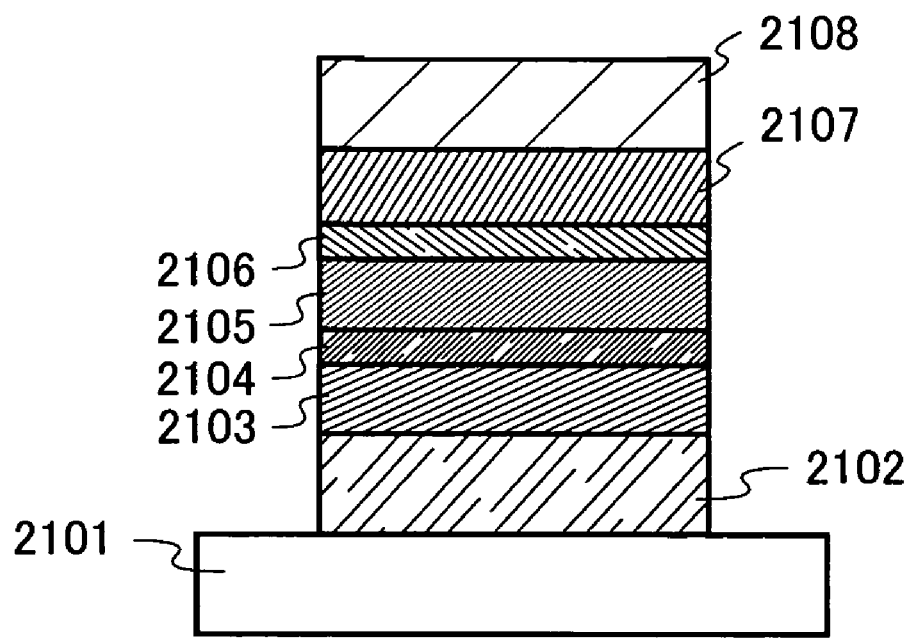
FIG. 23 is a view illustrating a light-emitting element of Examples.

In this example, the light-emitting element of the present invention is described with reference to FIG. 23. Chemical formulae of the materials used in Examples 3 and 4 are shown below. The material of which the structural formula has already been shown is omitted.

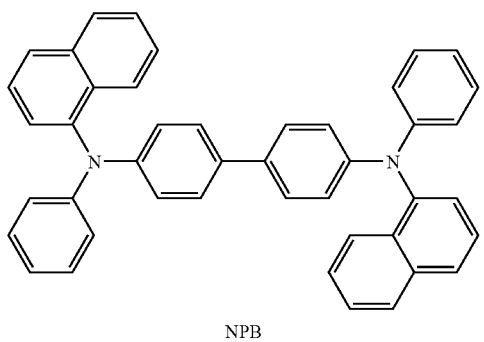

NPB

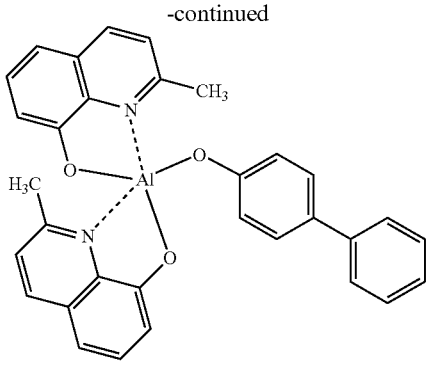

BAlq

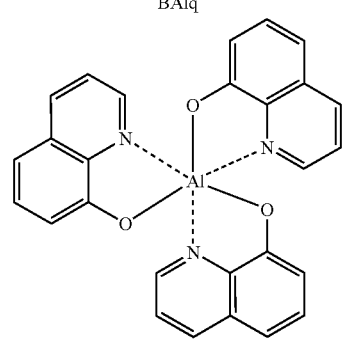

Alq

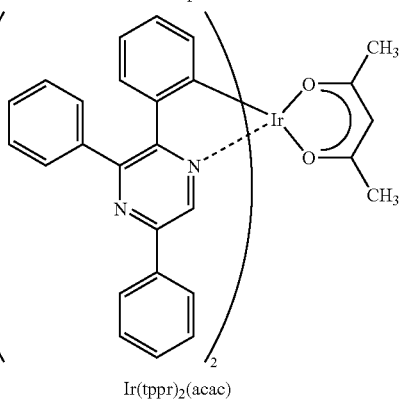

Ir(tppr)$_2$(acac)

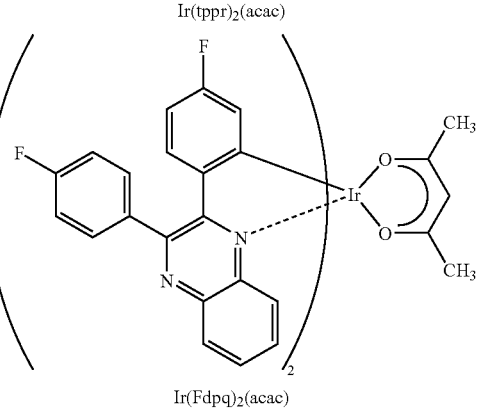

Ir(Fdpq)$_2$(acac)

Hereinafter, a method of fabricating a light-emitting element of this example is described.
(Light-Emitting Element 1)

First, indium tin oxide containing silicon oxide is deposited on a glass substrate 2101 by a sputtering method to form a first electrode 2102. The thickness of the first electrode 2102 is 110 nm and the electrode area is 2 mm×2 mm.

Next, the substrate with the first electrode is fixed to a substrate holder in a vacuum evaporation apparatus so that the side of the substrate, on which the first electrode is formed, faces downward. Then, after the pressure of the evaporation apparatus is reduced to approximately $10^{-4}$ Pa, 4,4'-bis[N-(1-napthyl)-N-phenylamino]biphenyl (NPB) and molybdenum (VI) oxide are co-deposited on the first electrode 2102 to form a layer 2103 containing a composite material. The thickness of the layer 2103 is adjusted to be 50 nm. The weight ratio of NPB to molybdenum(VI) oxide is adjusted to be 4:1 (=NPB: molybdenum oxide).

Next, NPB is deposited on the layer 2103 containing the composite material by an evaporation method using resistance heating to form a hole-transporting layer 2104 having a thickness of 10 nm.

Furthermore, 2-{4-[N-(biphenyl-4-yl)-N-phenylamino]phenyl}-3-phenylquinoxaline (BPA1PQ), which is the quinoxaline derivative of the present invention, represented by the structural formula (102), and (acetylacetonato)bis[2,3-bis(4-fluorophenyl)quinoxalinato]iridium(III) (Ir(Fdpq)$_2$(acac)) are co-deposited on the hole-transporting layer 2104 to form a light-emitting layer 2105 having a thickness of 30 nm. The weight ratio of BPA1PQ to Ir(Fdpq)$_2$(acac) is adjusted to be 1:0.06 (=BPA1PQ:Ir(Fdpq)$_2$(acac)).

Then, bis(2-methyl-8-quinolinolato)(4-phenylphenolato)aluminum (BAlq) is deposited on the light-emitting layer 2105 by an evaporation method using resistance heating to form an electron-transporting layer 2106 having a thickness of 10 nm.

Moreover, tris(8-quinolinolato)aluminum (Alq) and lithium are co-deposited on the electron-transporting layer 2106 to form an electron-injecting layer 2107 having a thickness of 50 nm. The weight ratio of Alq to lithium is adjusted to be 1:0.01 (=Alq:lithium).

Finally, aluminum is deposited on the electron-injecting layer 2107 by an evaporation method using resistance heating to form a second electrode 2108 having a thickness of 200 nm. Accordingly, a light-emitting element 1 is fabricated.

Figure 24:
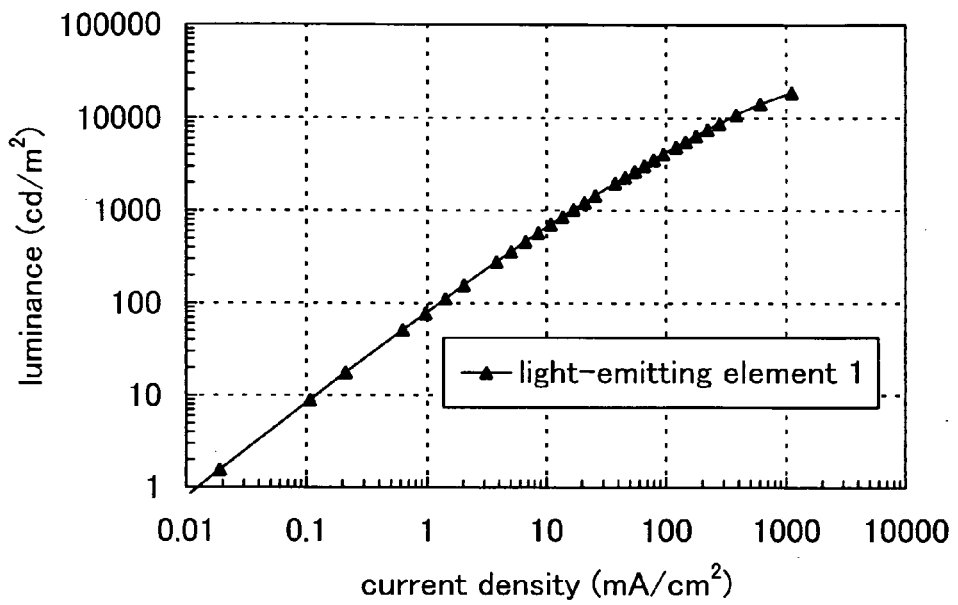
FIG. 24 is a graph showing current density-luminance characteristics of a light-emitting element fabricated in Example 3.
Figure 25:
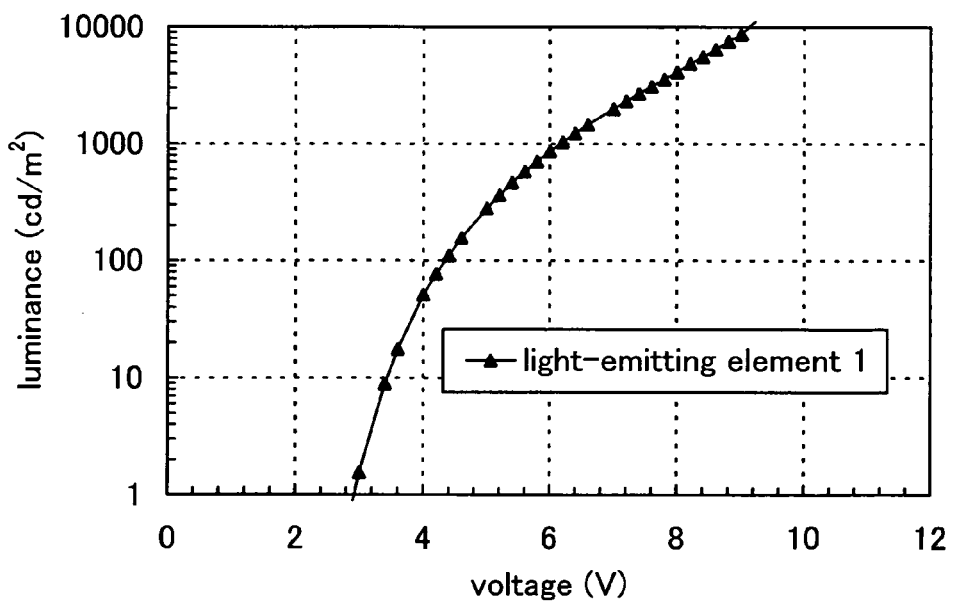
FIG. 25 is a graph showing voltage-luminance characteristics of a light-emitting element fabricated in Example 3.
Figure 26:
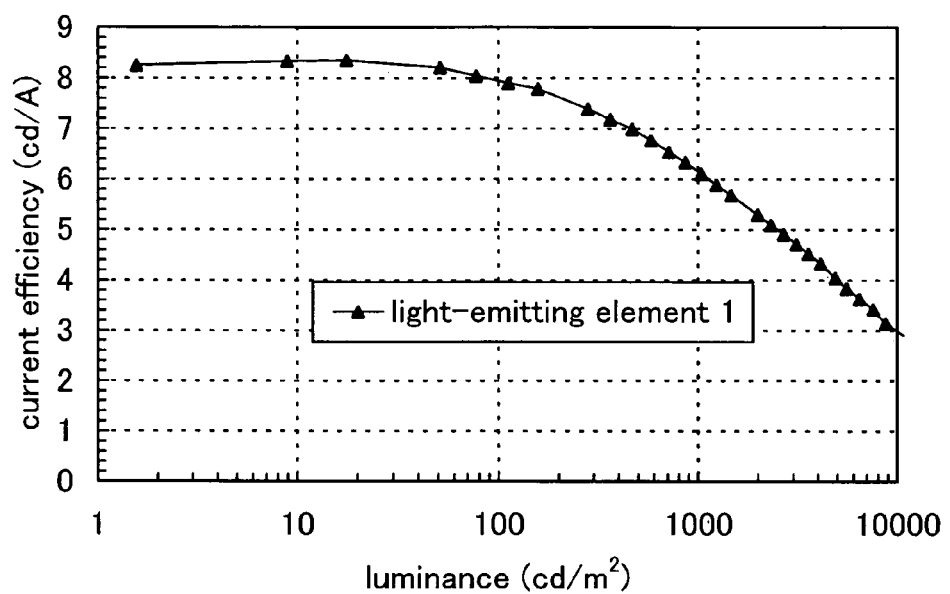
FIG. 26 is a graph showing luminance-current efficiency characteristics of a light-emitting element fabricated in Example 3.
Figure 27:
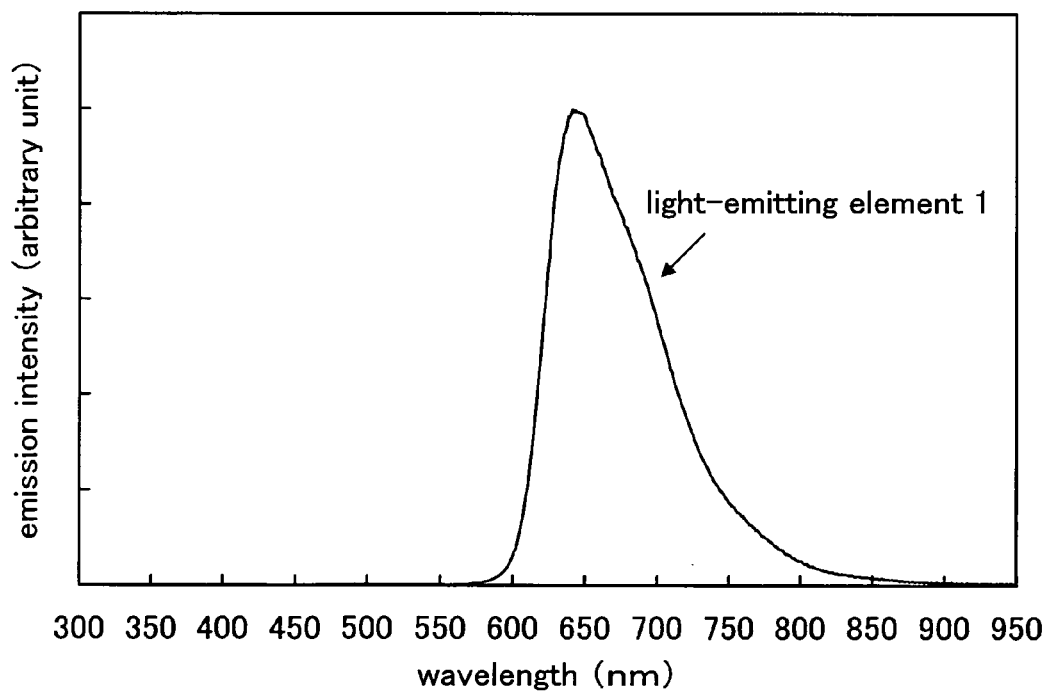
FIG. 27 is a graph showing an emission spectrum of a light-emitting element fabricated in Example 3.

FIG. 24 shows current density-luminance characteristics of the light-emitting element 1. FIG. 25 shows voltage-luminance characteristics. FIG. 26 shows luminance-current efficiency characteristics. FIG. 27 shows an emission spectrum when a current of 1 mA flows.

When the luminance of the light-emitting element 1 is 1000 cd/m$^2$, the CIE color coordinates are x=0.71 and y=0.29 and the emission color is red; the current efficiency is 6.1 cd/A and the external quantum efficiency is 14%, which shows that the light-emitting element 1 has a high efficiency; and the voltage is 6.2 V, the current density is 16.9 mA/cm$^2$, and the power efficiency is 3.1 lm/W, which shows that the light-emitting element 1 has a high power efficiency.

Therefore, by using any of the quinoxaline derivatives of the present invention, a light-emitting element with high emission efficiency and low power consumption can be obtained.

Example 4

In this example, the light-emitting element of the present invention is described with reference to FIG. 23. A method of fabricating the light-emitting element of this example is described below.

(Light-Emitting Element 2)

First, indium tin oxide containing silicon oxide is deposited on a glass substrate 2101 by a sputtering method to form a first electrode 2102. The thickness of the first electrode 2102 is 110 nm and the electrode area is 2 mm×2 mm.

Next, the substrate with the first electrode is fixed to a substrate holder in a vacuum evaporation apparatus so that the side of the substrate, on which the first electrode is formed, faces downward. Then, after the pressure of the evaporation apparatus is reduced to approximately $10^{-4}$ Pa, 4,4'-bis[N-(1-napthyl)-N-phenylamino]biphenyl (NPB) and molybdenum (VI) oxide are co-deposited on the first electrode 2102 to form a layer 2103 containing a composite material. The thickness of the layer 2103 is adjusted to be 50 nm. The weight ratio of NPB to molybdenum(VI) oxide is adjusted to be 4:1 (=NPB: molybdenum oxide).

Next, NPB is deposited on the layer 2103 containing the composite material by an evaporation method using resistance heating to form a hole-transporting layer 2104 having a thickness of 10 nm.

Furthermore, 2-{4-[N-(biphenyl-4-yl)-N-phenylamino]phenyl}-3-phenylquinoxaline (BPA1PQ), which is the quinoxaline derivative of the present invention, represented by the structural formula (102), and (acetylacetonato)bis(2,3,5-triphenylpyrazinato)iridium(III) (Ir(tppr)$_2$(acac)) are co-deposited on the hole-transporting layer 2104 to form a light-emitting layer 2105 having a thickness of 30 nm. The weight ratio of BPA1PQ to Ir(tppr)$_2$(acac) is adjusted to be 1:0.06 (=BPA1PQ:Ir(tppr)$_2$(acac)).

Then, bis(2-methyl-8-quinolinolato)(4-phenylphenolato)aluminum (BAlq) is deposited on the light-emitting layer 2105 by an evaporation method using resistance heating to form an electron-transporting layer 2106 having a thickness of 10 nm.

Moreover, tris(8-quinolinolato)aluminum (Alq) and lithium are co-deposited on the electron-transporting layer 2106 to form an electron-injecting layer 2107 having a thickness of 50 nm. The weight ratio of Alq to lithium is adjusted to be 1:0.01 (=Alq:lithium).

Finally, aluminum is deposited on the electron-injecting layer 2107 by an evaporation method using resistance heating to form a second electrode 2108 having a thickness of 200 μm. Accordingly, a light-emitting element 2 is fabricated.

(Light-Emitting Element 3)

Furthermore, a light-emitting layer 2105 is formed by co-deposition of 2-{4-[N,N-di(biphenyl-4-yl)amino]phenyl}-3-phenylquinoxaline (BBA1PQ), which is the quinoxaline derivative of the present invention, represented by the structural formula (105), with (acetylacetonato)bis(2,3,5-triphenylpyrazinato)iridium(III) (Ir(tppr)$_2$(acac)). A weight ratio of BBA1PQ to Ir(tppr)$_2$(acac) is adjusted to be 1:0.06 (=BBA1PQ:Ir(tppr)$_2$(acac)). A light-emitting element 3 is fabricated similarly to the light-emitting element 2 except the light-emitting layer 2105.

Figure 28:
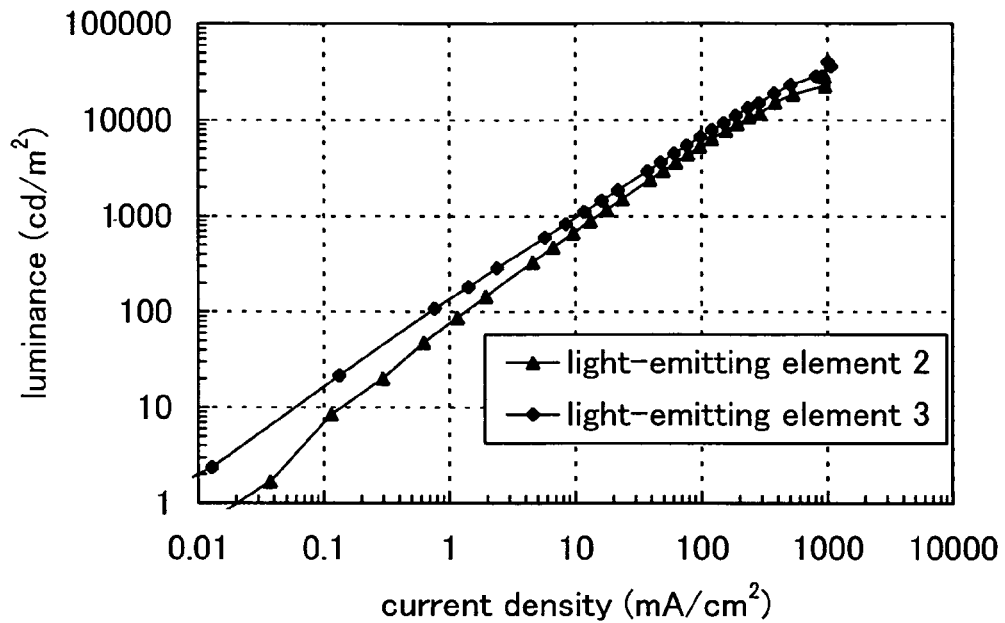
FIG. 28 is a graph showing current density-luminance characteristics of light-emitting elements fabricated in Example 4.
Figure 29:
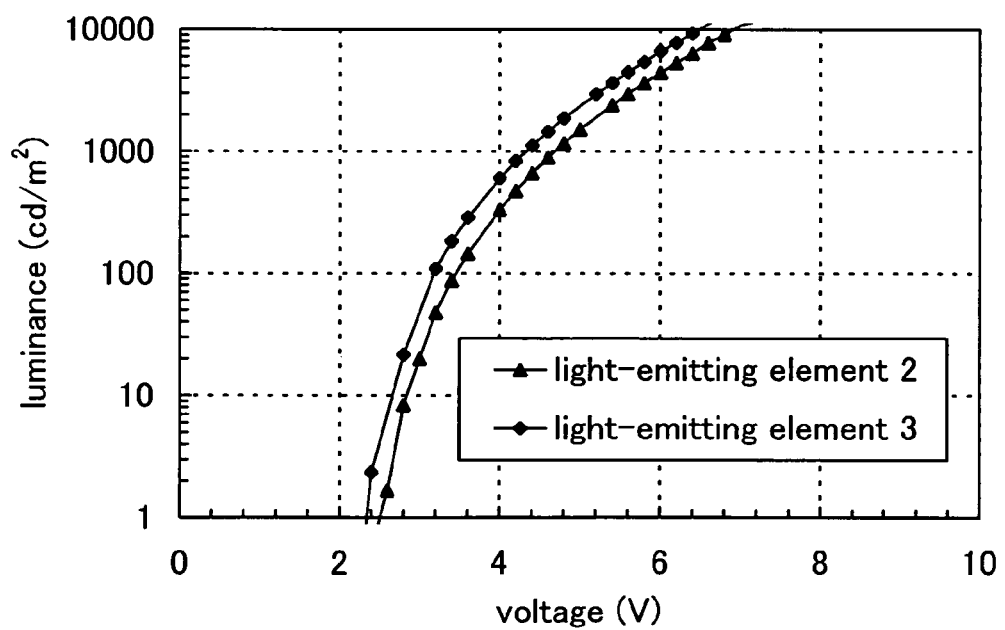
FIG. 29 is a graph showing voltage-luminance characteristics of light-emitting elements fabricated in Example 4.
Figure 30:
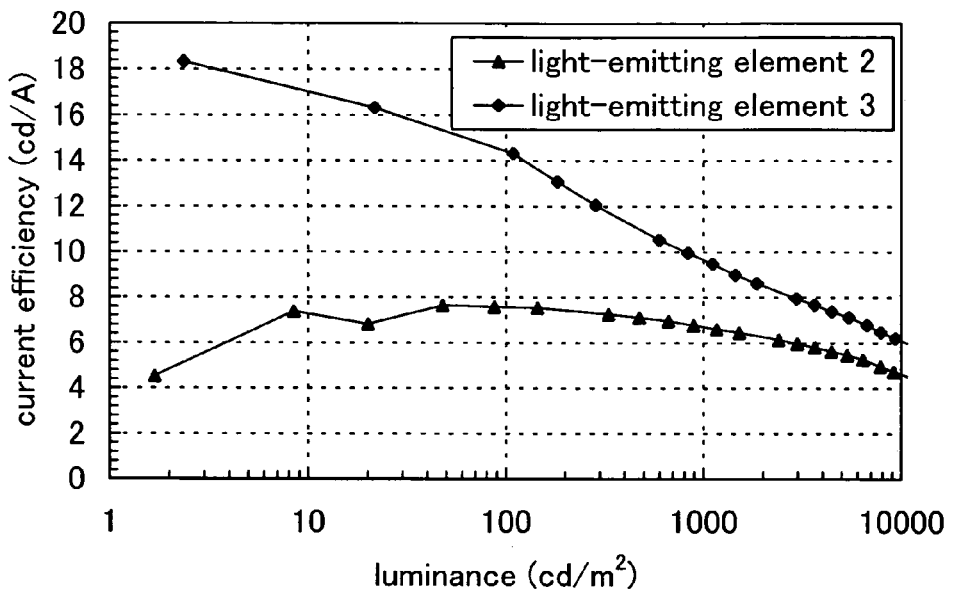
FIG. 30 is a graph showing luminance-current efficiency characteristics of light-emitting elements fabricated in Example 4.
Figure 31:
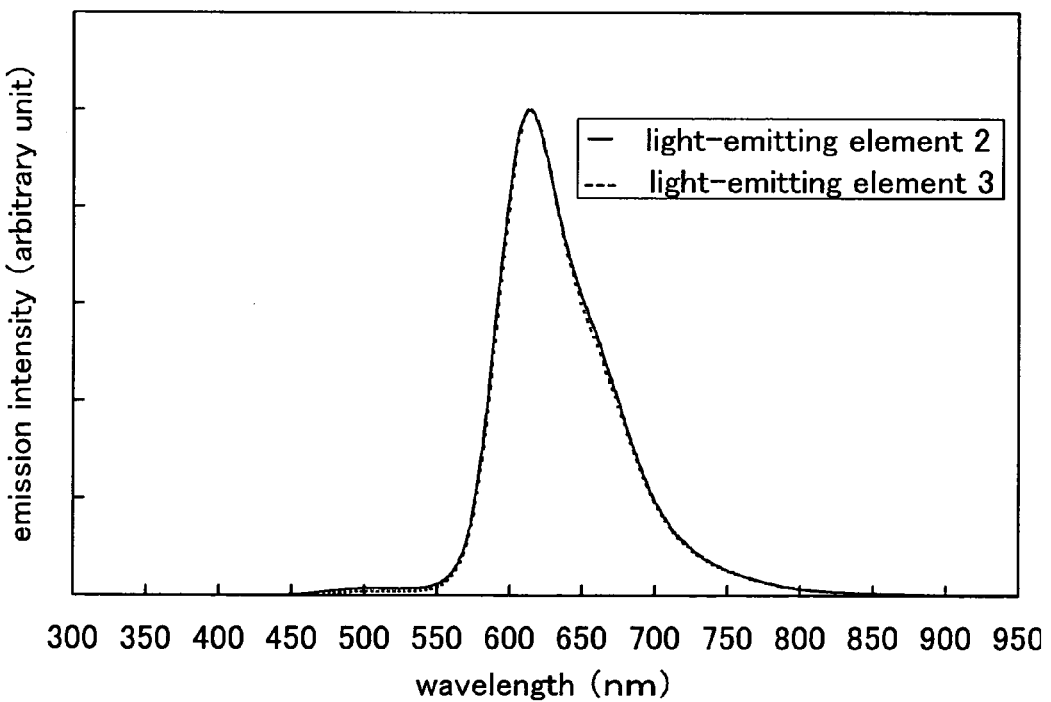
FIG. 31 is a graph showing emission spectra of light-emitting elements fabricated in Example 4.

FIG. 28 shows current density-luminance characteristics of the light-emitting elements 2 and 3. FIG. 29 shows voltage-luminance characteristics. FIG. 30 shows luminance-current efficiency characteristics. FIG. 31 shows emission spectra when a current of 1 mA flows.

When the luminance of the light-emitting element 2 is 890 cd/m$^2$, the CIE color coordinates are x=0.64 and y=0.36 and the emission color is red; the current efficiency is 6.8 cd/A and the external quantum efficiency is 4.6%, which shows that the light-emitting element 2 has a high efficiency; and the voltage is 4.6 V, the current density is 13.2 mA/cm$^2$, and the power efficiency is 4.6 lm/W, which shows that the light-emitting element 2 requires a low driving voltage and has a high power efficiency.

When the luminance of the light-emitting element 3 is 1100 cd/m², the CIE color coordinates are x=0.64 and y=0.35 and the emission color is red; the current efficiency is 9.5 cd/A and the external quantum efficiency is 6.8%, which shows that the light-emitting element 3 has a high efficiency; and the voltage is 4.4 V, the current density is 11.8 mA/cm², and the power efficiency is 6.8 lm/W, which shows that the light-emitting element 3 requires a low driving voltage and has a high power efficiency.

Accordingly, a light-emitting element with high emission efficiency and low power consumption can be obtained by using any of the quinoxaline derivatives of the present invention.

Example 5

This example describes the materials used in other examples.

<<Synthesis of Ir(tppr)₂(acac)>>

Hereinafter, an example of the synthesis of (acetylacetonato)bis(2,3,5-triphenylpyrazinato)iridium(III) (Ir(tppr)₂(acac)) represented by a structural formula (402) will be specifically exemplified.

(402)

[Step 1]

Synthesis of 2,3,5-triphenylpyrazine (Htppr) is described.

First, a solution is prepared by mixing 5.5 mL of a dibutyl ether solution of phenyl lithium (produced by Wako Pure Chemical Industries, Ltd., 2.1 mol/L) and 50 mL of diethyl ether under a nitrogen atmosphere. Then, 2.43 g of 2,3-diphenylpyrazine is dropped into this solution while the solution is being cooled with ice, and the mixture is stirred at room temperature for 24 hours. After the stirring, water is added to the mixture, and the organic layer is extracted with diethyl ether. The extracted organic layer is washed with water and dried with magnesium sulfate. After the drying, to the organic layer is added an excess amount of activated manganese dioxide, and the mixture is stirred sufficiently and then filtered. After the solvent of the filtrate is evaporated, the obtained residue is recrystallized with ethanol to give a pyrazine derivative, Htppr (a yellow powder, 56% yield). A synthetic scheme of Step 1 is shown in the following (G-1).

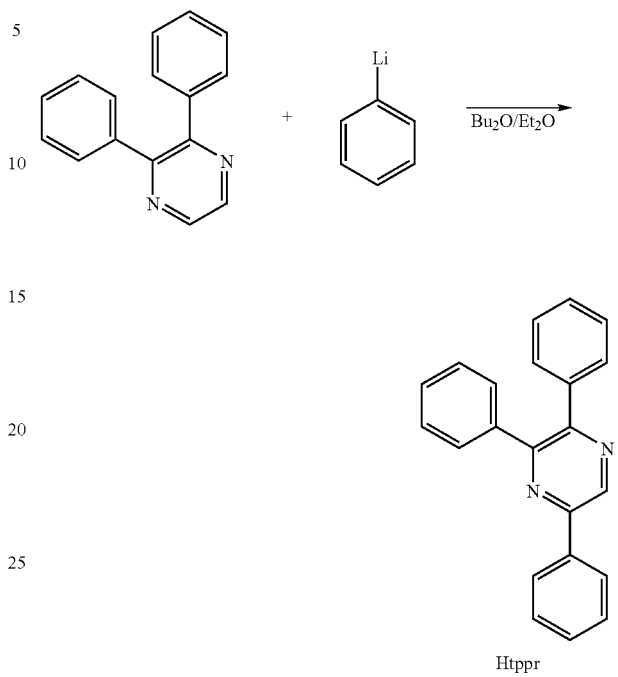

[Step 2]

Synthesis of di-μ-chloro-bis[bis(2,3,5-triphenylpyrazinato)iridium(III)] (abbr.:[Ir(tppr)₂Cl]₂) is described.

Next, 1.08 g of Htppr, which is the pyrazine derivative obtained in above Step 1, and 0.73 g of iridium chloride hydrate (IrCl₃.H₂O) (produced by Sigma-Aldrich Corp.) are mixed in a mixed solvent of 2-ethoxyethanol (30 mL) and water (10 mL). The mixture is refluxed under a nitrogen atmosphere for 16 hours. The precipitated powder is filtered. The residue is washed with ethanol, ether, and then hexane to give a dinuclear complex [Ir(tppr)₂Cl]₂ (an orange powder, 97% yield). A synthetic scheme of Step 2 is shown in the following (G-2).

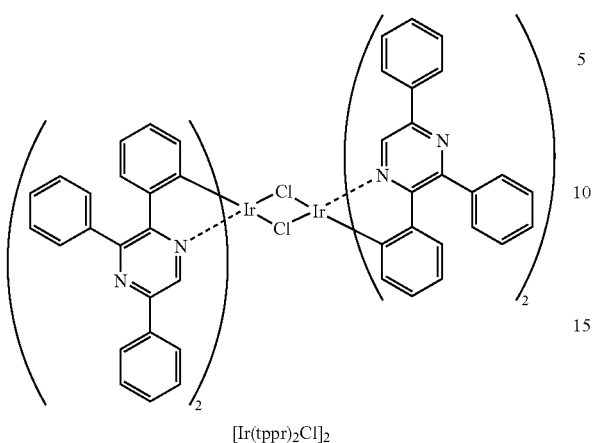

[Ir(tppr)$_2$Cl]$_2$

[Step 3]

Synthesis of (acetylacetonato)bis(2,3,5-triphenylpyrazinato)iridium(III) (Ir(tppr)$_2$(acac)) is described.

Then, 2.00 g of [Ir(tppr)$_2$Cl]$_2$, which is the dinuclear complex obtained in above Step 2, 0.37 mL of acetylacetone, and 1.26 g of sodium carbonate are mixed in a solvent of 2-ethoxyethanol (40 mL). The mixture is refluxed under a nitrogen atmosphere for 18 hours. After the reflux, the mixture is filtered and the filtrate is left for one week. Then, the precipitated crystal is removed by filtration and the solvent of the filtrate is evaporated. The obtained residue is recrystallized with a mixed solvent of dichloromethane and ethanol. The powder obtained by the recrystallization is washed with ethanol and then ether to give an organometallic complex Ir(tppr)$_2$(acac) (a red powder, 16% yield). A synthetic scheme of Step 3 is shown in the following (G-3).

(G-3)

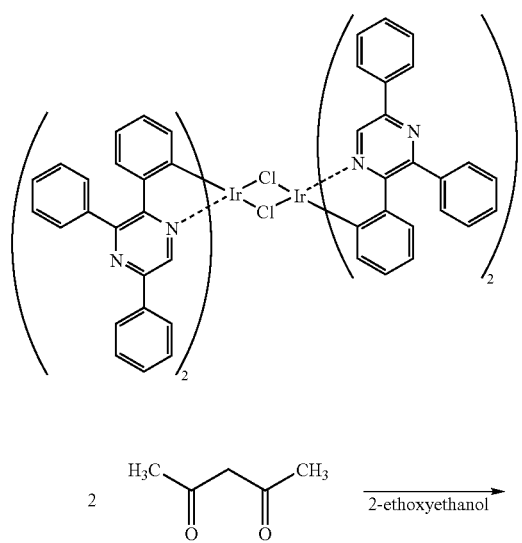

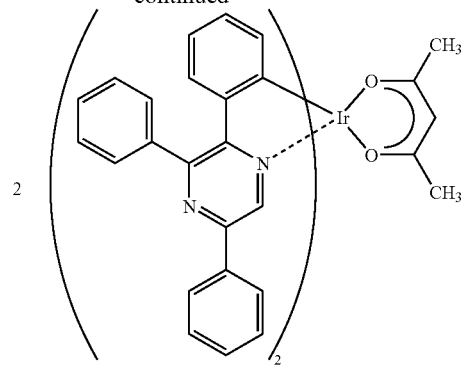

Figure 32A:
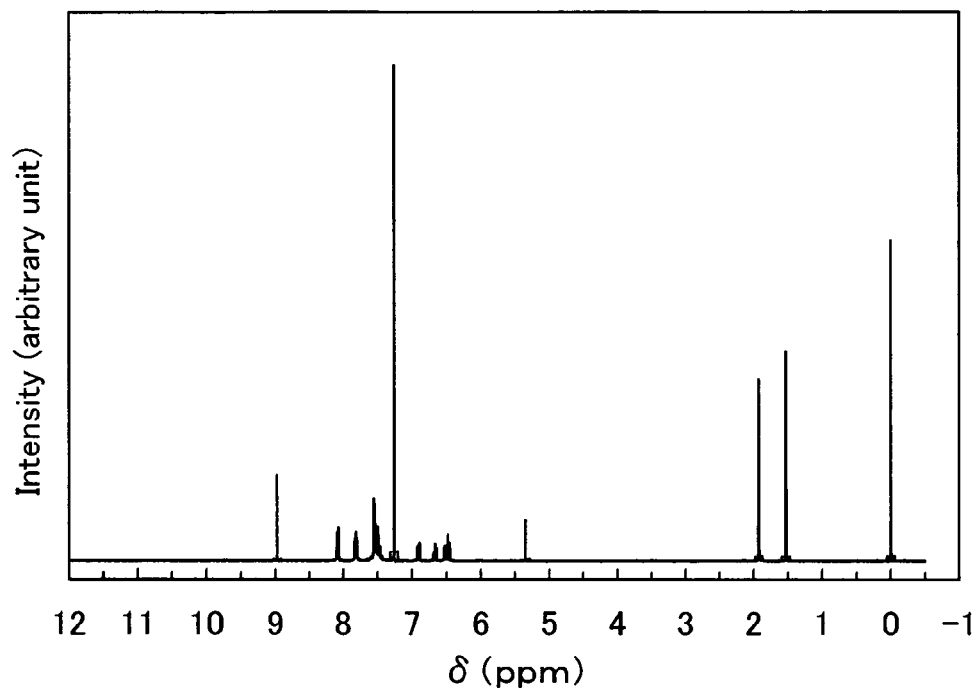
FIGS. 32A and 32B are $^1$H NMR charts of (acetylacetonato)bis(2,3,5-triphenylpyrazinato)iridium (III) (Ir(tppr)$_2$(acac))
Figure 32B:
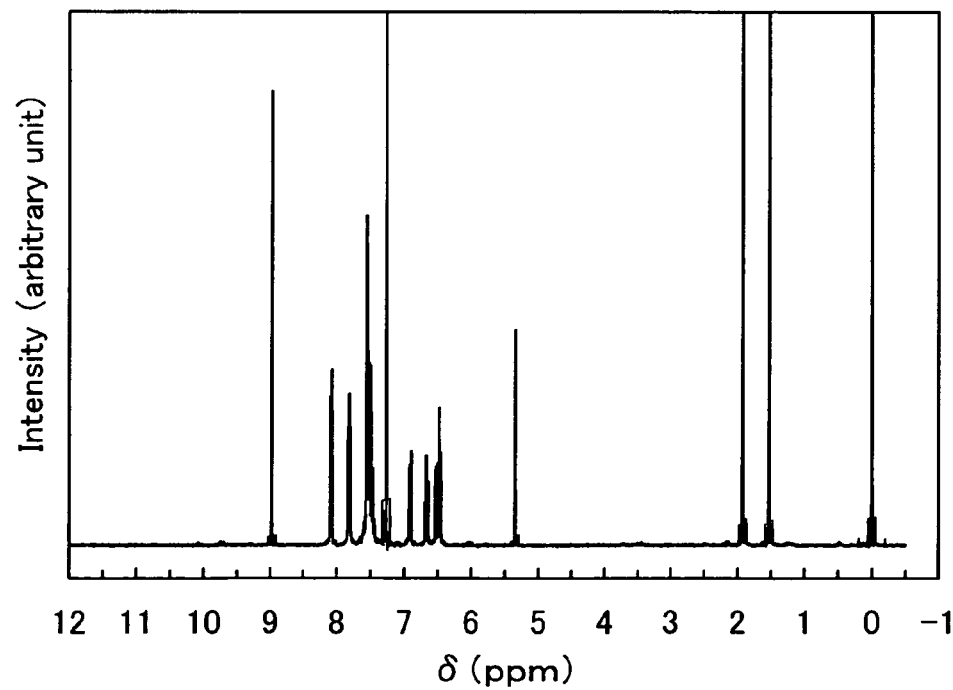

The red powder obtained in above Step 3 is analyzed by nuclear magnetic resonance spectrometry ($^1$H NMR). FIGS. 32A and 32B each show a $^1$H NMR chart. FIG. 32B shows an expanded view of FIG. 32A in the vertical axis direction. The result confirms that the organometallic complex Ir(tppr)$_2$(acac) represented by the above structural formula (402) is obtained in this synthetic example 1.

$^1$H NMR (CDCl$_3$, 300 MHz): δ=1.92 (s, 6H), 5.35 (s, 1H), 6.45-6.54 (m, 4H), 6.67 (td, 2H), 6.91 (d, 2H), 7.41-7.57 (m, 12H), 7.81 (m, 4H), 8.08 (dd, 4H), 8.98 (s, 2H).

Further, the decomposition temperature ($T_d$) of the obtained organometallic complex Ir(tppr)$_2$(acac), measured by a thermogravimetric/differential thermal analyzer (TG/DTA 320, manufactured by Seiko Instruments Inc.), is 331° C. Therefore, it is found that Ir(tppr)$_2$(acac) has excellent thermal stability.

Figure 33:
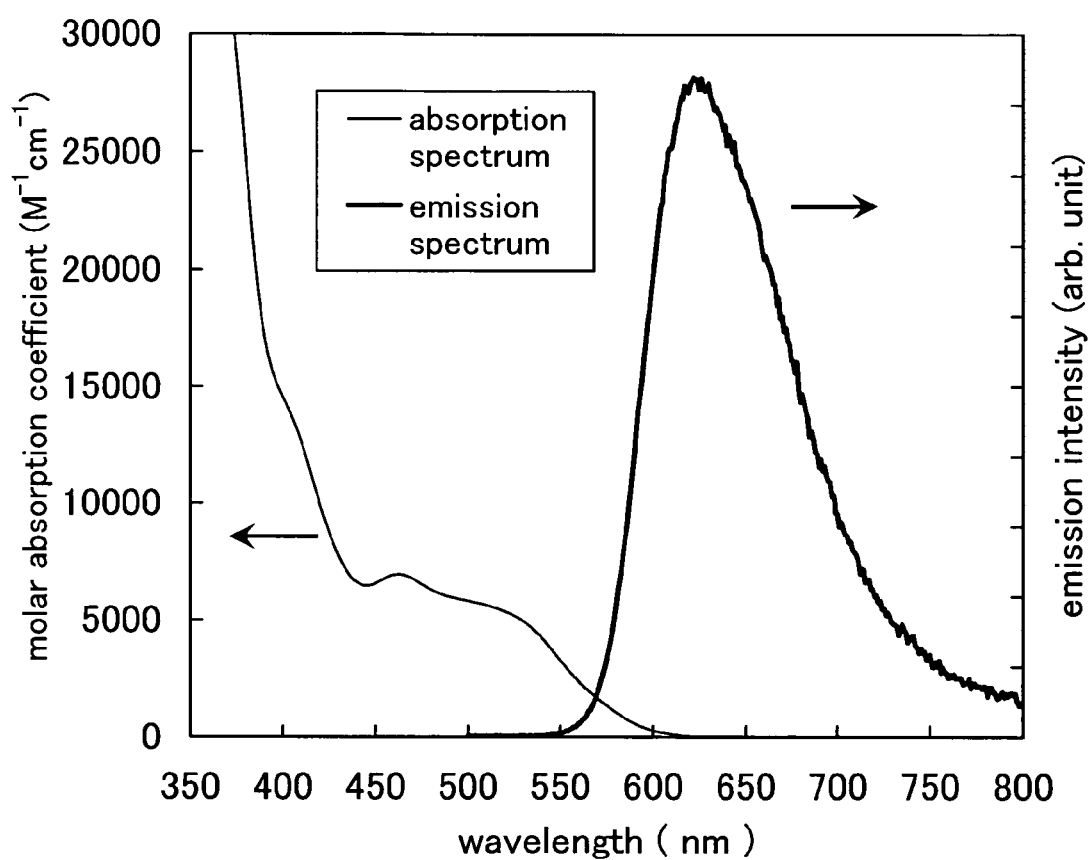
FIG. 33 is a graph showing an absorption spectrum and emission spectrum of (acetylacetonato)bis(2,3,5-triphenylpyrazinato)iridium(II) (Ir(tppr)$_2$(acac)).

Next, the absorption spectrum of Ir(tppr)$_2$(acac) is measured using an ultraviolet-visible spectrophotometer (V-550, manufactured by JASCO Corporation). The measurement is conducted by using a degassed dichloromethane solution (0.10 mmol/L) at room temperature. Furthermore, the emission spectrum of Ir(tppr)$_2$(acac) is measured using a fluorescence spectrophotometer (FS920, manufactured by Hamamatsu Photonics Corporation). The measurement is conducted by using a degassed dichloromethane solution (0.35 mmol/L) at room temperature. FIG. 33 shows the measurement results. The horizontal axis indicates a wavelength and the vertical axis indicates a molar absorption coefficient and emission intensity.

The organometallic complex Ir(tppr)$_2$(acac) has an emission peak at 622 nm, and emission of red-orange light is observed from the solution (FIG. 33).

It is observed that the organometallic complex Ir(tppr)$_2$(acac) has several absorption peaks in the visible light region. This absorption is unique to some organometallic complexes such as an ortho-metalated complex, and is considered to correspond to singlet MLCT transition, triplet π-π* transition, triplet MLCT transition, or the like. In particular, the longest wavelength absorption peak extends over a broad range in the visible light region. Thus, this absorption is considered to correspond to the triplet MLCT transition. In other words, it is considered that the organometallic complex Ir(tppr)$_2$(acac) is a compound capable of direct photo-excitation to a triplet excited state and intersystem crossing. Therefore, it can be considered that obtained emission is light emission from the triplet excited state, that is, phosphorescence.

[Step 4]

A synthetic method of 2,3,5-triphenylpyrazine (Htppr) synthesized in above Step 1, which is different from that of Step 1, is exemplified.

First, 4.60 g of phenylglyoxal (produced by Tokyo Chemical Industries Co., Ltd.) and 7.28 g of meso-1,2-diphenylethylenediamine are mixed in a solvent of ethanol (200 mL), and the mixture is refluxed for 6 hours under a nitrogen atmosphere. After the reflux, the solvent of this mixture is evaporated, and the obtained residue is recrystallized with ethanol. The ocher powder obtained by the recrystallization is dissolved in dichloromethane, and to this solution is added an excess amount of manganese dioxide. The mixture is stirred sufficiently, and then filtered. After the solvent of the filtrate is evaporated, the obtained residue is recrystallized with ethanol to give a pyrazine derivative Htppr (a yellow powder, 37% yield). A synthetic scheme of Step 4 is shown in the following (G-1-2).

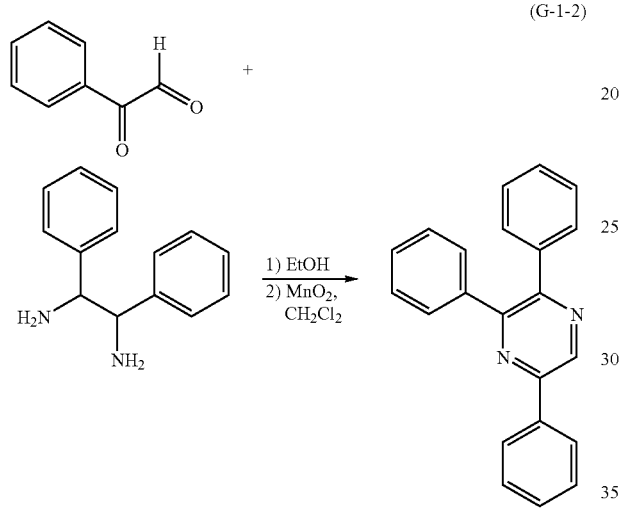

(G-1-2)

This application is based on Japanese Patent Application serial no. 2007-050244 filed on Feb. 28, 2007, filed with Japan Patent Office, the entire contents of which are hereby incorporated by reference.

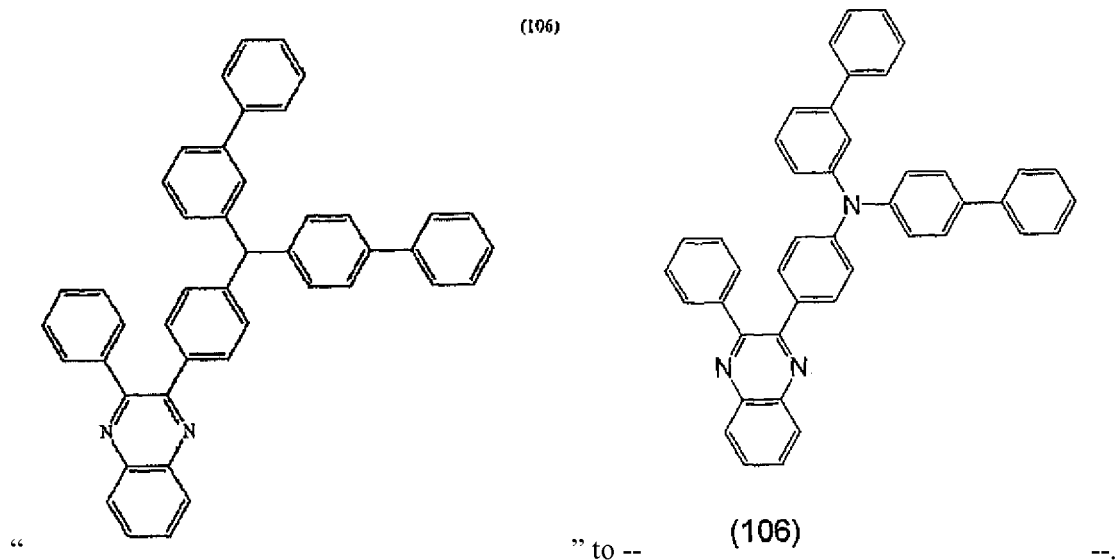

What is claimed is:

1. A quinoxaline derivative represented by a general formula (1):

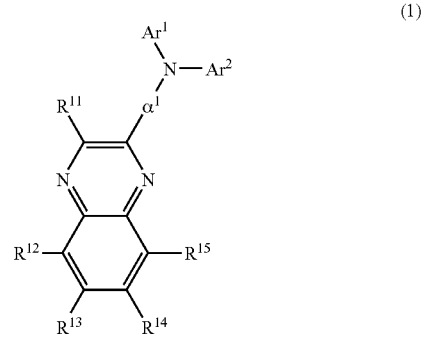

(1)

wherein $Ar^1$ represents one selected from a substituted or unsubstituted biphenyl group, or a substituted or unsubstituted terphenyl group, wherein $Ar^2$ represents one selected from a substituted or unsubstituted phenyl group, a substituted or unsubstituted biphenyl group, or a substituted or unsubstituted terphenyl group, wherein $\alpha^1$ represents an arylene group having 6 to 25 carbon atoms, wherein $R^{12}$ to $R^{15}$ are the same or different from one another, and each of them represents one selected from a hydrogen atom, an alkyl group having 1 to 4 carbon atoms, or a substituted or unsubstituted aryl group having 6 to 25 carbon atoms, wherein $R^{11}$ represents an alkyl group having 1 to 4 carbon atoms, and wherein a substituent on $Ar^1$ and $Ar^2$ is an alkyl group having 1 to 4 carbon atoms.

2. The quinoxaline derivative according to claim 1, wherein $\alpha^1$ represents an arylene group having 6 to 25 carbon atoms, which is not a condensed ring, and wherein $R^{12}$ to $R^{15}$ are the same or different from one another, and each of them represents one selected from a hydrogen atom, an alkyl group having 1 to 4 carbon atoms, or a substituted or unsubstituted aryl group having 6 to 25 carbon atoms, which is not a condensed ring.

3. The quinoxaline derivative according to claim 1, wherein $\alpha^1$ represents one selected from a phenylene group, a biphenyl-diyl group, or a fluorene-diyl group, and wherein $R^{12}$ to $R^{15}$ are the same or different from one another, and each of them represents one selected from a hydrogen atom, an alkyl group having 1 to 4 carbon atoms, a substituted or unsubstituted phenyl group, a substituted or unsubstituted biphenyl group, or a substituted or unsubstituted fluorene group.

4. The quinoxaline derivative according to claim 1, wherein $\alpha^1$ represents one selected from a phenylene group or a biphenyl-diyl group, and wherein $R^{12}$ to $R^{15}$ are the same or different from one another, and each of them represents one selected from a hydrogen atom, an alkyl group having 1 to 4 carbon atoms, a substituted or unsubstituted phenyl group, or a substituted or unsubstituted biphenyl group.

5. A quinoxaline derivative represented by a general formula (5) comprising:

an amine group represented by a structural formula (300); and a quinoxaline group represented by a structural formula (400),

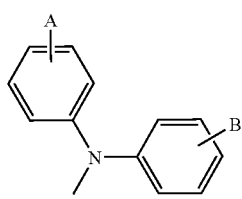

(300)

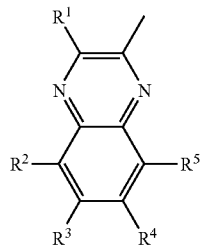

(400)

-continued (5)

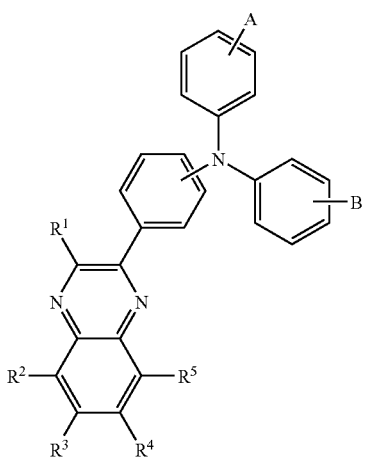

wherein A represents an unsubstituted phenyl group, wherein B represents one selected from a hydrogen atom or an unsubstituted phenyl group, wherein $R^2$ to $R^5$ are the same or different from one another, and each of them represents one selected from a hydrogen atom, an alkyl group having 1 to 4 carbon atoms, a substituted or unsubstituted phenyl group, or a substituted or unsubstituted biphenyl group, and wherein $R^1$ represents an alkyl group having 1 to 4 carbon atoms.

6. The quinoxaline derivative according to claim 5, wherein the amine group is bonded to a phenyl group at a para position, and the phenyl group is bonded to the quinoxaline group.

7. The quinoxaline derivative according to claim 5,
wherein the amine group is bonded to a phenyl group at a para position, and the phenyl group is bonded to the quinoxaline group, and
wherein $R^2$ to $R^5$ each represent a hydrogen atom.

8. The quinoxaline derivative according to claim 5,
wherein the amine group represented by the structural formula (300) is represented by a structural formula (301),
wherein the amine group represented by the structural formula (301) is bonded to a phenyl group at a para position, and the phenyl group is bonded to the quinoxaline group, and
wherein $R^2$ to $R^5$ each represent a hydrogen atom, (301)

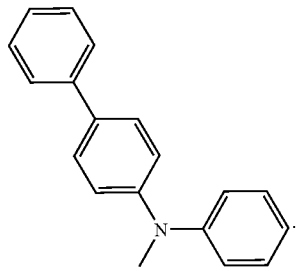

9. The quinoxaline derivative according to claim 5,
wherein the amine group is represented by a structural formula (302), wherein the amine group represented by the structural formula (302) is bonded to a phenyl group at a para position, and the phenyl group is bonded to the quinoxaline group, and wherein $R^2$ to $R^5$ each represent a hydrogen atom, (302)

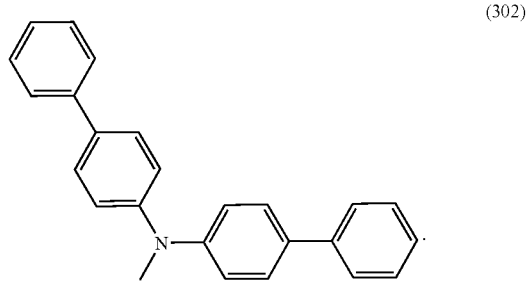

10. A light-emitting element comprising a light-emitting layer between a pair of electrodes,
wherein the light-emitting layer comprises:
an organometallic complex represented by a structural formula (402):

(402)

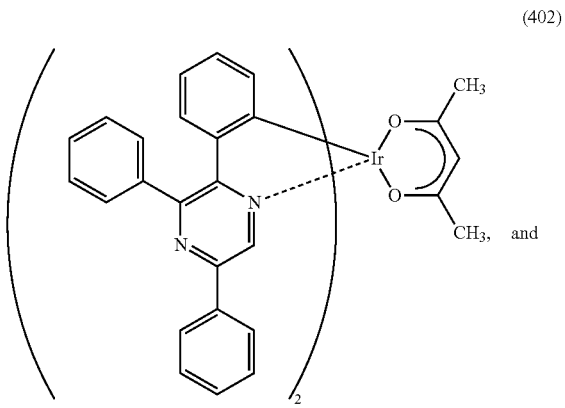

and a quinoxaline derivative represented by a general formula (1):

(1)

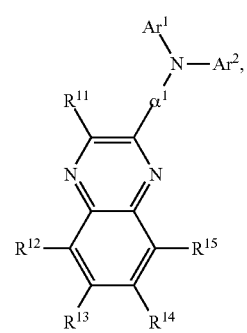

wherein $Ar^1$ represents one selected from a substituted or unsubstituted biphenyl group, or a substituted or unsubstituted terphenyl group, wherein Ar² represents one selected from a substituted or unsubstituted phenyl group, a substituted or unsubstituted biphenyl group, or a substituted or unsubstituted terphenyl group, wherein α¹ represents an arylene group having 6 to 25 carbon atoms, wherein $R^{12}$ to $R^{15}$ are the same or different from one another, and each of them represents one selected from a hydrogen atom, an alkyl group having 1 to 4 carbon atoms, or a substituted or unsubstituted aryl group having 6 to 25 carbon atoms, wherein $R^{11}$ represents an alkyl group having 1 to 4 carbon atoms, and wherein a substituent on Ar¹ and Ar² is an alkyl group having 1 to 4 carbon atoms.

11. The light-emitting element according to claim 10, wherein α¹ represents an arylene group having 6 to 25 carbon atoms, which is not a condensed ring, and wherein $R^{12}$ to $R^{15}$ are the same or different from one another, and each of them represents one selected from a hydrogen atom, an alkyl group having 1 to 4 carbon atoms, or a substituted or unsubstituted aryl group having 6 to 25 carbon atoms, which is not a condensed ring.

12. The light-emitting element according to claim 10, wherein α¹ represents one selected from a phenylene group, a biphenyl-diyl group, or a fluorene-diyl group, and wherein $R^{12}$ to $R^{15}$ are the same or different from one another, and each of them represents one selected from a hydrogen atom, an alkyl group having 1 to 4 carbon atoms, a substituted or unsubstituted phenyl group, a substituted or unsubstituted biphenyl group, or a substituted or unsubstituted fluorene group.

13. The light-emitting element according to claim 10, wherein α¹ represents one selected from a phenylene group or a biphenyl-diyl group, and wherein $R^{12}$ to $R^{15}$ are the same or different from one another, and each of them represents one selected from a hydrogen atom, an alkyl group having 1 to 4 carbon atoms, a substituted or unsubstituted phenyl group, or a substituted or unsubstituted biphenyl group.

14. A light-emitting element comprising a light-emitting layer between a pair of electrodes, wherein the light-emitting layer comprises:

an organometallic complex represented by a structural formula (402):

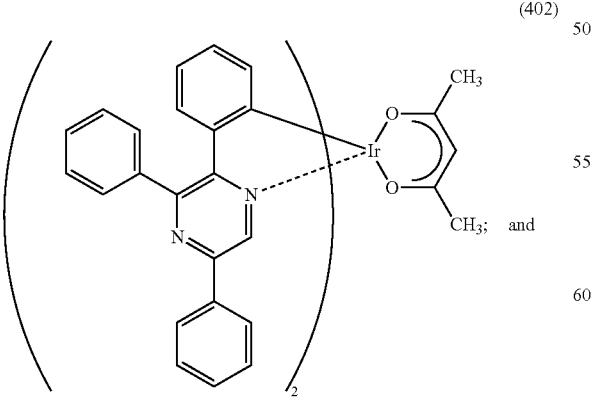

a quinoxaline derivative represented by a general formula (5), wherein the quinoxaline derivative comprising an amine group represented by a structural formula (300) and a quinoxaline group represented by a structural formula (400),

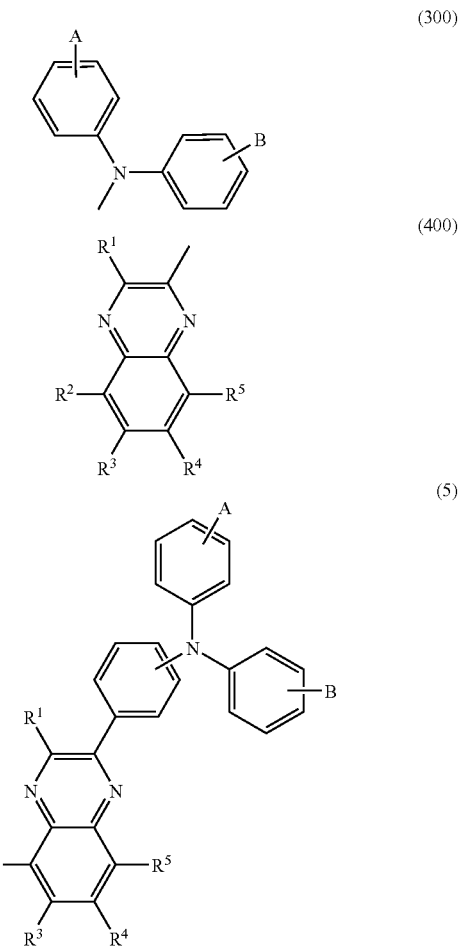

wherein A represents an unsubstituted phenyl group, wherein B represents one selected from a hydrogen atom or an unsubstituted phenyl group, wherein $R^2$ to $R^5$ are the same or different from one another, and each of them represents one selected from a hydrogen atom, an alkyl group having 1 to 4 carbon atoms, a substituted or unsubstituted phenyl group, or a substituted or unsubstituted biphenyl group, and wherein $R^1$ represents an alkyl group having 1 to 4 carbon atoms.

15. The light-emitting element according to claim 14, wherein the amine group is bonded to a phenyl group at a para position, and the phenyl group is bonded to the quinoxaline group.

16. The light-emitting element according to claim 14, wherein the amine group is bonded to a phenyl group at a para position, and the phenyl group is bonded to the quinoxaline group, and wherein $R^2$ to $R^5$ each represent a hydrogen atom.

17. The light-emitting element according to claim 14, wherein the amine group represented by the structural formula (300) is represented by a structural formula (301), wherein the amine group represented by the structural formula (301) is bonded to the phenyl group at a para position, and the phenyl group is bonded to the quinoxaline group, and wherein $R^2$ to $R^5$ each represent a hydrogen atom,

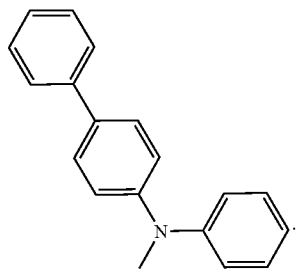

(301)

18. The light-emitting element according to claim 14, wherein the amine group represented by the structural formula 300) is represented by a structural formula (302), wherein the amine group represented by the structural formula (302) is bonded to the phenyl group at a para position, and the phenyl group is bonded to the quinoxaline group, and wherein $R^2$ to $R^5$ each represent a hydrogen atom,

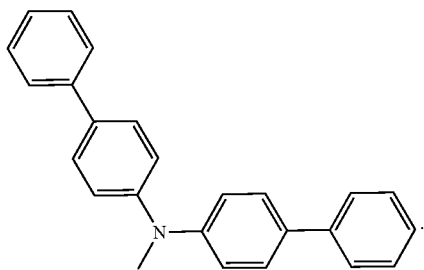

(302)

19. A lighting device comprising the quinoxaline derivative according to claim 1.

20. A lighting device comprising the quinoxaline derivative according to claim 5.

21. A lighting device comprising the light-emitting element according to claim 10.

22. A lighting device comprising the light-emitting element according to claim 14.

* * * * *

UNITED STATES PATENT AND TRADEMARK OFFICE
CERTIFICATE OF CORRECTION

| | |
|---|---|
| PATENT NO. | : 8,178,216 B2 |
| APPLICATION NO. | : 12/070650 |
| DATED | : May 15, 2012 |
| INVENTOR(S) | : Hiroko Nomura et al. |

It is certified that error appears in the above-identified patent and that said Letters Patent is hereby corrected as shown below:

In the Specification:

Column 9, Line 39; Change "[N,N-di(biphenyl-4-ylamino]" to --[N,N-di(biphenyl-4-yl)amino]--.

Column 10, Line 6; Change "iridium(II)" to --iridium (III)--.

Column 88, Lines 48-49; Change "general formula $\alpha^1$)" to --general formula (1)--.

Column 102, Line 64; Change "(2-phenylquinolnato-N,$C^{2'}$)" to --(2-phenylquinolinato-N,$C^{2'}$)--.

Column 105, Line 19; Change "gate voltages" to --gate voltage--.

Column 105, Line 63; Change "FIG. 51B" to --FIG. 5B--.

Column 109, Line 8; Change "FIG. 1D" to --FIG. 7D--.

Column 117, Line 14; Change "BBa1PQ axe examined" to --BBA1PQ are examined--.

Column 119, Line 26; Change "(BA1q)" to --(Balq)--.

Column 120, Line 26; Change "(BA1q)" to --(Balq)--.

Signed and Sealed this
Twentieth Day of January, 2015

Michelle K. Lee
*Deputy Director of the United States Patent and Trademark Office*

CERTIFICATE OF CORRECTION (continued)
U.S. Pat. No. 8,178,216 B2

Column 35, Lines 27-47; Change